United States Patent
Tarby et al.

(10) Patent No.: US 12,037,323 B2
(45) Date of Patent: Jul. 16, 2024

(54) URACIL DERIVATIVES AS Mer-AXL INHIBITORS

(71) Applicant: BRISTOL-MYERS SQUIBB COMPANY, Princeton, NJ (US)

(72) Inventors: Christine M. Tarby, Lawrenceville, NJ (US); Derek J. Norris, Pennington, NJ (US); Julian C. Lo, Hamilton, NJ (US); Vijay T. Ahuja, Princeton, NJ (US); Steven P. Seitz, Swarthmore, PA (US); Ashvinikumar V. Gavai, Princeton Junction, NJ (US); John S. Tokarski, Princeton, NJ (US); Mohini Rajasagi, Jersey City, NJ (US); Michael Wichroski, Yardley, PA (US); Matthias Broekema, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 926 days.

(21) Appl. No.: 17/052,232

(22) PCT Filed: May 2, 2019

(86) PCT No.: PCT/US2019/030310
§ 371 (c)(1),
(2) Date: Nov. 2, 2020

(87) PCT Pub. No.: WO2019/213340
PCT Pub. Date: Nov. 7, 2019

(65) Prior Publication Data
US 2023/0339891 A1 Oct. 26, 2023

Related U.S. Application Data

(60) Provisional application No. 62/666,159, filed on May 3, 2018.

(51) Int. Cl.
C07D 401/14 (2006.01)
C07D 405/14 (2006.01)
C07D 417/14 (2006.01)
C07D 471/04 (2006.01)

(52) U.S. Cl.
CPC ......... *C07D 401/14* (2013.01); *C07D 405/14* (2013.01); *C07D 417/14* (2013.01); *C07D 471/04* (2013.01)

(58) Field of Classification Search
CPC .................................................... C07D 401/14
See application file for complete search history.

(56) References Cited

FOREIGN PATENT DOCUMENTS

| WO | 13074633 A1 | 5/2013 |
|---|---|---|
| WO | 15017607 A2 | 2/2015 |
| WO | 19101178 A1 | 5/2019 |

OTHER PUBLICATIONS

Zhang et al. CAS: 160:7404, 2013.*

* cited by examiner

*Primary Examiner* — Rei Tsang Shiao
(74) *Attorney, Agent, or Firm* — Elliott Korsen

(57) ABSTRACT

The invention relates generally to compounds that are Mer-Ax1 inhibitors, pharmaceutical compositions containing said compounds and methods of treating proliferative disorders and disorders of dysregulated apoptosis, such as cancer, utilizing the compounds of the invention.

10 Claims, No Drawings
Specification includes a Sequence Listing.

SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: Peptide

<400> SEQUENCE: 1

```
Phe Ile Thr Cys Ala His Ala Lys Lys Lys Lys Glu Glu Ile Tyr Phe
1               5                   10                  15

Phe Phe Gly His
            20
```

URACIL DERIVATIVES AS Mer-AXL INHIBITORS

CROSS-REFERENCE TO RELATED APPLICATIONS

This application claims the benefit of U.S. Provisional Application No. 62/666,159, filed May 3, 2018, the disclosure of which is incorporated herein by reference in its entirety.

FIELD OF THE INVENTION

The invention relates generally to compounds that inhibit the activity of Mer and AXL Kinases, pharmaceutical compositions containing said compounds, which are useful for the treatment of disorders such as cancer.

BACKGROUND OF THE INVENTION

Receptor tyrosine kinases are cell surface proteins that transmit signals from the extracellular environment to the cell cytoplasm and nucleus to regulate cellular events such as growth, survival, differentiation, adhesion, migration and proliferation.

The tumor-associated macrophage (TAM) subfamily are an emerging class of innate immune checkpoints that may be active in key steps of anti-tumor immunity. They have a pivotal role in the homeostatic regulation of the immune system. Cancer immunotherapy using T-cell checkpoint inhibitors, such as Opdivo® has been very successful in a subset of patients. However, unresponsive patients tend to have non T-cell inflamed tumors that lack markers associated with those that have shown to be effective with the checkpoint inhibitors. Thus, identifying targets that regulate innate immune cell functions is likely to lead to the development of improved cancer therapies.

The TAM subfamily consists of three RTKs including Tyro3, AXL and Mer. They are characterized by an extracellular ligand binding domain consisting of 2 Ig-like domains and 2 fibronectin type III domains. Two ligands, growth arrest specific 6 (GAS6) and protein S (PROS1), have been identified as cognate ligands that bind and activate the TAM receptors.

AXL, also known as ARK, UFO, JTK11 and TYR07, has been linked to epithelial-mesenchymal transition (EMT) and promoting cell survival, anoikis resistance and metastasis in several cancers. The role of AXL in EMT has been documented in literature for breast, ovarian, non-small cell lung and pancreatic cancers and for glioblastoma among others.

MerTK (c-Mer Tyrosine Kinase; proto-oncogene tyrosine-protein kinase MER) is a member of the TAM (Tyro3/Axl/Mer) family of protein receptor tyrosine kinases (RTKs), which exhibit a similar overall structure comprising from the N-termini two Ig-like C2-type domains, two fibronectin (Fn) type-III domains, followed by a hydrophobic transmembrane domain and an intracellular tyrosine kinase domain. The two Ig-like domains serve as the ligand-binding regions of the TAMs.

TAM RTKs are ectopically expressed or overexpressed in a wide variety of human cancers, especially hematological and epithelial malignancies. Rather than functioning as oncogenic drivers, their induction in tumor cells predominantly promotes survival, chemoresistance and motility (Linger et al., 2008; Graham et al., 2014). Although MERTK knockdown only modestly promotes apoptosis and slows proliferation in cell cultures, the effect is more pronounced under stressful conditions such as when combined with serum starvation or growth in soft agar or xenografts (Lee-Sherick et al., 2013; Linger et al., 2013). This suggests that TAM survival signals may be particularly important in the tumor microenvironment, in which limited oxygen and nutrient supplies exacerbate the proteotoxic and genotoxic conditions.

Activation of TAMs on tumor cells derive tumor growth and metastasis via downstream effector signaling leading to tumor cell survival, proliferation, chemoresistance and EMT phenotypes. However, activation of TAMs on the professional phagocytes such as dendritic cells (DCs), leads to engulfment of apoptotic cells which in turn drives immune evasion by inhibiting T-cell priming and activation as well as via inhibition of NF-κB and inflammatory cytokine production. Hence, TAMs may act as dual tumorigenic gene products, first by acting as drivers of tumor growth, and then by acting as inhibitory immune receptors in the tumor microenvironment (Davra et al., Cancers 2016, 8, 107).

Thus, the TAM receptor tyrosine kinases are an emerging target of innate immune checkpoint blockade for many different types of cancers

SUMMARY OF THE INVENTION

In a first aspect of the present invention, there is provided a compound of formula

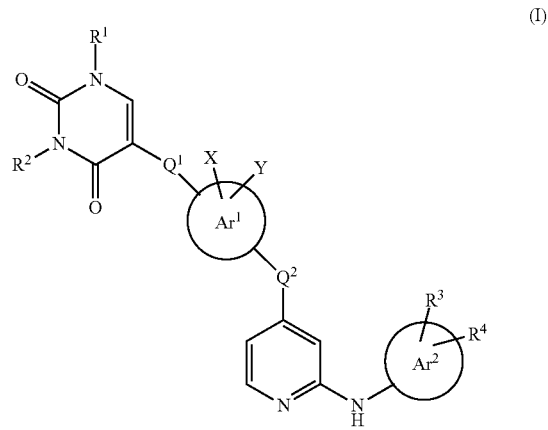

(I)

wherein:
Ar$^1$ is $C_3$-$C_8$ aryl or $C_3$-$C_8$ heteroaryl containing 1-4 heteroatoms selected from —N—, —O— or —S—;
Ar$^2$ is $C_3$-$C_8$ heteroaryl containing 1-4 heteroatoms selected from —N—, —O— or —S;
Q$^1$ is —NHCO—, —CONH—, —NHSO$_2$—, —SO$_2$NH—, —NHSO$_2$NH—, —NHCONH— or |—OCONH—;
Q$^2$ is —O— or —NH—;
R$^1$ and R$^2$ are independently hydrogen, $C_1$-$C_6$ alkyl, —(CH$_2$)$_r$$C_3$-$C_8$ cycloalkyl, —(CH$_2$)$_r$$C_3$-$C_8$ aryl or —(CH$_2$)$_r$$C_3$-$C_8$ heteroaryl containing 1-4 heteroatoms selected from —N—, —O— or —S—, said alkyl, cycloalkyl, aryl and heteroaryl groups substituted with 0-4 R$^{1a}$ groups;
R$^{13}$ is hydrogen, halogen, CF$_3$, $C_1$-$C_3$ alkyl, $C_1$-$C_3$ alkoxy or —COC$_1$-$C_3$ alkyl;
R$^3$ and R$^4$ are independently hydrogen, halogen, CF$_3$, CN, $C_1$-$C_6$ alkyl, $C_1$-$C_6$ alkoxy, $C_3$-$C_8$ heterocyclyl containing 1-4 heteroatoms selected from —N—, —O— or —S—, —CONR⁵R⁶, —NR⁵COR⁶, —NR⁵SO₂R⁶, —SO₂R⁵, —SO₂NR⁵R⁶, —NR⁵R⁶ or —NCOOR⁵, said alkyl, heterocyclyl and alkoxy groups substituted with 0-4 R³ᵃ groups;

R³³ is hydrogen, halogen, CHF₂, CF₃, $C_1$-$C_6$ alkyl, $C_1$-$C_3$ alkoxy. —(CH₂)ᵣCOOR⁵, OR⁵, —SO₂R⁵, —SO₂NR⁵R⁶, —NR⁵R⁶, NR⁵COOR⁶ or —COC₁-C₃ alkyl;

R⁵ and R⁶ are independently hydrogen, $C_1$-$C_6$ alkyl or $C_3$-$C_8$ aryl, said aryl and alkyl groups substituted with 0-4 R⁵ᵃ; or R⁵ and R⁶ together with the nitrogen atoms to which they are attached form a heterocyclic ring containing 0-2 additional heteroatoms selected from —N—, —O— or —S— and are substituted with 0-2 R⁵ᵃ groups;

R⁵ᵃ is hydrogen, halogen, OH or $C_1$-$C_3$ alkyl;

X and Y are independently are independently hydrogen, halogen, $C_1$-$C_6$ alkyl, $C_1$-$C_6$ alkoxy, CN, —CONR⁵R⁶, —NR⁵COR⁶, —NR⁵SO₂R⁶, —SO₂R⁵, —SO₂NR⁵R⁶, —NR⁵R⁶ or —NCOOR⁵, said alkyl and alkoxy groups substituted with 0-4 R³ groups;

r is 0, 1 or 2;

or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a compound of the invention or a pharmaceutically acceptable salt thereof for use in therapy. In particular, for use in the treatment of a disease or condition for which a Mer-Axl inhibitor is indicated.

DETAILED DESCRIPTION OF THE INVENTION

In a first aspect of the present invention, there is provided a compound of formula (I)

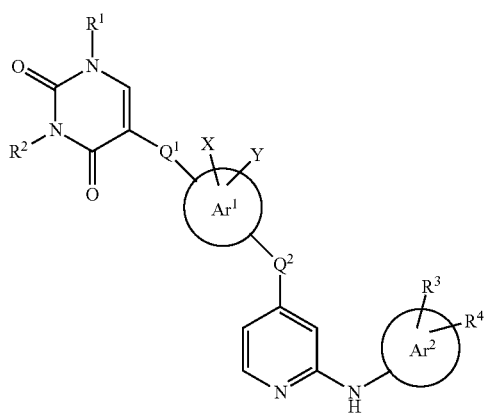

(I)

wherein:
Ar¹ is $C_3$-$C_8$ aryl or $C_3$-$C_8$ heteroaryl containing 1-4 heteroatoms selected from —N—, —O— or —S—;
Ar² is $C_3$-$C_8$ heteroaryl containing 1-4 heteroatoms selected from —N—, —O— or —S;
Q¹ is —NHCO—, —CONH—, —NHSO₂—, —SO₂NH—, —NHSO₂NH—, —NHCONH— or —OCONH—;

Q² is —O— or —NH—;
R¹ and R² are independently hydrogen, $C_1$-$C_6$ alkyl, —(CH₂)ᵣC₃-C₈ cycloalkyl, —(CH₂)ᵣC₃-C₈ aryl or —(CH₂)ᵣC₃-C₈ heteroaryl containing 1-4 heteroatoms selected from —N—, —O— or —S—, said alkyl, cycloalkyl, aryl and heteroaryl groups substituted with 0-4 Ria groups;
R¹ᵃ is hydrogen, halogen, CF₃, $C_1$-$C_3$ alkyl, $C_1$-$C_3$ alkoxy or —COC₁-C₃ alkyl;
R³ and R⁴ are independently hydrogen, halogen, CF₃, CN, $C_1$-$C_6$ alkyl, $C_1$-$C_6$ alkoxy, $C_3$-$C_8$ heterocyclyl containing 1-4 heteroatoms selected from —N—, —O— or —S—, —CONR⁵R⁶, —NR⁵COR⁶, —NR⁵SO₂R⁶, —SO₂R⁵, —SO₂NR⁵R⁶, —NR⁵R⁶ or —NCOOR⁵, said alkyl, heterocyclyl and alkoxy groups substituted with 0-4 R³ᵃ groups;
R³ᵃ is hydrogen, halogen, CHF₂, CF₃, $C_1$-$C_6$ alkyl, $C_1$-$C_3$ alkoxy, —(CH₂)ᵣCOOR⁵, OR⁵, —SO₂R⁵. —SO₂NR⁵R⁶, —NR⁵R⁶, NR⁵COOR⁶ or —COC₁-C₃ alkyl;
R⁵ and R⁶ are independently hydrogen, $C_1$-$C_6$ alkyl or $C_3$-$C_8$ aryl, said aryl and alkyl groups substituted with 0-4 R⁵ᵃ; or R⁵ and R⁶ together with the nitrogen atoms to which they are attached form a heterocyclic ring containing 0-2 additional heteroatoms selected from —N—, —O— or —S— and are substituted with 0-2 R⁵ᵃ groups;
R⁵ᵃ is hydrogen, halogen, OH or $C_1$-$C_3$ alkyl;
X and Y are independently are independently hydrogen, halogen, $C_1$-$C_6$ alkyl, $C_1$-$C_6$ alkoxy. CN. —CONR⁵R⁶, —NR⁵COR⁶, —NR⁵SO₂R⁶, —SO₂R⁵, —SO₂NR⁵R⁶, —NR⁵R⁶ or —NCOOR⁵, said alkyl and alkoxy groups substituted with 0-4 R³ᵃ groups;
r is 0, 1 or 2;
or a pharmaceutically acceptable salt, tautomer or stereoisomer thereof.

In a second aspect within the scope of the first aspect of the invention, there is provided a compound of formula (I)

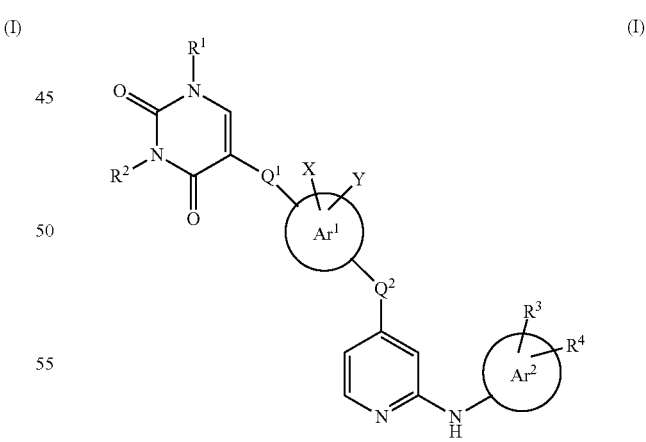

(I)

wherein:
Ar¹ is $C_3$-$C_8$ aryl
Ar² is $C_3$-$C_8$ heteroaryl containing 1-4 heteroatoms selected from —N—, —O— or —S;
Q¹ is —NHCO—, —CONH—, —NHSO₂—, —SO₂NH—. —NHSO₂NH—, —NHCONH— or —OCONH—;
Q² is —O— or —NH—;

$R^1$ and $R^2$ are independently hydrogen, $C_1$-$C_6$ alkyl, —$(CH_2)_rC_3$-$C_8$ cycloalkyl, —$(CH_2)_rC_3$-$C_8$ aryl or —$(CH_2)_rC_3$-$C_8$ heteroaryl containing 1-4 heteroatoms selected from —N—, —O— or —S—, said alkyl, cycloalkyl, aryl and heteroaryl groups substituted with 0-4 $R^{1a}$ groups;

$R^{1a}$ is hydrogen, halogen, $CF_3$, $C_1$-$C_3$ alkyl, $C_1$-$C_3$ alkoxy or —$COC_1$-$C_3$ alkyl;

$R^3$ and $R^4$ are independently hydrogen, halogen, $CF_3$, CN, $C_1$-$C_6$ alkyl, $C_1$-$C_6$ alkoxy, $C_3$-$C_8$ heterocyclyl containing 1-4 heteroatoms selected from —N—, —O— or —S—, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl, heterocyclyl and alkoxy groups substituted with 0-4 $R^{3a}$ groups;

$R^{3a}$ is hydrogen, halogen, $CHF_2$, $CF_3$, $C_1$-$C_6$ alkyl, $C_1$-$C_3$ alkoxy, —$(CH_2)_rCOOR^5$, $OR^5$, —$SO_2R^5$, —$SO_2NR^5R^6$, —$NR^5R^6$, $NR^5COOR^6$ or —$COC_1$-$C_3$ alkyl;

$R^1$ and $R^6$ are independently hydrogen, $C_1$-$C_6$ alkyl or $C_3$-$C_8$ aryl, said aryl and alkyl groups substituted with 0-4 $R^{5a}$; or $R^5$ and $R^6$ together with the nitrogen atoms to which they are attached form a heterocyclic ring containing 0-2 additional heteroatoms selected from —N—, —O— or —S— and are substituted with 0-2 $R^{5a}$ groups;

$R^{5a}$ is hydrogen, halogen, OH or $C_1$-$C_3$ alkyl;

X and Y are independently are independently hydrogen, halogen, $C_1$-$C_6$ alkyl, $C_1$-$C_6$ alkoxy, CN, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl and alkoxy groups substituted with 0-4 $R^3$ groups;

r is 0, 1 or 2;

or a pharmaceutically acceptable salt, tautomer or stereoisomer thereof.

In a third aspect within the scope of the prior aspects of the invention, there is provided a compound of formula (I)

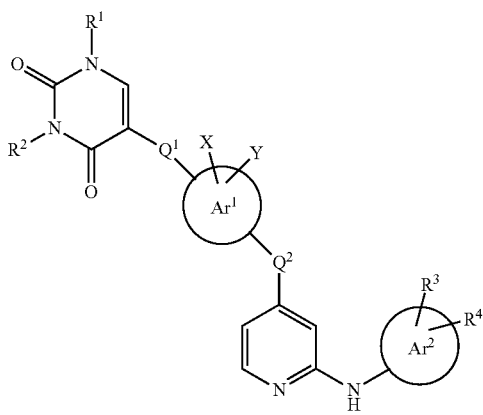

(I)

wherein:
$Ar^1$ is $C_3$-$C_8$ aryl
$Ar^2$ is $C_3$-$C_8$ heteroaryl containing 1-4 heteroatoms selected from —N—, —O— or —S;
$Q^1$ is —NHCO— or —CONH;
$Q^2$ is —O— or —NH—;
$R^1$ and $R^2$ are independently hydrogen, $C_1$-$C_6$ alkyl, —$(CH_2)_rC_3$-$C_8$ cycloalkyl, —$(CH_2)_rC_3$-$C_8$ aryl or —$(CH_2)_rC_3$-$C_8$ heteroaryl containing 1-4 heteroatoms selected from —N—, —O— or —S—, said alkyl, cycloalkyl, aryl and heteroaryl groups substituted with 0-4 $R^{1a}$ groups;

$R^{1a}$ is hydrogen, halogen, $CF_3$, $C_1$-$C_3$ alkyl, $C_1$-$C_3$ alkoxy or —$COC_1$-$C_3$ alkyl;

$R^3$ and $R^4$ are independently hydrogen, halogen, $CF_3$, CN, $C_1$-$C_6$ alkyl, $C_1$-$C_6$ alkoxy, $C_3$-$C_8$ heterocyclyl containing 1-4 heteroatoms selected from —N—, —O— or —S—, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl, heterocyclyl and alkoxy groups substituted with 0-4 $R^{3a}$ groups;

$R^{3a}$ is hydrogen, halogen, $CHF_2$, $CF_3$, $C_1$-$C_6$ alkyl, $C_1$-$C_3$ alkoxy, —$(CH_2)_rCOOR^5$, $OR^5$, —$SO_2R^5$, —$SO_2NR^5R^6$, —$NR^5R^6$, $NR^5COOR^6$ or —$COC_1$-$C_3$ alkyl;

$R^5$ and $R^6$ are independently hydrogen, $C_1$-$C_6$ alkyl or $C_3$-$C_8$ aryl, said aryl and alkyl groups substituted with 0-4 $R^{5a}$; or $R^5$ and $R^6$ together with the nitrogen atoms to which they are attached form a heterocyclic ring containing 0-2 additional heteroatoms selected from —N—, —O— or —S— and are substituted with 0-2 $R^{5a}$ groups;

$R^{5a}$ is hydrogen, halogen, OH or $C_1$-$C_3$ alkyl;

X and Y are independently are independently hydrogen, halogen, $C_1$-$C_6$ alkyl, $C_1$-$C_6$ alkoxy, CN, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl and alkoxy groups substituted with 0-4 $R^{3a}$ groups;

r is 0, 1 or 2;

or a pharmaceutically acceptable salt, tautomer or stereoisomer thereof.

In a fourth aspect within the scope of the prior aspects of the invention, there is provided a compound of formula (II)

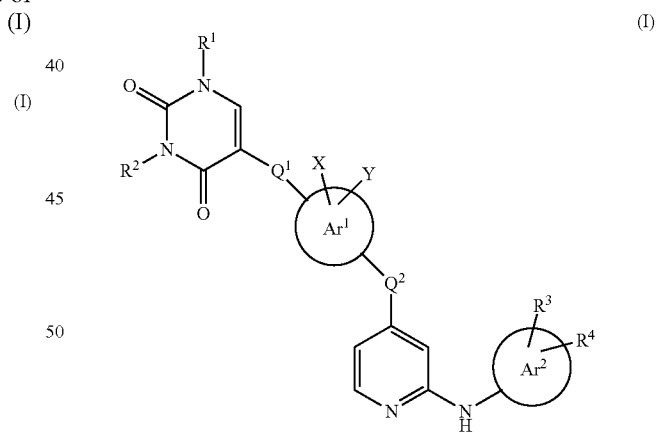

(I)

wherein:
$Ar^1$ is $C_3$-$C_8$ aryl
$Ar^2$ is $C_3$-$C_8$ heteroaryl containing 1-4 heteroatoms selected from —N—, —O— or —S;
$Q^1$ is —NHCO— or —CONH;
$Q^2$ is —O—;
$R^1$ and $R^2$ are independently hydrogen, $C_1$-$C_6$ alkyl, —$(CH_2)_rC_3$-$C_8$ cycloalkyl, —$(CH_2)_rC_3$-$C_8$ aryl or —$(CH_2)_rC_3$-$C_8$ heteroaryl containing 1-4 heteroatoms selected from —N—, —O— or —S—, said alkyl, cycloalkyl, aryl and heteroaryl groups substituted with 0-4 $R^{1a}$ groups;

$R^{1a}$ is hydrogen, halogen, $CF_3$, $C_1$-$C_3$ alkyl, $C_1$-$C_3$ alkoxy or —$COC_1$-$C_3$ alkyl;

$R^3$ and $R^4$ are independently hydrogen, halogen, $CF_3$, CN, $C_1$-$C_6$ alkyl, $C_1$-$C_6$ alkoxy, $C_3$-$C_8$ heterocyclyl containing 1-4 heteroatoms selected from —N—, —O— or —S—, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl, heterocyclyl and alkoxy groups substituted with 0-4 $R^{3a}$ groups;

$R^{3a}$ is hydrogen, halogen, $CHF_2$, $CF_3$, $C_1$-$C_6$ alkyl, $C_1$-$C_3$ alkoxy, —$(CH_2)_rCOOR^5$, $OR^5$, —$SO_2R^5$, —$SO_2NR^5R^6$, —$NR^5R^6$, $NR^5COOR^6$ or —$COC_1$-$C_3$ alkyl;

$R^5$ and $R^6$ are independently hydrogen. $C_1$-$C_6$ alkyl or $C_3$-$C_8$ aryl, said aryl and alkyl groups substituted with 0-4 $R^{5a}$; or $R^5$ and $R^6$ together with the nitrogen atoms to which they are attached form a heterocyclic ring containing 0-2 additional heteroatoms selected from —N—, —O— or —S— and are substituted with 0-2 $R^{5a}$ groups;

$R^{5a}$ is hydrogen, halogen, OH or $C_1$-$C_3$ alkyl;

X and Y are independently are independently hydrogen, halogen, $C_1$-$C_6$ alkyl, $C_1$-$C_6$ alkoxy, CN, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl and alkoxy groups substituted with 0-4 $R^{3a}$ groups;

r is 0, 1 or 2;

or a pharmaceutically acceptable salt, tautomer or stereoisomer thereof.

In a fifth aspect within the scope of the prior aspects of the invention, there is provided a compound of formula (II)

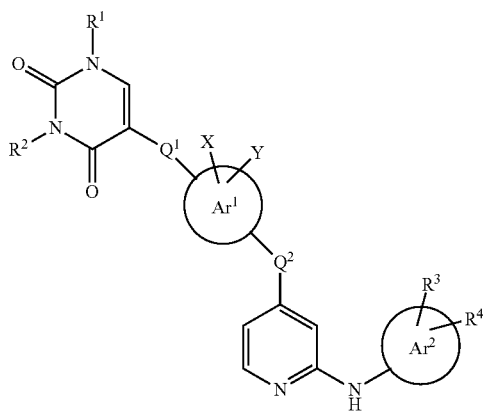

(I)

wherein:
$Ar^1$ is $C_3$-$C_8$ aryl
$Ar^2$ is $C_3$-$C_8$ heteroaryl containing 1-4 heteroatoms selected from —N—, —O— or —S;
$Q^1$ is —NHCO— or —CONH;
$Q^2$ is —O—;
$R^1$ and $R^2$ are independently hydrogen, $C_1$-$C_6$ alkyl, —$(CH_2)_rC_3$-$C_8$ cycloalkyl, —$(CH_2)_rC_3$-$C_8$ aryl or —$(CH_2)_rC_3$-$C_8$ heteroaryl containing 1-4 heteroatoms selected from —N—, —O— or —S—, said alkyl, cycloalkyl, aryl and heteroaryl groups substituted with 0-4 $R^{1a}$ groups;
$R^{1a}$ is hydrogen, halogen, $CF_3$, $C_1$-$C_3$ alkyl, $C_1$-$C_3$ alkoxy or —$COC_1$-$C_3$ alkyl;
$R^3$ and $R^4$ are independently hydrogen, halogen, $CF_3$, CN, $C_1$-$C_6$ alkyl, $C_1$-$C_6$ alkoxy, $C_3$-$C_8$ heterocyclyl containing 1-4 heteroatoms selected from —N—, —O— or —S—, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl, heterocyclyl and alkoxy groups substituted with 0-4 $R^{3a}$ groups;

$R^{3a}$ is hydrogen, halogen, $CHF_2$, $CF_3$, $C_1$-$C_6$ alkyl, $C_1$-$C_3$ alkoxy, —$(CH_2)_rCOOR^5$, $OR^5$, —$SO_2R^5$, —$SO_2NR^5R^6$, —$NR^5R^6$, $NR^5COOR^6$ or —$COC_1$-$C_3$ alkyl;

$R^5$ and $R^6$ are independently hydrogen, $C_1$-$C_6$ alkyl or $C_3$-$C_8$ aryl, said aryl and alkyl groups substituted with 0-4 $R^{5a}$; or $R^5$ and $R^6$ together with the nitrogen atoms to which they are attached form a heterocyclic ring containing 0-2 additional heteroatoms selected from —N—, —O— or —S— and are substituted with 0-2 $R^{5a}$ groups;

$R^{5a}$ is hydrogen, halogen, OH or $C_1$-$C_3$ alkyl;

X and Y are independently hydrogen, halogen or $C_1$-$C_6$ alkyl;

r is 0, 1 or 2;

or a pharmaceutically acceptable salt, tautomer or stereoisomer thereof.

In a sixth aspect within the scope of some of the prior aspects of the invention, there is provided a compound of formula (II)

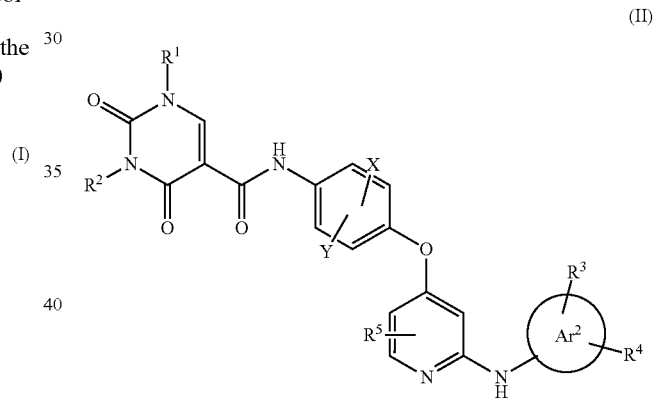

(II)

wherein:
$Ar^2$ is $C_3$-$C_8$ heteroaryl containing 1-4 heteroatoms selected from —N—, —O— or —S;
$R^1$ and $R^2$ are independently hydrogen, $C_1$-$C_6$ alkyl, —$(CH_2)_rC_3$-$C_8$ cycloalkyl, —$(CH_2)_rC_3$-$C_8$ aryl or —$(CH_2)_rC_3$-$C_8$ heteroaryl containing 1-4 heteroatoms selected from —N—, —O— or —S—, said alkyl, cycloalkyl, aryl and heteroaryl groups substituted with 0-4 $R^{1a}$ groups;
$R^{1a}$ is hydrogen, halogen, $CF_3$, $C_1$-$C_3$ alkyl, $C_1$-$C_3$ alkoxy or —$COC_1$-$C_3$ alkyl;
$R^3$ and $R^4$ are independently hydrogen, halogen, $CF_3$, CN, $C_1$-$C_6$ alkyl, $C_1$-$C_6$ alkoxy, $C_3$-$C_8$ heterocyclyl containing 1-4 heteroatoms selected from —N—, —O— or —S—, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl, heterocyclyl and alkoxy groups substituted with 0-4 $R^{3a}$ groups;

$R^{3a}$ is hydrogen, halogen, $CHF_2$, $CF_3$, $C_1$-$C_6$ alkyl, $C_1$-$C_3$ alkoxy, —$(CH_2)_rCOOR^5$, $OR^5$, —$SO_2R^5$, —$SO_2NR^5R^6$, —$NR^5R^6$, $NR^5COOR^6$ or —$COC_1$-$C_3$ alkyl;

R⁵ and R⁶ are independently hydrogen, $C_1$-$C_6$ alkyl or $C_3$-$C_8$ aryl, said aryl and alkyl groups substituted with 0-4 $R^{5a}$; or R⁵ and R⁶ together with the nitrogen atoms to which they are attached form a heterocyclic ring containing 0-2 additional heteroatoms selected from —N—, —O— or —S— and are substituted with 0-2 $R^{5a}$ groups;

$R^{5a}$ is hydrogen, halogen, OH or $C_1$-$C_3$ alkyl;

X and Y are independently hydrogen, halogen or $C_1$-$C_6$ alkyl;

r is 0, 1 or 2;

or a pharmaceutically acceptable salt, tautomer or stereoisomer thereof.

In a seventh aspect within the scope of the prior aspect of the invention, there is provided a compound of formula (II)

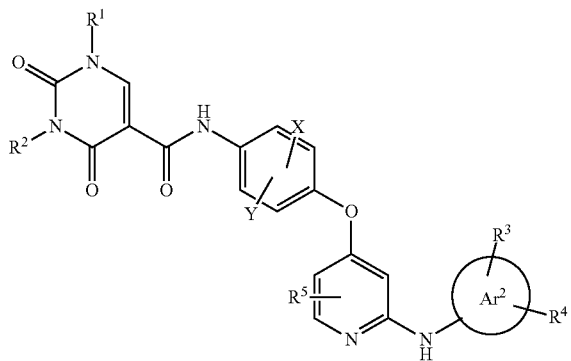

(II)

wherein:

$Ar^2$ is $C_3$-$C_8$ heteroaryl containing 1-4 heteroatoms selected from —N—, —O— or —S;

R¹ and R² are independently hydrogen. $C_1$-$C_6$ alkyl, —(CH₂)$_r$$C_3$-$C_8$ cycloalkyl, —(CH₂)$_r$$C_3$-$C_8$ aryl or —(CH₂)$_r$$C_3$-$C_8$ heteroaryl containing 1-4 heteroatoms selected from —N—, —O— or —S—, said alkyl, cycloalkyl, aryl and heteroaryl groups substituted with 0-4 $R^{1a}$ groups;

$R^{18}$ is hydrogen, halogen, $CF_3$, $C_1$-$C_3$ alkyl, $C_1$-$C_3$ alkoxy or —COC$_1$-$C_3$ alkyl;

R³ is hydrogen, halogen, $CF_3$, CN, $C_1$-$C_6$ alkyl, $C_1$-$C_6$ alkoxy, $C_3$-$C_8$ heterocyclyl containing 1-4 heteroatoms selected from —N—, —O— or —S—, —CONR⁵R⁶, —NR⁵COR⁶, —NR⁵SO₂R⁶, —SO₂R⁵, —SO₂NR⁵R⁶, —NR⁵R⁶ or —NCOOR⁵, said alkyl, heterocyclyl and alkoxy groups substituted with 0-4 R³ groups;

R⁴ is hydrogen, halogen, CN, $C_1$-$C_6$ alkyl, $C_3$-$C_8$ heterocyclyl containing 1-4 heteroatoms selected from —N—, —O— or —S— or —NR⁵R⁶, said alkyl, heterocyclyl and alkoxy groups substituted with 0-4 $R^{3a}$ groups;

$R^{3a}$ is hydrogen, halogen, $CHF_2$, $CF_3$. $C_1$-$C_6$ alkyl, $C_1$-$C_3$ alkoxy, —(CH₂)$_r$COOR⁵, OR⁵, —SO₂R⁵, —SO₂NR⁵R⁶, —NR⁵R⁶, NR⁵COOR⁶ or —COC$_1$-$C_3$ alkyl;

R⁵ and R⁶ are independently hydrogen, $C_1$-$C_6$ alkyl or $C_3$-$C_8$ aryl, said aryl and alkyl groups substituted with 0-4 $R^{5a}$; or R⁵ and R⁶ together with the nitrogen atoms to which they are attached form a heterocyclic ring containing 0-2 additional heteroatoms selected from —N—, —O— or —S— and are substituted with 0-2 $R^{5a}$ groups;

R⁵ is hydrogen, halogen, OH or $C_1$-$C_3$ alkyl;

X and Y are independently hydrogen, halogen or $C_1$-$C_6$ alkyl;

r is 0, 1 or 2;

or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another aspect, there is provided a compound selected from the following list N-[4-({2-[(5-cyanopyridin-2-yl)amino]pyridin-4-yl}oxy)-3-fluorophenyl]-3-(4-fluorophenyl)-2,4-dioxo-1-(propan-2-yl)-1,2,3,4-tetrahydropyrimidine-5-carboxamide, N-{4-[(2-([5-(difluoromethyl)pyridin-2-yl]amino}pyridin-4-yl)oxy]-3-fluorophenyl)-3-(4-fluorophenyl)-2,4-dioxo-1-(propan-2-yl)-1,2,3,4-tetrahydropyrimidine-5-carboxamide, N-[3-fluoro-4-({2-[(5-methanesulfonylpyridin-2-yl)amino]pyridin-4-yl}oxy)phenyl]-3-(4-fluorophenyl)-2,4-dioxo-1-(propan-2-yl)-1,2,3,4-tetrahydropyrimidine-5-carboxamide, N-{4-[(2-{[5-(dimethylsulfamoyl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide, N-{4-[(2-{[5-(dimethylsulfamoyl)pyridin-2-yl]amino}pyridin-4-yl)oxy]-3-fluorophenyl}-3-(4-fluorophenyl)-2,4-dioxo-1-[(3S)-oxolan-3-yl]-1,2,3,4-tetrahydropyrimidine-5-carboxamide, N-{4-[(2-{[5-(dimethylsulfamoyl)pyridin-2-yl]amino}pyridin-4-yl)oxy]-3-fluorophenyl}-3-(5-fluoropyridin-2-yl)-2,4-dioxo-1-(propan-2-yl)-1,2,3,4-tetrahydropyrimidine-5-carboxamide, N-(4-[(2-{[5-(dimethylsulfamoyl)pyridin-2-yl]amino}pyridin-4-yl)oxy]-3-fluorophenyl)-3-(4-fluorophenyl)-1-[(2S)-1-hydroxypropan-2-yl]-2,4-dioxo-1,2,3,4-tetrahydropyrimidine-5-carboxamide, N-{4-[(2-{[5-(dimethylsulfamoyl)pyridin-2-yl]amino}pyridin-4-yl)oxy]-3-fluorophenyl}-3-(3-fluorophenyl)-2,4-dioxo-1-(propan-2-yl)-1,2,3,4-tetrahydropyrimidine-5-carboxamide, N-{4-[(2-{[5-(dimethylsulfamoyl)pyridin-2-yl]amino}pyridin-4-yl)oxy]phenyl}-2,4-dioxo-3-phenyl-1-(propan-2-yl)-1,2,3,4-tetrahydropyrimidine-5-carboxamide, N-{3-fluoro-4-[(2-{[5-(methylsulfamoyl)pyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide, N-{4-[(2-{[5-(azetidine-1-sulfonyl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide, N-{4-[(2-{[5-(dimethylsulfamoyl)-4-methylpyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide, or a pharmaceutically acceptable salt thereof.

II. OTHER EMBODIMENTS OF THE INVENTION

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including without limitation, small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In another embodiment, the invention provides a method for the treatment and/or prophylaxis of various types of cancer, including without limitation, small cell lung cancer, non-small cell lung cancer, triple-negative breast cancer, colorectal cancer, prostate cancer, melanoma, pancreatic cancer, multiple myeloma, T-acute lymphoblastic leukemia or AML.

In another embodiment, the invention provides a method for the treatment and/or prophylaxis of fibrosis such as hepatic or pulmonary fibrosis.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

III. THERAPEUTIC APPLICATIONS

The compounds of formula (I) of the invention are Mer-Axl inhibitors and have potential utility in the treatment of diseases and conditions for which a Mer-Axl inhibitor is indicated.

In one embodiment there is provided a method for the treatment of a disease or condition, for which a Mer-Axl inhibitor is indicated, in a subject in need thereof which comprises administering a therapeutically effective amount of compound of formula (I) or a pharmaceutically acceptable salt thereof.

In another embodiment there is provided a method for treatment of a chronic autoimmune and/or inflammatory condition, in a subject in need thereof which comprises administering a therapeutically effective amount of one or more compounds of formula (I) or a pharmaceutically acceptable salt thereof.

In a further embodiment there is provided a method for treatment of cancer in a subject in need thereof which comprises administering a therapeutically effective amount of one or more compounds of formula (I) or a pharmaceutically acceptable salt thereof.

In one embodiment the subject in need thereof is a mammal, particularly a human.

Mer-Axl inhibitors may be useful in the treatment of cancer, including hematological, epithelial including lung, breast and colon carcinomas, midline carcinomas, mesenchymal, hepatic, renal and neurological tumours.

The term "diseases or conditions for which a Mer-Axl inhibitor is indicated" is intended to include any of or all of the above disease states.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma. Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT3R, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO131692(4: WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPD1VO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446: WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016

(WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment.

Furthermore, any element of an embodiment is meant to be combined with any and all other elements from any embodiment to describe an additional embodiment.

IV. PHARMACEUTICAL COMPOSITIONS AND DOSING

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, poly oxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "$C_2$-$C_8$ alkenyl" contains from two to eight carbon atoms. Alkenyl groups include, but are not limited to, for example, ethenyl, propenyl, butenyl, I-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "$C_2$-$C_8$ alkenyl" contains from two to eight carbon atoms. Representative alkynyl groups include, but are not limited to, for example, ethynyl, 1-propynyl, I-butynyl, heptynyl, octynyl and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

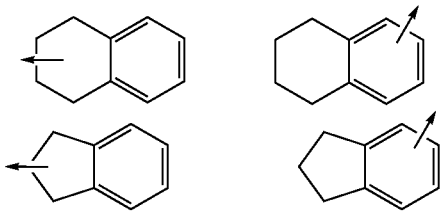

Arrowed lines drawn from the ring system indicate that the bond may be attached to any of the suitable ring atoms.

The term "benzyl," as used herein, refers to a methyl group on which one of the hydrogen atoms is replaced by a phenyl group.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl.

Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazoline-2-one, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are lactams containing from 3-7 ring atoms. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N-+O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the core of the compound.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent.

Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxy benzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry. Biochemistry and Enzymology*, VCHA and Wiley-VCH, Zurich. Switzerland (2003); Wermuth, C. G., ed., *The Practice of Medicinal Chemistry*, 3$^{rd}$ edition, Academic Press, San Diego, CA (2008).

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H (hydrogen), $^2$H (deuterium) and $^3$H (tritium). They are also commonly denoted as D for deuterium and T for tritium. In the application, $CD_3$ denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being affected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

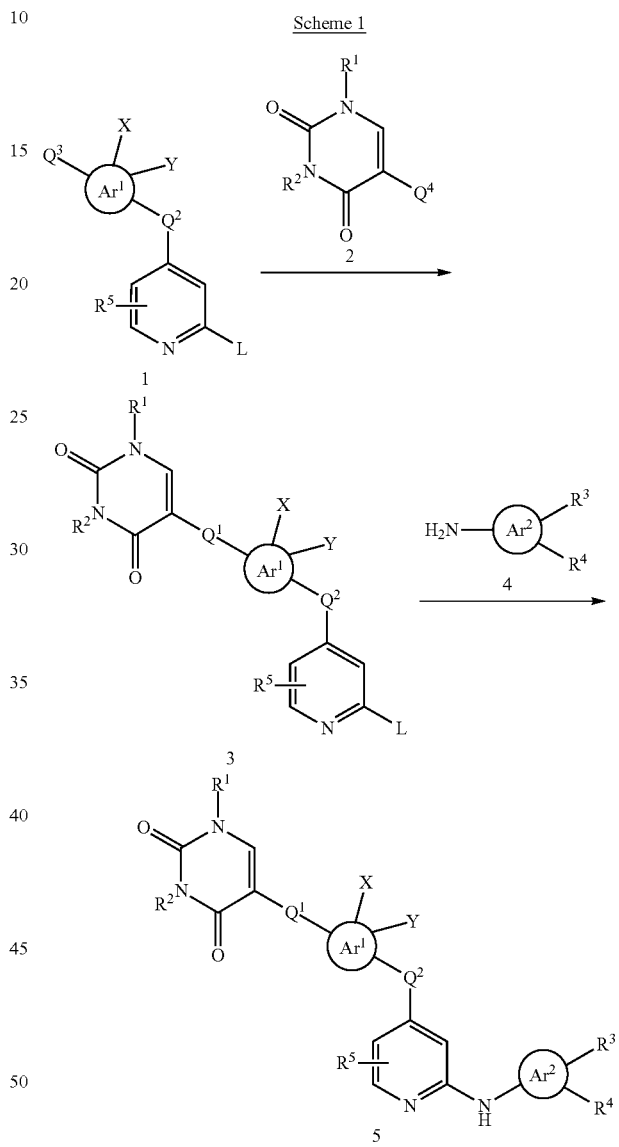

Scheme 1

General routes to compounds described in the invention are illustrated in Schemes 1-6, where the $R^1$, $R^2$, $R^3$, $R^4$, $R^5$, $Q^1$, $Q^2$, X and Y substituents are defined previously in the text or a functional group that can be converted to the desired final substituent. L is a leaving group such as a halide or OH that can be easily converted to a leaving group such as a triflate. As shown in Scheme 1, a general procedure for the preparation of compounds of the invention involves starting with a substituted pyridine 1. Coupling of 1 with a substituted uracil (2, where $Q^3$ and $Q^4$ are suitable coupling partners, such as —$NH_2$ or —$CO_2H$) using a suitable reagent can yield functionalized pyridines 3. For example, 3 could arise from an amide bond forming reaction between a carboxylic acid such as 1,3-dimethyl-2,4-dioxo-1,2,3,4-tetrahydropyrimidine-5-carboxylic acid and a suitably substituted aniline such as 4-((2-chloropyridin-4-yl)oxy)aniline using one of many available coupling reagents, such as HATU and EDCI. Subsequent coupling of 3 with a suitably substituted heteroarylamine 4 to provide biaryl amine 5 can be achieved using standard conditions known in the literature. For example, halopyridine 3 can undergo a Buchwald N-arylation reaction with heteroarylamine 4 using a suitable Pd catalyst to provide biarylamine 5.

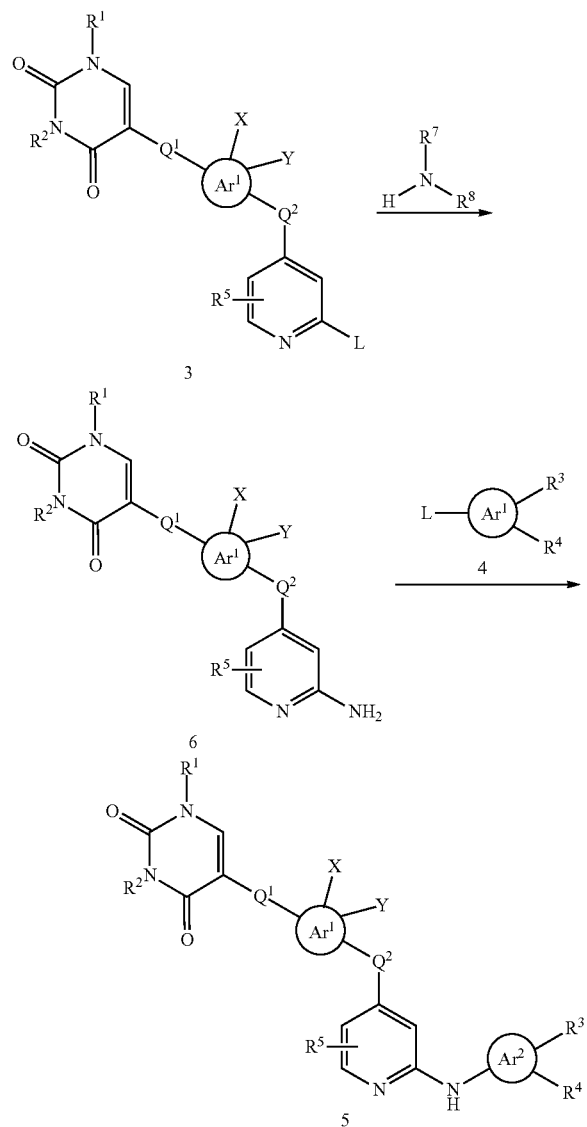

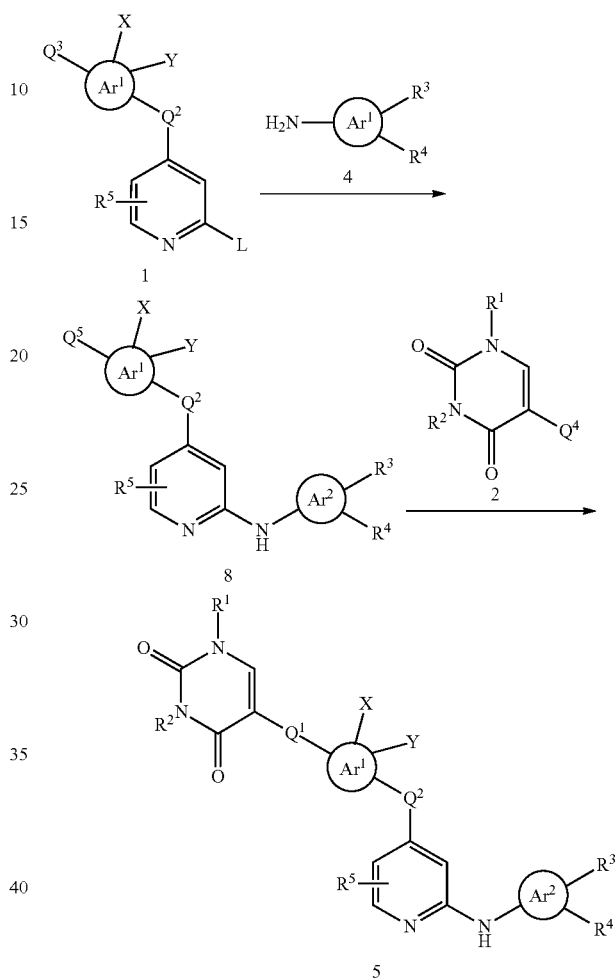

Biaryl amine 5 can be synthesized in many different ways such as that shown in Schemes 2 and 3. Suitably substituted halo- or hydroxypyridine 3 could be converted to aminopyridine 6, which can be reacted with a suitably substituted bromo-, chloro or tosyl-heteroarene 7 to provide biarylamine 5 using standard conditions such as Pd catalysis.

Alternately as shown in Scheme 3, substituted pyridine 1 can first be coupled with suitably substituted heteroarylamine 4 using standard N-arylation chemistry to afford birarylamines 8. If necessary, after functional group manipulation or deprotection, biarylamine 8 can be coupled with substituted uracils 2 to provide the desired diarylamines 5.

Substituted uracils 15 can be prepared in many different ways such as described in Schemes 4-6. For example, as shown in Scheme 4, aminomethylene malonates such as 9 can be treated with suitably substituted isocyanates 10 to afford ureidoemethylene malonates 11. Cyclization to the uracil 12 can be accomplished in a variety of means, such as treating 11 with base. Further functionalization of 12 can be accomplished through treatment with an appropriate alkylating agent, 13, where L is a suitable leaving group such as —Cl, —Br or —OTs, using standard conditions such as base and DMF.

Deprotection of 14, if necessary, provides the suitably substituted uracils 15 for use in the preparation of biaryl amines 5.

An alternate synthesis of substituted uracils 15 is shown in Scheme 5. In this illustration, alkoxymethylene malonates 16 are first reacted with a suitably substituted amines 17 to provide substituted aminomethylene malonates 18. Treatment with appropriately substituted isocyanates 10 utilizing standard conditions to effect ring closure provides the functionalized uracils 14. Like in the previous scheme, deprotection of 14, if necessary to liberate the carboxylic acid provides substituted uracils 15 for use in the preparation of biarylamines 5 as shown in Schemes 1-3.

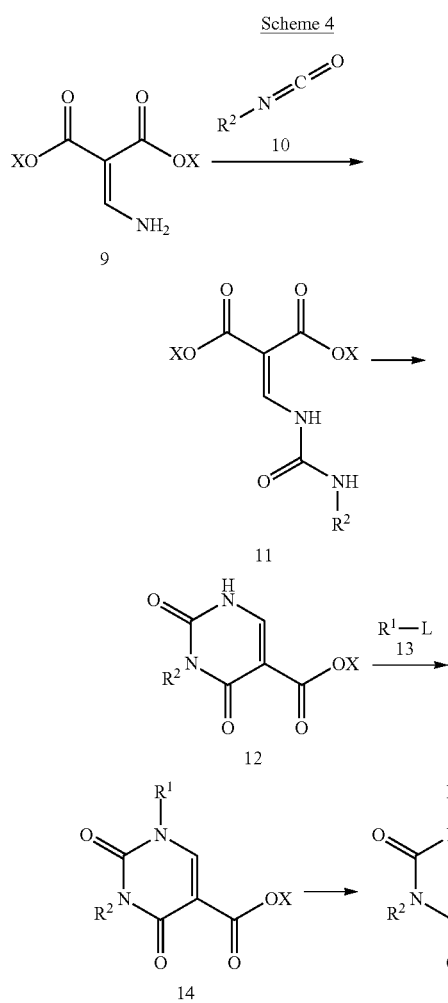

Scheme 4

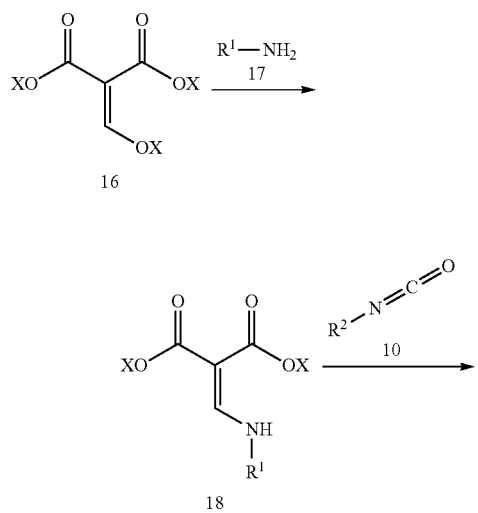

Scheme 5

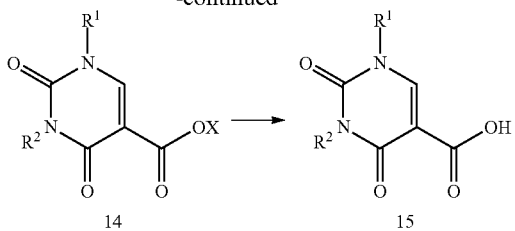

Another possible means of preparing uracil carboxylic acid is illustrated in Scheme 6. Appropriately substituted carbomylacrylates can be treated with primary amines 17 under standard conditions to affect ring closure, such as base and heat to provide substituted uracils 20. Installation of the $R^2$ group can be accomplished in a variety of means available to one skilled in the art, such as treatment with substituted boronic acids 21 utilizing an appropriate copper catalyst, or treatment with a suitably substituted alkylating reagent 22 where L is a suitable leaving group such as —Cl, —Br or —OTs, using standard conditions such as base and DMF. Like in the previous schemes, deprotection of 14, if necessary to liberate the carboxylic acid provides substituted uracils 15 for use in the preparation of biarylamines 5 as shown in Schemes 1-3.

Scheme 6

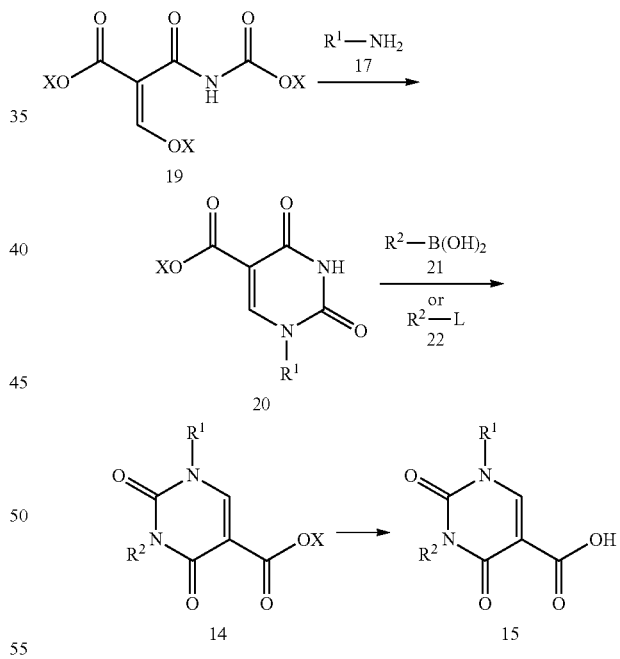

Examples

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

Abbreviations

| | |
|---|---|
| MeCN | Acetonitrile |
| AcOH | acetic acid |
| AlMe$_3$ | trimethyl aluminum |
| aq | Aqueous |
| Bn | Benzyl |
| Boc | tert-butoxycarbonyl |
| Boc$_2$O | di-tert-butyl dicarbonate |
| BOP | (Benzotriazol-1-yloxy)tris(dimethylamino)phosphonium hexafluorophosphate |
| Cbz | benzyloxycarbonyl |
| Cs$_2$CO$_3$ | Cesium carbonate |
| DCC | 1,3-dicyclohexylcarbodiimide |
| DCE | dichloroethane |
| DCM | dichloromethane |
| DDQ | 2,3-dichloro-5,6-dicyano-1,4-benzoquinone |
| DIAD | diisopropyl azodicarboxylate |
| DIEA | diisopropylethylamine |
| DMAP | 4-dimethylaminopyridine |
| DMA | dimethylacetamide |
| DME | dimethoxyethane |
| DMF | dimethylformamide |
| DMSO | dimethyl sulfoxide |
| EDC | 1-(3-dimethylaminopropyl)-3-ethylcarbodiimide hydrochloride |
| Et$_2$AlCl | diethyl aluminum chloride |
| Et$_3$N | triethyl amine |
| Et$_2$O | diethyl ether |
| EtOH | Ethanol |
| EtOAc | ethyl acetate |
| equiv | equivalent(s) |
| g | gram(s) |
| h or hr | hour(s) |
| HATU | 1-[Bis(dimethylamino)methylene]-1H-1,2,3-triazolo[4,5-b]pyridinium 3-oxid hexafluorophosphate, N-[(Dimethylamino)-1H-1,2,3-triazolo-[4,5-b]pyridin-1-ylmethylene]-N-methylmethanaminium hexafluorophosphate N-oxide |
| HOBt | hydroxybenzotriazole |
| HPLC | high pressure liquid chromatography |
| iPrOH | isopropyl alcohol |
| KOtBu | potassium tert-butoxide |
| LC/MS | Liquid Chromatography-Mass Spectrometry |
| LDA | lithium diisopropylamide |
| LiHMDS | lithium bis(trimethylsily)amide |
| Me | Methyl |
| MeI | methyl iodide |
| MeOH | Methanol |
| min | minute(s) |
| mL | milliliter(s) |
| mmol | Millimolar |
| MTBE | methyl t-butyl ether |
| NaHMDS | sodium bis(trimethylsilyl)amide |
| n-BuLi | n-butyl lithium |
| NH$_4$OAc | ammonium acetate |
| NMP | N-methylpyrrolidinone |
| Pd(OAc)$_2$ | palladium acetate |
| Pd$_2$(dba)$_3$ | Tris(dibenzylideneacetone)dipalladium(0) |
| Pd(dppf)Cl$_2$ | [1,1'-bis(diphenylphosphino)ferrocene]dichloropalladium(II) |
| RT or Rt | retention time |
| sat | Saturated |
| SFC | Supercritical fluid chromatography |
| t-Bu | tertiary butyl |
| t-BuLi | t-butyl lithium |
| t-BuOH | tertiary butyl alcohol |
| t-BuOMe | tert-butyl methyl ether |
| TBTU | O-(1H-benzotriazol-1-yl)-N,N,N',N'-tetramethyluronium tetrafluoroborate |
| TCTU | O-(1H-6-chlorobenzotriazol-1-yl)-N,N,N',N'-tetramethyluronium tetrafluoroborate |
| TEA | Triethylamine |
| TFA | trifluoroacetic acid |
| Tf$_2$O | trifluoromethylsulfonic anhydride |
| THF | Tetrahydrofuran |
| Xantphos | (9,9-dimethyl-9H-xanthene-4,5-diyl)bis(diphenylphosphane) |

The following HPLC conditions may be used where indicated:

Analytical HPLC Method 1; Column: Waters Acquity UPLC BEH C18, 2.1×50 mm, 1.7 μm particles; Mobile Phase A: water with 0.05% TFA; Mobile Phase B: acetonitrile 0.05% TFA; Gradient: 2-98% B over 1 min, then a 0.5-min hold at 98% B: Flow: 0.8 mL/min; Detection; UV at 254 nm.

Analytical HPLC Method 2; Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate: Gradient: 0-100% B over 3 min, then a 0.7-min hold at 100% B: Flow: 1.11 mL/min; Detection; UV at 254 nm.

LC/MS Method 1; Column: Phenomenex-Luna 2.0×30 mm, 3 um particles; Mobile Phase A: 10/90 methanol:water, 0.1% TFA; Mobile Phase B: 90/10 methanol:water, 0.1% TFA; Temperature 40° C.; Gradient 0%-100% B over 2 min; Flow 1 mL/min; Detection; UV at 220 nm.

LC/MS Method 2; Column: Waters Acquity SDS; Mobile Phase A: 100% Water, 0.1% TFA; Mobile Phase B: 100% acetonitrile, 0.1% TFA; Temperature 50° C.; Gradient 2%-98% B over 2.2 min; Flow 0.8 mL/min; Detection; UV at 220 nm.

LC/MS Method 3: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 min, then a 0.5-min hold at 100% B: Flow: 1 mL/min; Detection: UV at 220 nm.

LC/MS Method 4: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0%-100% B over 3 min, then a 0.5-min hold at 100% B; Flow: 0.5 mL/min; Detection: UV at 220 nm.

Preparative HPLC Method 1; Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate. Gradient: 30-70% B over 20 min, then a 5-min hold at 100% B; Flow: 20 mL/min.

Preparative HPLC Method 2; Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 20 min. then a 5-min hold at 100% B: Flow: 20 mL/min.

Preparative HPLC Method 3; Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 min, then a 5-min hold at 100% B: Flow: 20 mL/min.

Example 1

N-[4-({2-[(5-cyanopyridin-2-yl)amino]pyridin-4-yl}oxy)-3-fluorophenyl]-3-(4-fluorophenyl)-2,4-dioxo-1-(propan-2-yl)-1,2,3,4-tetrahydropyrimidine-5-carboxamide

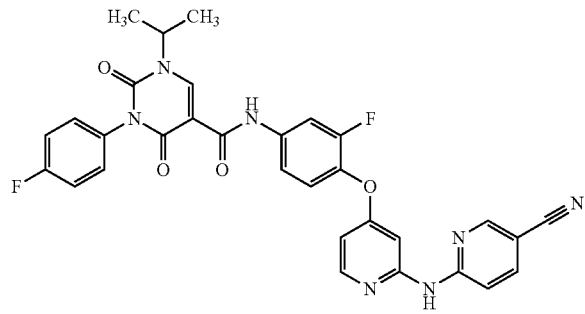 [SMILES: CC(C)n1cc(C(=O)Nc2ccc(Oc3ccnc(Nc4ccc(C#N)cn4)c3)c(F)c2)c(=O)n(-c2ccc(F)cc2)c1=O]

Step 1: Diethyl 2-((3-(4-fluorophenyl)ureido)methylene)malonate

Diethyl 2-(aminomethylene)malonate (1.5 g, 8.01 mmol, CombiBlocks) and 1-fluoro-4-isocyanatobenzene (0.957 ml, 8.41 mmol) were suspended in DCE (2.67 ml) at room temperature. DIPEA (1.539 ml, 8.81 mmol) was added followed by the dropwise addition of 1-fluoro-4-isocyanatobenzene (0.957 ml, 8.41 mmol). The reaction mixture was heated to 100° C. and stirred for 16 hr. The partially solidified reaction mixture was cooled to room temperature and diluted with 10 mL of 50% $Et_2O$—$CH_2Cl_2$. The remaining precipitate was filtered to afford diethyl 2-((3-(4-fluorophenyl)ureido) methylene)malonate as a cream solid (1.01 g). 1H NMR (400 MHz, DMSO-d6) δ 10.72-10.32 (m, 2H), 8.47 (br d, J=5.7 Hz, 1H), 7.61-7.43 (m, 2H), 7.26-6.99 (m, 2H), 4.24 (q, J=7.1 Hz, 2H), 4.15 (q, J=7.1 Hz, 2H), 1.26 (dt, J=12.0, 7.1 Hz, 6H); LC/MS (M+H) 325.2; LC RT=0.92 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min)

Step 2: Ethyl 3-(4-fluorophenyl)-2,4-dioxo-1,2,3,4-tetrahydropyrimidine-5-carboxylate To a suspension of diethyl 2-((3-(4-fluorophenyl)ureido) methylene)malonate (1.01 g, 3.11 mmol) in EtOH (6.23 mL) at room temperature was added sodium ethoxide solution (21% in EtOH) (1.860 ml, 4.98 mmol) dropwise. By the end of the addition, the reaction mixture was homogeneous. After stirring overnight, the reaction mixture was partitioned between EtOAc (20 mL) and 5% aq citric acid solution (20 mL). The aqueous layer was extracted with 2 additional portions of EtOAc (15 mL). The combined organic layer was washed with water and brine, dried over MgSO4 and concentrated to afford ethyl 3-(4-fluorophenyl)-2,4-dioxo-1,2,3,4-tetrahydropyrimidine-5-carboxylate as a cream solid (667.6 mg). 1H NMR (400 MHz, DMSO-d6) δ 12.02 (br d, J=1.6 Hz, 1H), 8.25 (s, 1H), 7.37-7.25 (m, 4H), 4.18 (q, J=7.1 Hz, 2H), 1.24 (t, J=7.1 Hz, 3H); LC/MS (M+H) 279.1; LC RT=0.62 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min)

Step 3: Ethyl 3-(4-fluorophenyl)-1-isopropyl-2,4-dioxo-1,2,3,4-tetrahydropyrimidine-5-carboxylate 2-Iodopropane (239 μl, 2.390 mmol) was added dropwise to a reaction vessel containing ethyl 3-(4-fluorophenyl)-2,4-dioxo-1,2,3,4-tetrahydropyrimidine-5-carboxylate (665 mg, 2.390 mmol) and potassium carbonate (661 mg, 4.78 mmol) in DMF (2.4 mL) and the reaction mixture was stirred at room temperature. After 16 h, the reaction mixture was partitioned between EtOAc and $H_2O$. The aqueous phase was extracted with 2 additional portions of EtOAc. The combined organics were washed with 10% aq LiCl solution, dried over $Na_2SO_4$ and concentrated to a amber glass which was triturated with a 50:50 $Et_2O$-hexane mixture to afford the named product as a cream solid (616 mg). 1H NMR (400 MHz, DMSO-d6) δ 8.45 (s, 1H), 7.44-7.22 (m, 4H), 4.71 (spt, J=6.6 Hz, 1H), 4.22 (q, J=7.1 Hz, 2H), 1.37 (d, J=6.7 Hz, 6H), 1.26 (t, J=7.1 Hz, 3H); LC/MS (M+H) 321.4; LC RT=0.79 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min)

Step 4: 3-(4-Fluorophenyl)-1-isopropyl-2,4-dioxo-1,2,3,4-tetrahydropyrimidine-5-carboxylic acid (Example 1, Intermediate A)

To a reaction vial containing ethyl 3-(4-fluorophenyl)-1-isopropyl-2,4-dioxo-1,2,3,4-tetrahydropyrimidine-5-carboxylate (616 mg, 1.923 mmol) was added 4N HCl (2212 μl, 8.85 mmol) and $H_2O$ (600 μL). The reaction to 70° C. for 16 h. The reaction was cooled to room temperature and $H_2O$ (1 mL) was added. The resulting white solid was collected by filtration to afford 3-(4-fluorophenyl)-1-isopropyl-2,4-dioxo-1,2,3,4-tetrahydropyrimidine-5-carboxylic acid (467 mg). $^1$H NMR (400 MHz, DMSO-d6) δ 12.68 (br s, 1H), 8.59 (s, 1H), 7.47-7.27 (m, 4H), 4.73 (quin, J=6.8 Hz, 1H), 1.39 (d, J=6.8 Hz, 6H); LC/MS (M+H) 293.1; LC RT=0.48 min (Column: BEH C18 2.1×50 mm; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 5-95% B over in 1 min; Flow: 0.8 mL/min).

Step 5: 2-chloro-4-(2-fluoro-4-nitrophenoxy)pyridine (Example 1, Intermediate B)

To a 100 mL round bottomed flask containing 2-chloropyridin-4-ol (6.11 g, 46.3 mmol) and $K_2CO_3$ (EMD, 12.8 g, 93.0 mmol) in DMF (46 mL) was added 1,2-difluoro-4-nitrobenzene (5.17 ml, 46.3 mmol). The reaction mixture was stirred at RT overnight. The reaction mixture was added slowly to a stirred solution of $H_2O$ (500 mL) and stirred for 30 min resulting in a tan precipitate. The solution was filtered and the precipitate was washed with $H_2O$ and hexanes and allowed to air dry for 30 min. The solid was then transferred to a flask with DCM and concentrated in vacuo to give the title compound (11.8 g, 95%) as a tan solid. $^1$H NMR (400 MHz, CHLOROFORM-d) δ 8.39-8.31 (m, 1H), 8.22-8.13 (m, 2H), 7.43-7.32 (m, 1H), 6.91 (d, J=2.3 Hz, 1H), 6.86 (dd, J=5.7, 2.2 Hz, 1H). LCMS (M+H)=269.1.

Step 6: 4-((2-chloropyridin-4-yl)oxy)-3-fluoroaniline (Example 1, Intermediate C)

To a 250 mL flask containing 2-chloro-4-(2-fluoro-4-nitrophenoxy)pyridine (5.00 g, 18.6 mmol, Intermediate B), ammonium chloride (6.97 g, 130 mmol) and EtOH (53 mL) was added zinc (8.52 g, 130 mmol). The reaction mixture was stirred under $N_2$ at 80° C. After 90 min the reaction mixture was cooled to RT and filtered through a 0.45 µM filter. The filtered solution was concentrated giving a tan oil. To the oil was added water and the solution was basicified with $NaHCO_3$, the crude product was sonicated until a cream powder formed. The solid was collected by filtration and air dried overnight to give the title compound (4.25 g, 96%) as a cream solid. $^1$H NMR (400 MHz, DMSO-d6) δ 8.27 (d, J=5.7 Hz, 1H), 7.02 (t, J=9.0 Hz, 1H), 6.94 (d, J=2.1 Hz, 1H), 6.91 (dd, J=5.7, 2.2 Hz, 1H), 6.52 (dd, J=13.2, 2.4 Hz, 1H), 6.43 (dd, J=8.7, 1.8 Hz, 1H), 5.52 (s, 2H). LCMS (M+H)=239.1

Step 7: N-(4-((2-chloropyridin-4-yl)oxy)-3-fluorophenyl)-3-(4-fluorophenyl)-1-isopropyl-2,4-dioxo-1,2,3,4-tetrahydropyrimidine-5-carboxamide To a solution of 4-((2-chloropyridin-4-yl)oxy)-3-fluoroaniline (1.143 g, 4.79 mmol, Example 1, Intermediate C) and 3-(4-fluorophenyl)-1-isopropyl-2,4-dioxo-1,2,3,4-tetrahydropyrimidine-5-carboxylic acid (1.4 g, 4.79 mmol, Example 1, Intermediate A) in NMP (15.97 mL) at room temperature, TEA (0.801 ml, 5.75 mmol) and HATU (2.186 g, 5.75 mmol) were added. The reaction was stirred at room temperature for 16 h. Water was added dropwise and the sticky solid was collected by filtration. Trituration with $Et_2O$ afforded the titled product (1.67 g, 68% yield) as a fine white powder. The filtrate was purified by column chromatography (24 g, $SiO_2$, 0 to 15% EtOAc—$CH_2Cl_2$ gradient elution) to provide additional material (0.37 g, 12%). $^1$H NMR (400 MHz, DMSO-d6) δ 11.04 (s, 1H), 8.68 (s, 1H), 8.31 (d, J=5.7 Hz, 1H), 8.00 (dd, J=13.0, 2.3 Hz, 1H), 7.52 (dd, J=8.9, 1.3 Hz, 1H), 7.48-7.25 (m, 5H), 7.09 (d, J=2.3 Hz, 1H), 6.99 (dd, J=5.7, 2.2 Hz, 1H), 4.91-4.69 (m, 1H), 1.43 (d, J=6.7 Hz, 6H); LC/MS (M+H) 513.4; HPLC RT=0.81 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 8: N-[4-({2-[(5-cyanopyridin-2-yl)amino]pyridin-4-yl}oxy)-3-fluorophenyl]-3-(4-fluorophenyl)-2,4-dioxo-1-(propan-2-yl)-1,2,3,4-tetrahydropyrimidine-5-carboxamide In a microwave reaction vial, N-(4-((2-chloropyridin-4-yl)oxy)-3-fluorophenyl)-3-(4-fluorophenyl)-1-isopropyl-2,4-dioxo-1,2,3,4-tetrahydropyrimidine-5-carboxamide (30 mg, 0.058 mmol), 6-aminonicotinonitrile (6.97 mg, 0.058 mmol), potassium carbonate (24.25 mg, 0.175 mmol) and BrettPhos Precatalyst G1 (4.67 mg, 5.85 µmol) were suspended in t-BuOH/DMA (6:1) (688 µl). The reaction was degassed with a stream of $N_2$ for 5 minutes, sealed and heated to 120° C. in the microwave reactor for 45 min. Upon cooling to room temperature, the reaction mixture was diluted with EtOAc, filtered through a PTFE frit and concentrated. The crude material was dissolved in DMF and purified by preparative LC/MS with the following conditions; Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate: Gradient: 45-90% B over 22 minutes, then a 5-minute hold at 100% B; Flow: 20 mL/min. Fractions containing the desired product were combined and dried via centrifugal evaporation to afford N-[4-({2-[(5-cyanopyridin-2-yl)amino]pyridin-4-yl}oxy)-3-fluorophenyl]-3-(4-fluorophenyl)-2,4-dioxo-1-(propan-2-yl)-1,2,3,4-tetrahydropyrimidine-5-carboxamide (11.3 mg, 32% yield). $^1$H NMR (500 MHz, DMSO-d$_6$) δ 11.01 (s, 1H), 10.31 (s, 1H), 8.65 (s, 1H), 8.56 (d, J=1.5 Hz, 1H), 8.19 (d, J=5.8 Hz, 1H), 8.02 (dd, J=9.0, 2.0 Hz, 1H), 7.97 (dd, J=12.8, 1.8 Hz, 1H), 7.84 (br d, J=8.9 Hz, 1H), 7.53-7.40 (m, 3H), 7.39-7.30 (m, 4H), 6.67-6.53 (m, 1H), 4.86-4.70 (m, 1H), 1.42 (br d, J=6.7 Hz, 6H); LC/MS (M+H)=596.16; HPLC RT=2.30 min (Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0 to 100% B over 3 min, then a 0.75 min hold at 100% B; Flow: 1 mL/min, UV Detection at 220 nm)

Examples 2-34

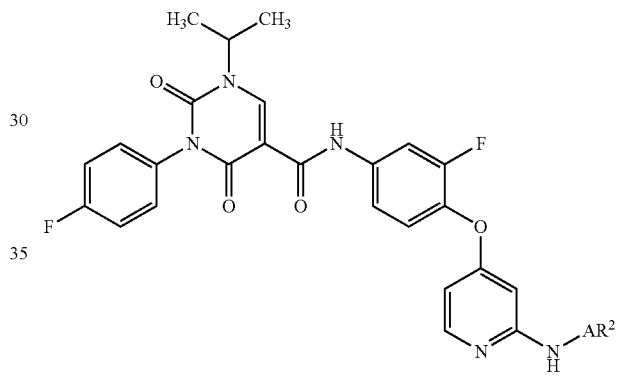

The compounds in Table 1 were prepared according to the procedures described for Example 1.

TABLE 1

| Ex. No. | Ar$^2$ | HPLC RT (min) | LC/MS (M + H) | HPLC Method |
|---|---|---|---|---|
| 2 | ![5-chloropyridin-2-yl] | 1.77 | 605.3 | A |
| 3 | ![3-fluoro-5-chloropyridin-2-yl] | 2.36 | 623.07 | A |
| 4 | ![5-methylpyridin-2-yl] | 1.81 | 585.2 | B |

TABLE 1-continued
| Ex. No. | Ar² | HPLC RT (min) | LC/MS (M + H) | HPLC Method |
|---|---|---|---|---|
| 5 | 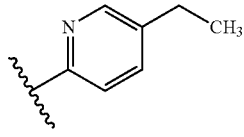 [SMILES: *c1ccc(CC)cn1] | 1.84 | 599.4 | B |
| 6 | 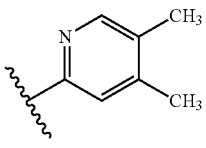 [SMILES: *c1cc(C)c(C)cn1] | 1.87 | 599.3 | B |
| 7 | 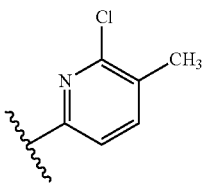 [SMILES: *c1ccc(C)c(Cl)n1] | 1.90 | 619.2 | B |
| 8 | 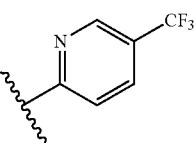 [SMILES: *c1ccc(C(F)(F)F)cn1] | 1.89 | 639.2 | B |
| 9 | 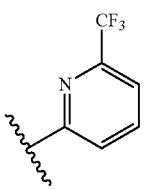 [SMILES: *c1cccc(C(F)(F)F)n1] | 1.90 | 639.3 | B |
| 10 | 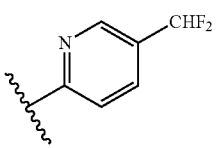 [SMILES: *c1ccc(C(F)F)cn1] | 1.82 | 621.2 | B |
| 11 | 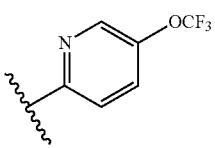 [SMILES: *c1ccc(OC(F)(F)F)cn1] | 2.03 | 655.3 | B |
| 12 | 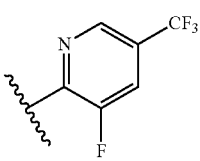 [SMILES: *c1ncc(C(F)(F)F)cc1F] | 1.90 | 657.3 | B |
| 13 | 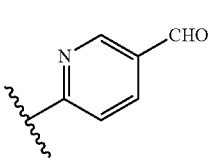 [SMILES: *c1ccc(C=O)cn1] | 1.81 | 585.2 | B |
| 14 | 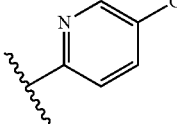 | 2.27 | 629.13 | A |
| 15 | 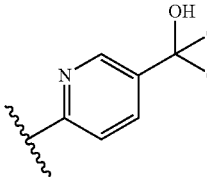 | 2.00 | 629.34 | A |
| 16 | 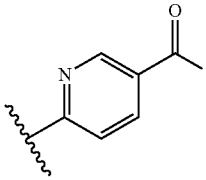 | 1.51 | 614.3 | B |
| 17 | 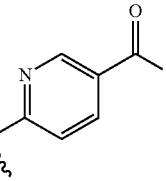 | 1.92 | 642.07 | A |
| 18 | 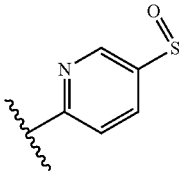 | 2.03 | 649.22 | A |
| 19 | 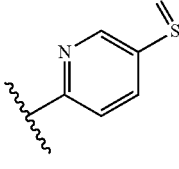 | 1.96 | 650.34 | A |
| 20 | 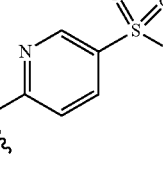 | 1.68 | 678.35 | A |
| 21 | 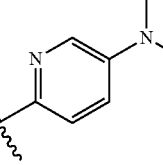 | 1.86 | 656.2 | B |

TABLE 1-continued

| Ex. No. | Ar² | HPLC RT (min) | LC/MS (M + H) | HPLC Method |
|---|---|---|---|---|
| 22 | pyridine-morpholine | 1.92 | 656.1 | B |
| 23 | pyridine-thiazole | 1.80 | 654.3 | B |
| 24 | pyridine-imidazole | 1.35 | 637.2 | B |
| 25 | 7-azaindole | 1.87 | 610.4 | B |
| 26 | pyrazine-CN | 1.72 | 597.2 | B |
| 27 | pyrazine-CH₃ | 1.60 | 586.0 | B |
| 28 | pyrazine-CH₂CH₃ | 1.74 | 600.3 | B |
| 29 | pyrazine-OEt | 1.81 | 616.3 | B |
| 30 | pyrimidine-CF₃ | 1.96 | 640.0 | B |
| 31 | pyrimidine-CH₃ | 1.78 | 586.2 | B |
| 32 | pyrimidine-CH₂CH₃ | 1.83 | 599.9 | B |
| 33 | thiazole-CH₂C(O)OCH₃ | 1.85 | 649.3 | B |
| 34 | thiadiazole-OCH₃ | 1.72 | 608.3 | B |

HPLC Conditions for Table 1:

Method A; Column: Waters XBridge C18, 2.1 mm×50 mm, 1.7 μm particles, Mobile Phase A: 5:95 acetonitrile:water with 10 mM ammonium acetate, Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: UV (220 nm).

Method B; Column: Waters XBridge C18, 2.1 mm×50 mm, 1.7 μm particles; Mobile Phase A: 5:95 acetonitrile:water with 0.1% trifluoroacetic acid. Mobile Phase B: 95:5 acetonitrile:water with 0.1% trifluoroacetic acid; Temperature: 50° C.; Gradient: 0% B to 100% B over 3 min, then a 0.75 min hold at 100% B, Flow: 1 mL/min; Detection: MS and UV (220 nm).

Example 35

N-{4-[(2-{[1-(Difluoromethyl)-1H-pyrazol-3-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide

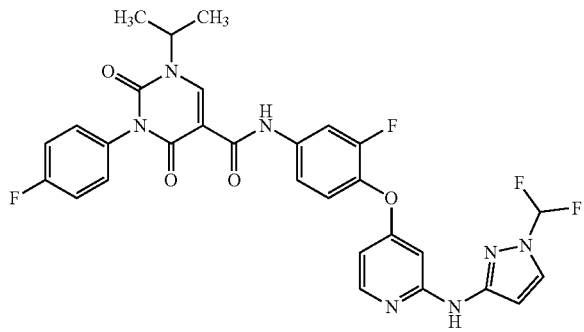 [SMILES: CC(C)n1cc(C(=O)Nc2ccc(Oc3ccnc(Nc4ccn(C(F)F)n4)c3)c(F)c2)c(=O)n(-c2ccc(F)cc2)c1=O]

Step 1: N-(1-(Difluoromethyl)-1H-pyrazol-3-yl)-4-(2-fluoro-4-nitrophenoxy)pyridin-2-amine 2-Chloro-4-(2-fluoro-4-nitrophenoxy)pyridine (881 mg, 3.28 mmol, Example 1, Intermediate B), 1-(difluoromethyl)-1H-pyrazol-3-amine, HCl (667 mg, 3.93 mmol), $Cs_2CO_3$ (3738 mg, 11.47 mmol), and BrettPhos (264 mg, 0.492 mmol) were suspended in dioxane (3.00 mL). The reaction mixture was purged with as stream of nitrogen for 1 min and $Pd_2(dba)_3$ (450 mg, 0.492 mmol) was added. The mixture was purged with nitrogen again and then heated to 105° C. for 3 h before cooling to room temperature. The reaction mixture was partitioned between brine (30 mL) and EtOAc (60 mL). The biphasic solution was filtered through celite, separated and then the aqueous phase was extracted with 2 additional portions of EtOAc (50 mL). The combined organics layers were washed with brine, dried over $Na_2SO_4$ and concentrated. Column chromatography (40 g SiO2, 0 to 10% MeOH—$CH_2Cl_2$, gradient elution) afforded N-(1-(difluoromethyl)-1H-pyrazol-3-yl)-4-(2-fluoro-4-nitrophenoxy)pyridin-2-amine (791 mg). 1H NMR (400 MHz, DMSO-d6) δ 9.81 (s, 1H), 8.42 (dd, J=10.5, 2.7 Hz, 1H), 8.22-8.17 (m, 1H), 8.16 (d, J=5.6 Hz, 1H), 8.01 (d, J=2.7 Hz, 1H), 7.62 (d, J=8.3 Hz, 1H), 7.59-7.53 (m, 1H), 7.16 (d, J=2.1 Hz, 1H), 6.57 (dd, J=5.7, 2.3 Hz, 1H), 6.49 (d, J=2.7 Hz, 1H); LC/MS: M+H=366.1: HPLC RT=0.70 min (Column: BEH C18 2.1×50 mm, 1.7µ; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 2: 4-(4-Amino-2-fluorophenoxy)-N-(1-(difluoromethyl)-1H-pyrazol-3-yl)pyridin-2-amine N-(1-(Difluoromethyl)-1H-pyrazol-3-yl)-4-(2-fluoro-4-nitrophenoxy)pyridin-2-amine (342 mg, 0.936 mmol) was suspended in a mixture of MeOH (10 mL) and DCM (3 mL). Ammonium chloride (601 mg, 11.24 mmol) was added followed by zinc (612 mg, 9.36 mmol). The reaction mixture was stirred for 16 h, diluted with 15 mL of EtOAc and filtered. Concentration of the filtrate afforded 4-(4-amino-2-fluorophenoxy)-N-(1-(difluoromethyl)-1H-pyrazol-3-yl)pyridin-2-amine (265 mg). LC/MS (M+H) 336.1; HPLC RT=0.62 min (Column: BEH C18 2.1×50 mm, 1.7µ; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 3: N-{4-[(2-{[1-(Difluoromethyl)-1H-pyrazol-3-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide 4-(4-Amino-2-fluorophenoxy)-N-(1-(difluoromethyl)-1H-pyrazol-3-yl)pyridin-2-amine (14 mg, 0.042 mmol) and 3-(4-fluorophenyl)-1-isopropyl-2,4-dioxo-1,2,3,4-tetrahydropyrimidine-5-carboxylic acid (12.20 mg, 0.042 mmol) were dissolved in DMF (418 µl) at rt. HATU (23.82 mg, 0.063 mmol) was added followed by DIPEA (21.88 µl, 0.125 mmol). The reaction mixture was stirred at rt for 4 h. The crude reaction mixture was diluted with DMF (0.5 mL) and directly purified by preparative LCMS with the following conditions; Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 4-minute hold at 100% B: Flow: 20 mL/min. Fractions containing the desired product were combined and dried via centrifugal evaporation to afford N-{4-[(2-{[1-(difluoromethyl)-1H-pyrazol-3-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide (5.3 mg). 1H NMR (500 MHz, DMSO-d6) δ 10.99 (s, 1H), 9.60 (s, 1H), 8.63 (s, 1H), 8.06 (d, J=5.8 Hz, 1H), 7.99-7.85 (m, 2H), 7.66-7.26 (m, 7H), 7.03 (s, 1H), 6.48 (d, J=2.4 Hz, 1H), 6.41 (dd, J=5.5, 1.8 Hz, 1H), 4.76 (dt, J=13.5, 6.8 Hz, 1H), 1.41 (br d, J=6.7 Hz, 6H); LC/MS (M+H)=610.25; HPLC RT=2.05 min (Column: Waters XBridge C18, 2.1 mm×50 mm, 1.7 µm particles; Mobile Phase A: 5:95 acetonitrile:water with 10 mM ammonium acetate; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0 to 100% B over 3 min, then a 0.75 min hold at 100% B: Flow: 1 mL/min, UV Detection at 220 nm)

Example 36

N-[4-({2-[(5-chloropyridin-2-yl)amino]pyridin-4-yl}oxy)-3-fluorophenyl]-1-cyclopropyl-3-(4-fluorophenyl)-2,4-dioxo-1,2,3,4-tetrahydropyrimidine-5-carboxamide

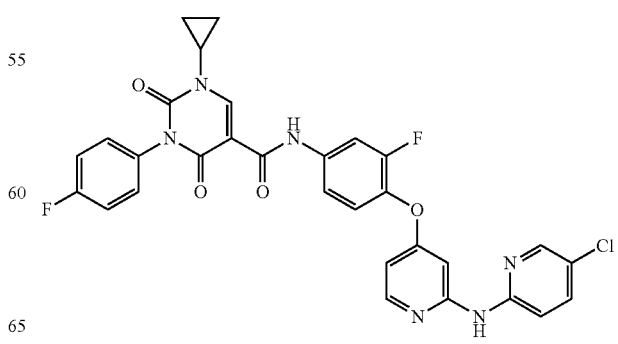

Step 1: Diethyl 2-((cyclopropylamino)methylene)malonate

To a 40 mL vial containing cyclopropanamine (Matrix, 1.0 g, 17.7 mmol) cooled in an ice/water bath was added dropwise diethyl 2-(ethoxymethylene)malonate (3.5 mL, 17.7 mmol) over an 11 minute period. The reaction was stirred at room temperature for 30 min and then concentrated under vacuum to give the title compound (4.0 g, 100%) as a pale yellow oil. $^1$H NMR (400 MHz, DMSO-d6) δ 9.07 (br d, J=13.7 Hz, 1H), 7.99 (d, J=14.3 Hz, 1H), 4.13-4.07 (m, 2H), 4.07-4.00 (m, 2H), 3.00 (tq, J=7.1, 3.7 Hz, 1H), 1.19 (td, J=7.1, 2.1 Hz, 6H), 0.78-0.67 (m, 4H); LCMS (M+H) =228. HPLC RT=1.60 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.: Gradient: 0-100% B over 4 min; Flow: 4 mL/min).

Step 2: Ethyl 1-cyclopropyl-3-(4-fluorophenyl)-2,4-dioxo-1,2,3,4-tetrahydropyrimidine-5-carboxylate To a 20 mL vial containing diethyl 2-((cyclopropylamino)methylene)malonate (1.0 g, 4.4 mmol) and 1-fluoro-4-isocyanatobenzene (Aldrich, 0.52 mL, 4.6 mmol) in dioxane (5 mL) was added KOtBu (0.5 g, 4.4 mmol). The reaction was stirred at room temperature 18 hours and acidified with 1M aqueous citric acid solution, diluted with water and extracted with Et$_2$O. The organic layer was concentrated under vacuum and the crude material purified by silica gel chromatography (80 g SiO$_2$, 0 to 30% EtOAc—CH$_2$Cl$_2$ gradient elution). The product was collected and concentrated to give the title compound (0.591 g, 41%) as a white solid. $^1$H NMR (400 MHz, DMSO-d6) δ 8.29 (s, 1H), 7.36-7.24 (m, 4H), 4.20 (q, J=7.1 Hz, 2H), 3.24-3.15 (m, 1H), 1.24 (t, J=7.1 Hz, 3H), 1.01-0.92 (m, 4H); LCMS (M+H)=319.0; HPLC RT=1.23 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.: Gradient: 0-100% B over 4 min; Flow: 4 mL/min).

Step 3: 1-Cyclopropyl-3-(4-fluorophenyl)-2,4-dioxo-1,2,3,4-tetrahydropyrimidine-5-carboxylic acid To a 40 mL vial containing ethyl 1-cyclopropyl-3-(4-fluorophenyl)-2,4-dioxo-1,2,3,4-tetrahydropyrimidine-5-carboxylate (0.591 g, 1.85 mmol) in THF (3 mL) was added NaOH (1M aq, 2.79 mL, 2.79 mmol). The reaction was stirred at room temperature 1 hour and acidified with 1M aqueous HCl solution, diluted with water and extracted with CH$_2$Cl$_2$. The organic layer was concentrated under vacuum and the crude material purified by silica gel chromatography (24 g SiO$_2$, 0 to 100% EtOAc—CH$_2$Cl$_2$). The product was collected and concentrated to give the title compound (0.24 g, 44%) as a white solid. $^1$H NMR (400 MHz, DMSO-d6) δ 12.76-12.44 (m, 1H), 8.40 (s, 1H), 7.33 (d, J=6.8 Hz, 4H), 3.26-3.19 (m, 1H), 1.01-0.96 (m, 4H); LCMS (M+H)=291.0; HPLC RT=0.842 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: N-(4-((2-chloropyridin-4-yl)oxy)-3-fluorophenyl)-1-cyclopropyl-3-(4-fluorophenyl)-2,4-dioxo-1,2,3,4-tetrahydropyrimidine-5-carboxamide To a 4 mL vial containing 1-cyclopropyl-3-(4-fluorophenyl)-2,4-dioxo-1,2,3,4-tetrahydropyrimidine-5-carboxylic acid (0.02 g, 0.069 mmol), 4-((2-chloropyridin-4-yl)oxy)-3-fluoroaniline (0.016 g, 0.069 mmol, Example 1, Intermediate C) and Et$_3$N (0.012 mL, 0.083 mmol) in NMP (0.5 mL) was added HATU (0.031 g, 0.083 mmol). The reaction was stirred at room temperature for 4 hours and diluted with water and saturated aqueous NaHCO$_3$ solution. The white precipitate that formed was collected by filtration, rinsed with water and dried under vacuum to give the title compound (0.03 g, 85%) as a white solid. $^1$H NMR (500 MHz, DMSO-d6) δ 10.98 (s, 1H), 8.51 (s, 1H), 8.30 (d, J=5.8 Hz, 1H), 7.98 (dd, J=12.9, 2.4 Hz, 1H), 7.52 (dd, J=8.9, 1.4 Hz, 1H), 7.43-7.34 (m, 5H), 7.08 (d, J=2.1 Hz, 1H), 6.98 (dd, J=5.7, 2.2 Hz, 1H), 3.31-3.25 (m, 1H), 1.06-0.99 (m, 4H); LCMS (M+H)=511. HPLC RT=2.775 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 5. N-[4-({2-[(5-chloropyridin-2-yl)amino]pyridin-4-yl}oxy)-3-fluorophenyl]-1-cyclopropyl-3-(4-fluorophenyl)-2,4-dioxo-1,2,3,4-tetrahydropyrimidine-5-carboxamide In a 4 mL vial, N-(4-((2-chloropyridin-4-yl)oxy)-3-fluorophenyl)-1-cyclopropyl-3-(4-fluorophenyl)-2,4-dioxo-1,2,3,4-tetrahydropyrimidine-5-carboxamide (15 mg, 0.029 mmol), 5-chloropyridin-2-amine (5.66 mg, 0.044 mmol), Xantphos (2.04 mg, 3.52 μmol), Pd$_2$dba$_3$ (2.69 mg, 2.94 μmol) and Cs$_2$CO$_3$ (28.7 mg, 0.088 mmol) were suspended in dioxane (0.5 mL) and flushed with N$_2$. The reaction was heated to 110° C. for 2 hours, then cooled to rt, diluted with THF and filtered through a 0.45 μm membrane. The reaction mixture was concentrated and the crude material was purified via preparative LC/MS with the following conditions; Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 19 minutes, then a 5-minute hold at 100% B; Flow: 20 mL/min. Fractions containing the desired product were combined and dried via centrifugal evaporation to give the title compound (7.4 mg, 36.5%). $^1$H NMR (500 MHz, DMSO-d) δ 10.96 (s, 1H), 8.51 (s, 1H), 8.19 (s, 1H), 8.15 (br d, J=5.8 Hz, 1H), 7.97 (br d, J=13.4 Hz, 1H), 7.78 (br d, J=7.3 Hz, 1H), 7.70 (br d, J=8.5 Hz, 1H), 7.51 (br d, J=8.5 Hz, 1H), 7.43-7.33 (m, 5H), 7.14 (br s, 1H), 6.59 (br d, J=3.7 Hz, 1H), 1.07-0.96 (m, 4H); LCMS (M+H)=603.2; HPLC RT=2.27 min (Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.: Gradient: 0% B to 100% B over 3 min, then a 0.75 min hold at 100% B; Flow: 1 mL/min; Detection UV 220 nm).

Example 37

N-[3-Fluoro-4-({2-[(5-methanesulfonylpyridin-2-yl)amino]pyridin-4-yl}oxy)phenyl]-3-(5-fluoropyridin-2-yl)-2,4-dioxo-1-(propan-2-yl)-1,2,3,4-tetrahydropyrimidine-5-carboxamide

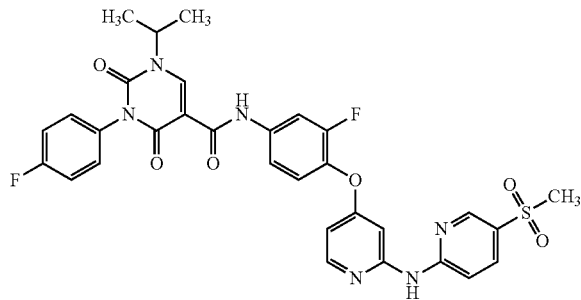 [SMILES: CC(C)n1cc(C(=O)Nc2ccc(Oc3ccnc(Nc4ccc(S(C)(=O)=O)cn4)c3)c(F)c2)c(=O)n(-c2ccc(F)cc2)c1=O]

Step 1: Diethyl 2-((isopropylamino)methylene)malonate

To a 40 mL vial containing propan-2-amine (Matrix, 4 mL, 24.4 mmol) cooled in an ice/water bath was added dropwise diethyl 2-(ethoxymethylene)malonate (4.94 mL, 24.4 mmol) over a 5 minute period. The reaction was stirred at room temperature for 1 hour and then concentrated under vacuum to give the title compound (5.5 g, 100%) as a pale yellow oil. $^1$H NMR (400 MHz, DMSO-d$_6$) δ 9.09 (br dd, J=14.2, 7.6 Hz, 1H), 8.03 (d, J=14.4 Hz, 1H), 4.10 (q, J=7.1 Hz, 2H), 4.04 (q, J=7.0 Hz, 2H), 3.80-3.65 (m, 1H), 1.25-1.16 (m, 12H); LCMS (M+H)=230; HPLC RT=1.638 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.: Gradient: 0-100% B over 4 min; Flow: 4 mL/min).

Step 2: Ethyl 3-(5-fluoropyridin-2-yl)-1-isopropyl-2,4-dioxo-1,2,3,4-tetrahydropyrimidine-5-carboxylate To a 20 mL vial containing diethyl 2-((isopropylamino)methylene)malonate (388 mg, 1.69 mmol) and 5-fluoro-2-isocyanatopyridine (257 mg, 1.86 mmol) in dioxane (6 mL) was added KOtBu (190 mg, 1.69 mmol). The reaction was stirred at room temperature 1 hour, then acidified with 1M aqueous citric acid solution to pH 4, diluted with water and extracted with CHCl$_3$ (2×). The combined organic layer was concentrated under vacuum and the crude material purified by silica gel chromatography (40 g SiO$_2$, 0 to 100% EtOAc—CH$_2$Cl$_2$ gradient elution). The product was collected and concentrated to give the title compound (190.9 mg, 35.1%) as a white solid. 1H NMR (500 MHz, DMSO-d6) δ 8.60 (d, J=3.1 Hz, 1H), 8.49 (s, 1H), 7.96 (td, J=8.5, 3.1 Hz, 1H), 7.56 (dd, J=8.7, 4.1 Hz, 1H), 4.69 (spt, J=6.8 Hz, 1H), 4.22 (q, J=7.2 Hz, 2H), 1.38 (d, J=6.7 Hz, 6H), 1.25 (t, J=7.1 Hz, 3H); LCMS (M+H)=322.0; HPLC RT=1.085 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.: Gradient: 0-100% B over 4 min; Flow: 4 mL/min).

Step 3: 3-(5-Fluoropyridin-2-yl)-1-isopropyl-2,4-dioxo-1,2,3,4-tetrahydropyrimidine-5-carboxylic acid, HCl To a 8 mL vial containing ethyl 3-(5-fluoropyridin-2-yl)-1-isopropyl-2,4-dioxo-1,2,3,4-tetrahydropyrimidine-5-carboxylate (190.9 mg, 0.59 mmol) was added HCl (4M in dioxane, 891 µL) and water (150 µL). The reaction mixture was heated to 70° C. for 18 hours, then cooled to room temperature. The reaction was concentrated and dried under vacuum to give the title compound (185.6 mg, 95%) as an off-white solid. HPLC RT=0.678 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: 4-(2-fluoro-4-nitrophenoxy)-N-(5-(methylsulfonyl)pyridin-2-amine

In a 8 mL vial containing 2-chloro-4-(2-fluoro-4-nitrophenoxy)pyridine (60 mg, 0.223 mmol. Example 1, Intermediate B), 5-(methylsulfonyl)pyridin-2-amine (50.0 mg, 0.290 mmol), Xantphos (15.51 mg, 0.027 mmol), Pd$_2$dba$_3$ (20.45 mg, 0.022 mmol) and Cs$_2$CO$_3$ (218 mg, 0.670 mmol) was added dioxane (2 mL). The reaction mixture was flushed with N$_2$, sealed and heated to 110° C. for 3 h. After cooling to rt, the reaction mixture was diluted with CHCl$_3$, filtered and concentrated. Column chromatography (12 g SiO$_2$, 0 to 100% EtOAc—CH$_2$Cl$_2$) afforded the desired material (83.2 mg 92% yield). LC/MS (M+H) 405.0; HPLC RT 0.53 min; Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Step 5: 4-(4-Amino-2-fluorophenoxy)-N-(5-(methylsulfonyl)pyridin-2-yl)pyridin-2-amine To a 8 mL vial containing 4-(2-fluoro-4-nitrophenoxy)-N-(5-(methylsulfonyl)pyridin-2-yl)pyridin-2-amine (83 mg, 0.205 mmol), zinc (107 mg, 1.642 mmol), and ammonium chloride (88 mg, 1.642 mmol), Ethanol (2 mL) was added to give a grey suspension. The reaction was heated to 80° C. for 90 minutes before cooling to rt and filtering through a 0.45 µm membrane. After concentrated, the crude material was diluted with H$_2$O and treated with sat. aq. NaHCO$_3$ until pH 9. The resulting white precipitate was collected by filtration and dried under vacuum (36.4 mg, 47% yield). LC/MS (M+H) 375.0; HPLC RT 0.39 min; Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100%

B over 3 min, then a 0.75 min hold at 100% B: Flow: 1 mL/min; Detection: MS and UV (220 nm).

Step 6: N-[3-fluoro-4-({2-[(5-methanesulfonylpyridin-2-yl)amino]pyridin-4-yl}oxy)phenyl]-3-(5-fluoropyridin-2-yl)-2,4-dioxo-1-(propan-2-yl)-1,2,3,4-tetrahydropyrimidine-5-carboxamide To a 4 mL vial containing 3-(5-fluoropyridin-2-yl)-1-isopropyl-2,4-dioxo-1,2,3,4-tetrahydropyrimidine-5-carboxylic acid, HCl (12.59 mg, 0.038 mmol), 4-(4-amino-2-fluorophenoxy)-N-(5-(methylsulfonyl)pyridin-2-yl)pyridin-2-amine (13 mg, 0.035 mmol) and Et$_3$N (15 μL, 0.104 mmol) in NMP (0.3 mL) was added HATU (17.16 mg, 0.045 mmol). The reaction was stirred at room temperature for 4 hours, then purified via preparative LC/MS with the following conditions; Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-68% B over 20 minutes, then a 4-minute hold at 100% B; Flow: 20 mL/min. Fractions containing the desired product were combined and dried via centrifugal evaporation to give the title compound (10.0 mg, 44.3%). $^1$H NMR (500 MHz, DMSO-d6) δ 10.79 (s, 1H), 10.24 (br s, 1H), 8.68 (s, 1H), 8.63 (br s, 1H), 8.58 (br s, 1H), 8.19 (d, J=5.7 Hz, 1H), 8.07 (br d, J=9.0 Hz, 1H), 8.02-7.87 (m, 3H), 7.65 (br dd, J=8.3, 4.0 Hz, 1H), 7.47 (br d, J=8.1 Hz, 1H), 7.38-7.30 (m, 2H), 6.60 (dd, J=5.6, 1.7 Hz, 1H), 4.80-4.73 (m, 1H), 3.25-3.15 (m, 3H), 1.44 (br d, J=6.6 Hz, 6H); LCMS (M+H)+=650.09; HPLC RT=1.80 min (Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.: Gradient: 0% B to 100% B over 3 min, then a 0.75 min hold at 100% B; Flow: 1 mL/min; Detection UV 220 nm).

Examples 38-39

The compounds in Table 2 were prepared according to the procedures described for Example 37.

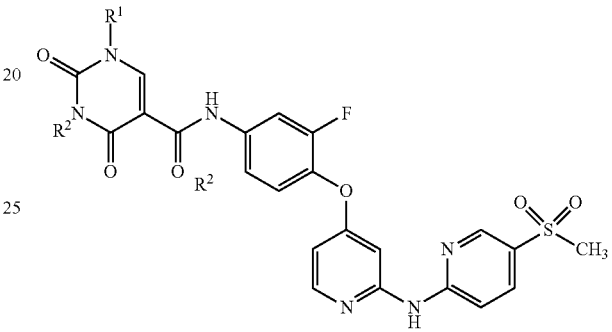

TABLE 2

| Ex. No. | R$^1$ | R$^2$ | HPLC RT (min) | LC/MS (M + H) | HPLC Method |
|---|---|---|---|---|---|
| 38 | CH$_3$ | 4-fluorophenyl | 1.44 | 621.0 | A |
| 39 | H$_3$C⋯CH(CH$_2$OH) | 4-fluorophenyl | 1.87 | 665.3 | A |

HPLC Conditions for Table 2:

Method A; Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: UV (220 nm).

Example 40

1-Cyclopropyl-N-{4-[(2-{[5-(dimethylsulfamoyl)pyridin-2-yl]amino}pyridin-4-yl)oxy]-3-fluorophenyl}-3-(4-fluorophenyl)-2,4-dioxo-1,2,3,4-tetrahydropyrimidine-5-carboxamide

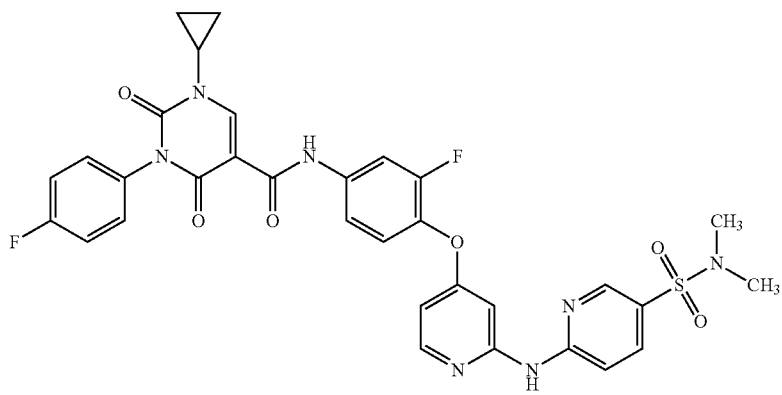 [SMILES: CN(C)S(=O)(=O)c1ccc(Nc2cc(Oc3ccc(NC(=O)c4cn(C5CC5)c(=O)n(-c5ccc(F)cc5)c4=O)cc3F)ccn2)nc1]

Step 1: 1-Cyclopropyl-N-{4-[(2-{[5-(dimethylsulfamoyl)pyridin-2-yl]amino}pyridin-4-yl)oxy]-3-fluorophenyl}-3-(4-fluorophenyl)-2,4-dioxo-1,2,3,4-tetrahydropyrimidine-5-carboxamide To a 4 mL vial containing N-(4-((2-chloropyridin-4-yl)oxy)-3-fluorophenyl)-1-cyclopropyl-3-(4-fluorophenyl)-2,4-dioxo-1,2,3,4-tetrahydropyrimidine-5-carboxamide (30 mg, 0.059 mmol, Example 36—Step 4), 6-amino-N,N-dimethylpyridine-3-sulfonamide (17.7 mg, 0.088 mmol), Xantphos (4.1 mg, 7.1 umol), Pd$_2$dba$_3$ (5.4 mg, 5.8 umol) and Cs$_2$CO$_3$ (57.4 mg, 0.176 mmol) in dioxane (0.5 mL). The reaction was heated to 110° C. for 2 hours, cooled to rt, diluted with CH$_2$Cl$_2$ and filtered through a 0.45 μm membrane. The reaction mixture was concentrated and the crude material was purified via preparative LC/MS with the following conditions; Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate: Gradient: 35-75% B over 20 minutes, then a 6-minute hold at 100% B; Flow: 20 mL/min. Fractions containing the desired product were combined and dried via centrifugal evaporation to give the title compound (10.7 mg, 26.4%). $^1$H NMR (500 MHz, DMSO-d6) δ 10.95 (br s, 1H), 8.50 (s, 1H), 8.44 (br s, 1H), 8.18 (br s, 1H), 7.94 (br t, J=9.9 Hz., 3H), 7.47 (br d, J=7.9 Hz, 1H), 7.41-7.30 (m, 6H), 6.58 (br s, 1H), 3.33-3.23 (m, 1H), 2.60 (s, 6H), 1.06-0.98 (m, 4H); LCMS (M+H)+ =676.3; HPLC RT=1.78 min (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.: Gradient: 0% B to 100% B over 3 min, then a 0.75 min hold at 100% B; Flow: 1 mL/min; Detection UV 220 nm).

Example 41

N-{4-[(2-{[5-(dimethylsulfamoyl)pyridin-2-yl]amino}pyridin-4-yl)oxy]-3-fluorophenyl}-2,4-dioxo-1-(propan-2-yl)-3-{[2-(trifluoromethyl)phenyl]methyl}-1,2,3,4-tetrahydropyrimidine-5-carboxamide

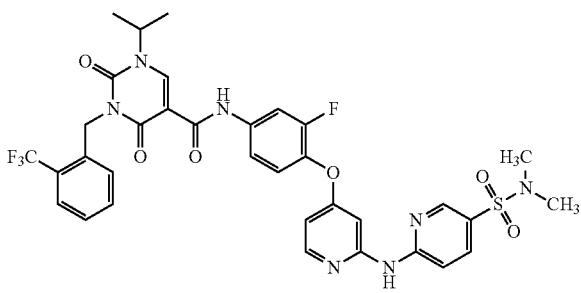 [SMILES: CC(C)n1cc(C(=O)Nc2ccc(Oc3ccnc(Nc4ccc(S(=O)(=O)N(C)C)cn4)c3)c(F)c2)c(=O)n(Cc2ccccc2C(F)(F)F)c1=O]

Step 1: Ethyl 2,4-dioxo-3-(2-(trifluoromethyl)benzyl)-1,2,3,4-tetrahydropyrimidine-5-carboxylate An oven dried two neck flask was charged with 2-(2-(trifluoromethyl)phenyl)acetic acid (0.5 g, 2.449 mmol) under nitrogen. The starting material was suspended in dioxane (5 mL). Diisopropylethylamine (0.856 ml, 4.90 mmol) was added and a homogeneous solution was obtained. Reaction was initiated with the addition of diphenylphosphoryl azide (0.582 ml, 2.69 mmol). After stirring for 0.5 hour, the reaction was warmed to 100° C. behind a blast shield. A controlled evolution of gas began around 65° C. and was complete in about 45 minutes. The reaction was cooled and diethyl 2-(aminomethylene)malonate (0.458 g, 2.449 mmol) was added. The reaction was then warmed to 100° C. and stirred overnight. The cooled reaction was applied to an 80 g Isco silica gel column and eluted with 0-5% methanol in methylene chloride. This treatment provided a mixture of the desired product and starting material (498 mg). This material was taken into cyclization step without additional purification. The partially purified material was dissolved in ethanol (5 mL) under nitrogen. A solution of sodium ethoxide in ethanol (760 µl, 2.052 mmol) was added and stirring continued for an hour. The reaction was then quenched with 5% aqueous citric acid solution. The resultant precipitate was filtered and sequentially rinsed with water and hexanes. Air drying provided ethyl 2,4-dioxo-3-(2-(trifluoromethyl)benzyl)-1,2,3,4-tetrahydropyrimidine-5-carboxylate (44.3 mg, 0.129 mmol, 10% yield). $^1$H NMR (400 MHz, DMSO-d6) δ 12.13 (br s, 1H), 8.30 (s, 1H), 7.77 (d, J=7.9 Hz, 1H), 7.59 (t, J=8.3 Hz, 1H), 7.48 (t, J=7.7 Hz, 1H), 7.12 (d, J=7.6 Hz, 1H), 5.14 (s, 2H), 4.19 (q, J=7.1 Hz, 2H), 1.25 (t, J=7.1 Hz, 4H); LCMS (M+H)=343.0. HPLC RT=0.81 min (Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA).

Step 2: Ethyl 1-isopropyl-2,4-dioxo-3-(2-(trifluoromethyl)benzyl)-1,2,3,4-tetrahydropyrimidine-5-carboxylate Ethyl 2,4-dioxo-3-(2-(trifluoromethyl)benzyl)-1,2,3,4-tetrahydropyrimidine-5-carboxylate (44 mg, 0.129 mmol) was dissolved in DMF (1 mL) under nitrogen. Potassium carbonate (35.5 mg, 0.257 mmol) and 2-iodopropane (25.7 µl, 0.257 mmol) were added and the reaction warmed to 70° C. After 3 hours, the reaction was cooled and stirred over the weekend. Water was added and after a few minutes of stirring, a nice solid formed. The solid was filtered and rinsed sequentially with water then hexanes. Air drying gave ethyl 1-isopropyl-2,4-dioxo-3-(2-(trifluoromethyl)benzyl)-1,2,3,4-tetrahydropyrimidine-5-carboxylate (19.2 mg, 0.050 mmol, 38.9% yield). $^1$H NMR (400 MHz, DMSO-d6) δ 8.48 (s, 1H), 7.77 (d, J=7.9 Hz, 1H), 7.59 (t, J=7.8 Hz, 1H), 7.48 (t, J=7.3 Hz, 1H), 7.13 (d, J=7.9 Hz, 1H), 5.18 (s, 2H), 4.72 (dt, J=13.6, 6.6 Hz, 1H), 4.23 (q, J=7.0 Hz, 2H), 1.38 (d, J=6.7 Hz, 6H), 1.26 (t, J=7.1 Hz, 3H); LCMS (M+H)=385.4. HPLC RT=0.96 min (Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 1000% Acetonitrile, 0.05% TFA).

Step 3: 1-isopropyl-2,4-dioxo-3-(2-(trifluoromethyl)benzyl)-1,2,3,4-tetrahydropyrimidine-5-carboxylic acid Ethyl 1-isopropyl-2,4-dioxo-3-(2-(trifluoromethyl)benzyl)-1,2,3,4-tetrahydropyrimidine-5-carboxylate (19.2 mg, 0.050 mmol) was dissolved in HCl (200 µl, 0.800 mmol) (4 M in dioxane). Water (40 µL) was added and the reaction was warmed to 70° C. for 2 hours. The cooled reaction was diluted with water and stirred to give a precipitate. The solid was filtered and rinsed sequentially with water and hexanes. Air drying provide 1-isopropyl-2,4-dioxo-3-(2-(trifluoromethyl)benzyl)-1,2,3,4-tetrahydropyrimidine-5-carboxylic acid (7.2 mg, 0.020 mmol, 40.5% yield). $^1$H NMR (400 MHz, DMSO-d6) δ 12.80-12.55 (m, 1H), 8.58 (s, 1H), 7.78 (d, J=7.9 Hz, 1H), 7.68-7.53 (m, 1H), 7.54-7.40 (m, 1H), 7.20 (d, J=7.8 Hz, 1H), 5.21 (s, 2H), 4.74 (spt, J=6.9 Hz, 1H), 1.39 (d, J=6.7 Hz, 6H); LCMS (M+H)=357.3. HPLC RT=0.96 min (Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA).

Step 4: 6-((4-(2-Fluoro-4-nitrophenoxy)pyridin-2-yl)amino)-N,N-dimethylpyridine-3-sulfonamide 6-Amino-N,N-dimethylpyridine-3-sulfonamide (200 mg, 0.994 mmol), 2-chloro-4-(2-fluoro-4-nitrophenoxy)pyridine (222 mg, 0.828 mmol, Intermediate B), $Cs_2CO_3$ (944 mg, 2.90 mmol), and BrettPhos (66.7 mg, 0.124 mmol) were combined in dioxane (7.50 mL). The reaction mixture was purged with nitrogen for 1 min and $Pd_2(dba)_3$ (114 mg, 0.124 mmol) was added. After heating to 105° C. for 2 hours, the reaction was cooled to rt and partitioned between brine (30 mL) and EtOAc (50 mL). The organic layer was separated and the aqueous phase was extracted with 2 additional portions of EtOAc (2×50 mL). The combined organic phases were combined, dried over $Na_2SO_4$ and concentrated. Column chromatography (40 g $SiO2$, 0 to 100% EtOAc—$CH_2Cl_2$) afforded the expected product (125 mg, 35% yield). LCMS (M+H)=434.1. HPLC RT=1.523 min (Chromolith SpeedROD column 4.6×50 mm, 10-90% aqueous methanol over 4 minutes containing 0.1% TFA, 4 mL/min, monitoring at 220 nm).

Step 5: 6-((4-(4-amino-2-fluorophenoxy)pyridin-2-yl)amino)-N,N-dimethylpyridine-3-sulfonamide 6-((4-(2-fluoro-4-nitrophenoxy)pyridin-2-yl)amino)-N,N-dimethylpyridine-3-sulfonamide (120 mg, 0.277 mmol) was suspended in MeOH (5 mL) then DCM (3 mL) was added until the mixture became homogeneous. Ammonium chloride (474 mg, 8.86 mmol) was added, followed by the addition of zinc (380 mg, 5.81 mmol). The reaction was stirred at rt overnight. The reaction was diluted with MeOH and filtered through celite. Concentration afforded the expected product (43 mg, 39% yield) which was carried forward without further purification. LCMS (M+H)=404.2 HPLC RT=1.142 min (Chromolith SpeedROD column 4.6×50 mm, 10-90% aqueous methanol over 4 minutes containing 0.1% TFA, 4 mL/min, monitoring at 220 nm).

Step 6: N-{4-[(2-{[5-(dimethylsulfamoyl)pyridin-2-yl]amino}pyridin-4-yl)oxy]-3-fluorophenyl}-2,4-dioxo-1-(propan-2-yl)-3-{[2-(trifluoromethyl)phenyl]methyl}-1,2,3,4-tetrahydropyrimidine-5-carboxamide A reaction vial was charged with 6-((4-(4-amino-2-fluorophenoxy)pyridin-2-yl)amino)-N,N-dimethylpyridine-3-sulfonamide (8.15 mg, 0.020 mmol) and 1-isopropyl-2,4-dioxo-3-(2-(trifluoromethyl)benzyl)-1,2,3,4-tetrahydropyrimidine-5-carboxylic acid (7.2 mg, 0.020 mmol) in DMF (0.25 mL). The reaction was initiated with the addition of triethylamine (5.63 µl, 0.040 mmol) and BOP (10.73 mg, 0.024 mmol). After stirring overnight, the reaction was diluted with DMF (1 mL) and purified by RP-HPLC using the following conditions; Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate: Gradient: a 0-minute hold at 47% B, 47-87% B over 20 minutes, then a 4-minute hold at 100% B; Flow Rate: 20 mL/min; Column Temperature: 25 C. Fractions containing the desired product were combined and dried via centrifugal evaporation to give N-{4-[(2-{[5-(dimethylsulfamoyl)pyridin-2-yl]amino}pyridin-4-yl)oxy]-3-fluorophenyl}-2,4-dioxo-1-(propan-2-yl)-3-{[2-(trifluoromethyl)phenyl]methyl}-1,2,3,4-tetrahydropyrimidine-5-carboxamide (9.6 mg, 0.0129 mmol). $^1$H NMR (500 MHz, DMSO-d6) δ 10.97 (s, 1H), 10.36 (s, 1H), 8.70 (s, 1H), 8.46 (d, J=1.8 Hz, 1H), 8.20 (d, J=5.8 Hz, 1H), 8.02-7.94 (m, 2H), 7.93-7.88 (m, 1H), 7.80 (d, J=7.9 Hz, 1H), 7.64-7.57 (m, 1H), 7.55-7.47 (m, 2H), 7.40-7.35 (m, 2H), 7.26 (br d, J=7.9 Hz, 1H), 6.60 (dd, J=5.6, 2.0 Hz, 1H), 5.30 (s, 2H), 4.80 (dt, J=13.5, 6.8 Hz, 1H), 1.43 (d, J=6.7 Hz, 6H); LCMS (M+H)=742.1. HPLC RT=2.385 min Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.: Gradient: 0% B to 100% B over 3 min, then a 0.75 min hold at 100% B; Flow: 1 mL/min; Detection: MS and UV (220 nm).

Examples 42-61

The compounds in Table 3 were prepared according to the procedures described for Examples 40 and 41.

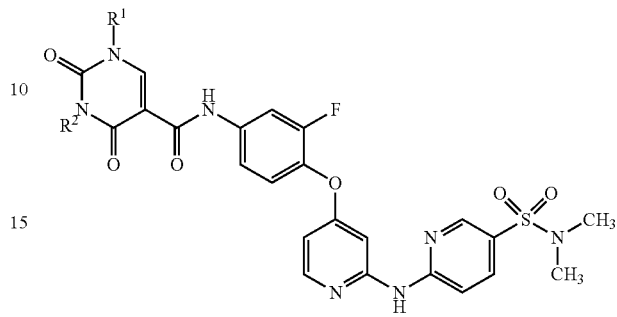

TABLE 3

| Ex. No. | R$^1$ | R$^2$ | HPLC RT (min) | LC/MS (M + H) | HPLC Method |
|---|---|---|---|---|---|
| 42 | isopropyl | phenyl | 2.12 | 660.1 | A |
| 43 | cyclopropyl | phenyl | 1.63 | 658.3 | B |
| 44 | methyl | 4-fluorophenyl | 1.99 | 650.3 | A |
| 45 | (S)-1-methoxypropan-2-yl | 4-fluorophenyl | 2.31 | 708.0 | A |
| 46 | (R)-tetrahydrofuran-3-yl | 4-fluorophenyl | 2.19 | 706.2 | A |
| 47 | (S)-tetrahydrofuran-3-yl | 4-fluorophenyl | 2.02 | 706.2 | A |
| 48 | isopropyl | 5-fluoropyridin-2-yl | 1.66 | 679.1 | A |

TABLE 3-continued

| Ex. No. | R¹ | R² | HPLC RT (min) | LC/MS (M + H) | HPLC Method |
|---|---|---|---|---|---|
| 49 | isopropyl | benzyl | 1.88 | 674.3 | C |
| 50 | isopropyl | bicyclo[1.1.1]pentyl | 1.945 | 650.3 | C |
| 51 | isopropyl | isopropyl | 1.881 | 626.4 | C |
| 52 | isopropyl | isobutyl | 1.911 | 640.3 | C |
| 53 | isopropyl | cyclohexyl | 2.013 | 666.2 | C |
| 54 | isopropyl | cyclopropylmethyl | 1.717 | 638.1 | C |
| 55 | (S)-2-hydroxymethyl-propyl | 4-fluorophenyl | 1.896 | 694.1 | A |
| 56 | (R)-2-hydroxymethyl-propyl | 4-fluorophenyl | 1.891 | 694.1 | A |
| 57 | 2-hydroxymethyl-propyl | 5-fluoropyridin-2-yl | 1.879 | 695.2 | A |
| 58 | isopropyl | pyridin-4-ylmethyl | 1.982 | 675.4 | A |
| 59 | isopropyl | 2-cyclopropylethyl | 2.438 | 652.3 | A |

TABLE 3-continued

| Ex. No. | R¹ | R² | HPLC RT (min) | LC/MS (M + H) | HPLC Method |
|---|---|---|---|---|---|
| 60 | H₃C-CH(-)-CH₃ (isopropyl) | 2-methoxybenzyl | 2.372 | 704.4 | A |
| 61 | H₃C-CH(-)-CH₃ (isopropyl) | 4-fluorobenzyl | 2.418 | 692.4 | A |

HPLC Conditions for Table 3:

Method A; Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: UV (220 nm).

Method B; Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm)

Method C; Column: Waters BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.: Gradient: 0% B, 0-100% B over 3 minutes, then a 0.75-minute hold at 100% B; Flow: 1.0 mL/min; Detection; UV at 220 nm.

Example 62

N-{4-[(2-{[5-(Dimethylsulfamoyl)pyridin-2-yl]amino}pyridin-4-yl)oxy]-3-fluorophenyl}-3-(4-methylphenyl)-2,4-dioxo-1-(propan-2-yl)-1,2,3,4-tetrahydropyrimidine-5-carboxamide Step 1. Ethyl 1-isopropyl-2,4-dioxo-1,2,3,4-tetrahydropyrimidine-5-carboxylate To a 40 mL vial containing ethyl 3-ethoxy-2-((ethoxycarbonyl)carbamoyl)acrylate (759.1 mg, 2.93 mmol) [Cusack. N. J. et al. *J. Chem. Soc. Perkin Trans.* 1 1973, 16, 1720-1731] in ethanol (14.6 mL) was added isopropylamine (276 μL, 3.22 mmol) to give an off-white suspension that quickly became a yellow homogeneous solution. The resulting reaction mixture was stirred for 1 h at room temperature. Potassium tert-butoxide (329 mg, 2.93 mmol) was added. The reaction mixture was stirred for 2 h, diluted with water, and extracted with EtOAc. The organic layers were combined, washed with brine, dried over MgSO4, filtered, concentrated, and purified by silica gel chromatography (24 g column, gradient from 0% to 100% EtOAc/hexanes). The fractions were concentrated in vacuo to give the title compound (557.7 mg, 84%) as a white solid. ¹H NMR (400 MHz, methanol-d4) δ 8.41 (s, 1H), 4.79 (spt, J=6.8 Hz, 1H), 4.30 (q, J=7.2 Hz, 2H), 1.40 (d, J=6.8 Hz, 6H), 1.33 (t, J=6.8 Hz, 3H); LCMS (M+H)=227.1; HPLC RT=0.62 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 2. Ethyl 1-isopropyl-2,4-dioxo-3-(p-tolyl)-1,2,3,4-tetrahydropyrimidine-5-carboxylate To a 1 dram vial containing ethyl 1-isopropyl-2,4-dioxo-1,2,3,4-tetrahydropyrimidine-5-carboxylate (75 mg, 0.332

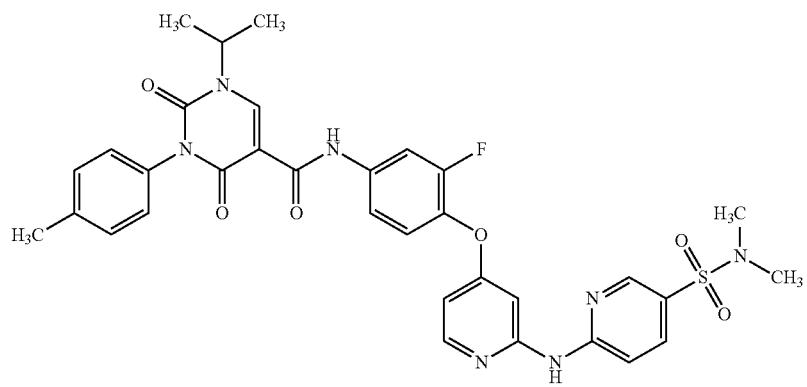

mmol), p-tolylboronic acid (90 mg, 0.663 mmol), and copper (II) acetate (60.2 mg, 0.332 mmol) in DMSO (663 μL) was added triethylamine (92 μL, 0.663 mmol). The vial was capped and heated at 60° C. for 17 h. The reaction mixture was cooled to room temperature, p-tolylboronic acid (90 mg, 0.663 mmol) was added, and the reaction mixture was heated at 60° C. for 3 days. The reaction mixture was purified by silica gel chromatography (24 g SiO$_2$, gradient from 0% to 5% MeOH-DCM). The fractions were concentrated in vacuo and then redissolved in EtOAc, washed with 10% aqueous LiCl, washed with brine, dried over MgSO4, filtered, and concentrated to give a yellow solid, which was further purified by silica gel chromatography (12 g SiO$_2$, gradient from 0% to 5% MeOH-DCM). The fractions were concentrated in vacuo to give the title compound (16.6 mg, 16%) as a white film. $^1$H NMR (400 MHz, methanol-d4) δ 8.51 (s, 1H), 7.30 (d, J=8.1 Hz, 2H), 7.10 (d, J=8.3 Hz, 2H), 4.83 (spt, J=7.0 Hz, 1H), 4.31 (q, J=7.1 Hz, 2H), 2.40 (s, 3H), 1.44 (d, J=6.8 Hz, 6H), 1.34 (t, J=7.1 Hz, 3H); LCMS (M+H)=317.1; HPLC RT=0.83 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 3. 1-Isopropyl-2,4-dioxo-3-(p-tolyl)-1,2,3,4-tetrahydropyrimidine-5-carboxylic acid To a 2 dram vial containing ethyl 1-isopropyl-2,4-dioxo-3-(p-tolyl)-1,2,3,4-tetrahydropyrimidine-5-carboxylate (16.6 mg, 0.052 mmol) in water (23 μL) was added a 4 M solution of HCl in 1,4-dioxane (420 μL, 1.679 mmol). The headspace was flushed with N$_2$ and the vial was capped and heated at 70° C. for 18 h. The reaction mixture was cooled to room temperature, concentrated, and purified by silica gel chromatography (4 g SiO$_2$, gradient from 0% to 5% MeOH-DCM). The fractions were concentrated in vacuo to give the title compound (11.6 mg, 77%) as a white film. $^1$H NMR (400 MHz, CDCl$_3$) δ 12.56-12.43 (br s, 1H), 8.58 (s, 1H), 7.36 (d, J=8.0 Hz, 2H), 7.13 (d, J=8.3 Hz, 2H), 4.96 (spt, J=6.8 Hz, 1H), 2.44 (s, 3H), 1.48 (d, J=6.8 Hz, 6H); LCMS (M+H)=289.0; HPLC RT=0.81 min (Column: BEH C18 2.1×50 mm; Mobile Phase A: water with 0.05% TFA; Mobile Phase B: acetonitrile with 0.05% TFA; Temperature: 50° C.: Gradient: 2-98% B over 1.7 min; Flow: 0.8 mL/min).

Step 4. N-{4-[(2-{[5-(dimethylsulfamoyl)pyridin-2-yl]amino}pyridin-4-yl)oxy]-3-fluorophenyl}-3-(4-methylphenyl)-2,4-dioxo-1-(propan-2-yl)-1,2,3,4-tetrahydropyrimidine-5-carboxamide To a 10 mL recovery flask containing 6-((4-(4-amino-2-fluorophenoxy)pyridin-2-yl)amino)-N,N-dimethylpyridine-3-sulfonamide (16.23 mg, 0.040 mmol, Example 41—Step 6), 1-isopropyl-2,4-dioxo-3-(p-tolyl)-1,2,3,4-tetrahydropyrimidine-5-carboxylic acid (11.6 mg, 0.040 mmol), and HATU (18.4 mg, 0.048 mmol) in DMF (0.40 ML) was added triethylamine (6.7 μL, 0.048 mmol). The reaction mixture turned pale yellow and was stirred at room temperature for 6 h. The reaction mixture was diluted with 0.6 mL DMF, filtered through a syringe filter, and purified by preparative LC/MS (Column: XBridge C18, 200×19 mm; Mobile Phase A: 5:95 acetonitrile:water with 10-mM ammonium acetate; Mobile Phase B: 95:5 acetonitrile:water with 10-mM ammonium acetate; Gradient: a 0-minute hold at 40% B, 40-80% B over 20 minutes, then a 4-minute hold at 100% B; Flow Rate: 20 mL/min). Fractions containing the desired product were combined and dried via centrifugal evaporation to give the title compound (19.6 mg, 72%). $^1$H NMR (500 MHz, DMSO-d6) δ 11.06 (s, 1H), 10.33 (s, 1H), 8.65 (s, 1H), 8.44 (s, 1H), 8.18 (br d, J=5.5 Hz, 1H), 8.02-7.88 (m, 3H), 7.46 (br d, J=8.5 Hz, 1H), 7.40-7.26 (m, 4H), 7.21 (br d, J=7.9 Hz, 2H), 6.63-6.54 (m, 1H), 4.85-4.69 (m, 1H), 2.60 (s, 6H), 2.37 (s, 3H), 1.41 (d, J=6.4 Hz, 6H); LCMS (M+H)=674.4; HPLC RT=2.25 min (Column: Waters XBridge C18 2.1×50 mm; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min).

Examples 63-73

The compounds in Table 4 were prepared according to the procedures described for Example 62.

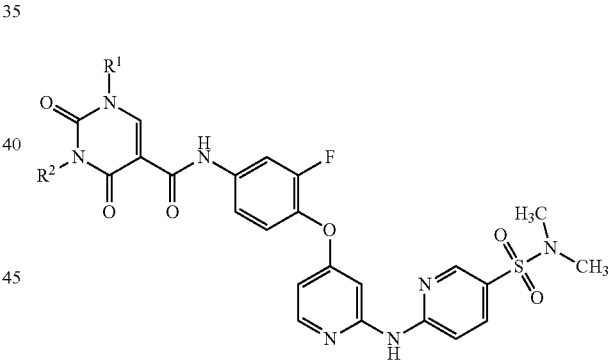

TABLE 4

| Ex. No. | R$^1$ | R$^2$ | HPLC RT (min) | LC/MS (M + H) | HPLC Method |
|---|---|---|---|---|---|
| 63 | H$_3$C⟍⟋CH$_3$ | 4-methoxyphenyl | 2.08 | 690.1 | A |

TABLE 4-continued

| Ex. No. | R¹ | R² | HPLC RT (min) | LC/MS (M + H) | HPLC Method |
|---|---|---|---|---|---|
| 64 | isopropyl | 4-acetylphenyl | 2.07 | 702.4 | A |
| 65 | isopropyl | 4-(trifluoromethyl)phenyl | 2.29 | 728.1 | A |
| 66 | isopropyl | 4-chlorophenyl | 2.25 | 694.0 | A |
| 67 | isopropyl | 3-chlorophenyl | 2.69 | 694.1 | A |
| 68 | isopropyl | 3-fluorophenyl | 2.18 | 678.3 | A |
| 69 | isopropyl | 3,4-difluorophenyl | 2.23 | 696.3 | A |
| 70 | isopropyl | 3-methylphenyl | 2.61 | 674.1 | A |
| 71 | isopropyl | 3-methoxyphenyl | 2.17 | 690.4 | A |

TABLE 4-continued

| Ex. No. | R¹ | R² | HPLC RT (min) | LC/MS (M + H) | HPLC Method |
|---|---|---|---|---|---|
| 72 | 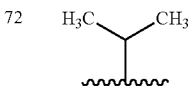 | 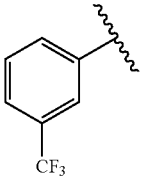 [SMILES: *c1cccc(C(F)(F)F)c1] | 2.72 | 728.2 | A |
| 73 | 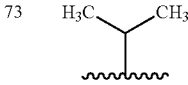 | 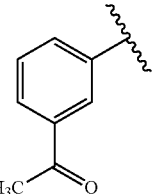 | 2.42 | 702.1 | A |

HPLC Conditions for Table 4:

Method A; Column: Waters XBridge C18 2.1×50 mm; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B: Flow: 1 mL/min; Detection; UV at 220 nm.

Example 74

N-{4-[(2-{[5-(dimethylsulfamoyl)pyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide

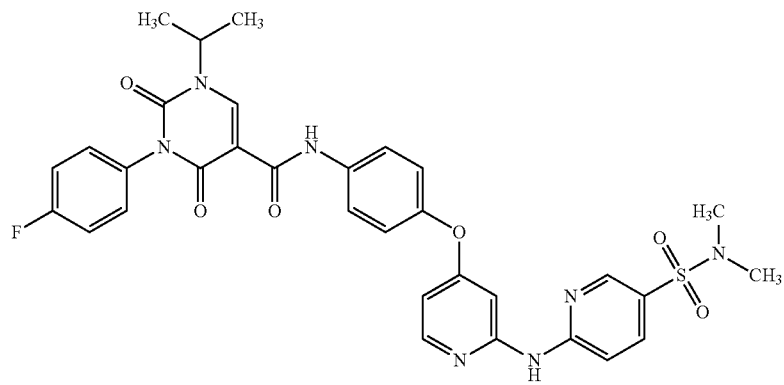 [SMILES: CC(C)n1cc(C(=O)Nc2ccc(Oc3ccnc(Nc4ccc(S(=O)(=O)N(C)C)cn4)c3)cc2)c(=O)n(-c2ccc(F)cc2)c1=O]

Step 1. 2-Chloro-4-(4-nitrophenoxy)pyridine

To a 40 mL vial containing 2-chloropyridin-4-ol (300 mg, 2.32 mmol) and 1-fluoro-4-nitrobenzene (327 mg, 2.32 mmol) in NMP (3 mL) was added Cs₂CO₃ (830 mg, 2.55 mmol). The reaction was heated on a heating block at 110° C. for 30 minutes then cooled to room temperature. The reaction was diluted with water and the resulting precipitate collected by filtration, rinsed with water and dried under vacuum to give the title compound (449.5 mg, 86%) as an off-white solid. LCMS (M+H)=251; HPLC RT=1.863 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2. 4-((2-Chloropyridin-4-yl)oxy)aniline

To a 40 mL vial containing 2-chloro-4-(4-nitrophenoxy)pyridine (499.5 mg, 1.99 mmol), zinc powder (1042 mg, 15.94 mmol) in EtOH (5 mL) was added ammonium chloride (853 mg, 15.94 mmol). The reaction was heated to 80° C. for 1 hour then cooled to room temperature. The reaction was filtered through a 0.45 μm membrane with EtOH rinses and then concentrated. The residue was diluted with water and basified with sat. aqueous NaHCO₃ solution, stirring at room temperature. The resulting precipitate was collected by filtration, rinsed with water and dried under vacuum to give the title compound (396.7 mg, 90%) as an off-white solid. ¹H NMR (400 MHz, DMSO-d6) δ 8.23 (d, J=5.6 Hz, 1H), 6.90-6.82 (m, 4H), 6.67-6.59 (m, 2H), 5.18 (s, 2H). LCMS (M+H)=221; HPLC RT=0.718 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.: Gradient: 0-100% B over 4 min; Flow: 4 mL/min).

Step 3: N-(4-((2-chloropyridin-4-yl)oxy)phenyl)-3-(4-fluorophenyl)-1-isopropyl-2,4-dioxo-1,2,3,4-tetrahydropyrimidine-5-carboxamide To a 4 mL vial containing 3-(4-fluorophenyl)-1-isopropyl-2,4-dioxo-1,2,3,4-tetrahydropyrimidine-5-carboxylic acid (50 mg, 0.171 mmol), 4-((2-chloropyridin-4-yl)oxy)aniline (37.7 mg, 0.171 mmol) and Et₃N (29 uL, 0.205 mmol) in NMP (0.5 mL) was added HATU (78 mg, 0.205 mmol). The reaction was stirred at room temperature 4 hours and diluted with water and saturated aqueous NaHCO₃ solution. The white precipitate that formed was collected by filtration, rinsed with water and dried under vacuum to give the title compound (80.6 mg, 95%) as a white solid. LCMS (M+H)=495: HPLC RT=2.791 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: N-{4-[(2-{[5-(dimethylsulfamoyl)pyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide To a 4 mL vial containing N-(4-((2-chloropyridin-4-yl)oxy)phenyl)-3-(4-fluorophenyl)-1-isopropyl-2,4-dioxo-1,2,3,4-tetrahydropyrimidine-5-carboxamide (24.6 mg, 0.050 mmol), 6-amino-N,N-dimethylpyridine-3-sulfonamide (15 mg, 0.075 mmol), Xantphos (3.45 mg, 5.96 umol), Pd₂dba₃ (4.55 mg, 4.97 umol) and Cs₂CO₃ (48.6 mg, 0.149 mmol) in dioxane (0.5 mL). The reaction was heated to 110° C. for 2 hours, then diluted with THF and filtered through a 0.45 μm membrane. The reaction mixture was concentrated and the crude material was purified via preparative LC/MS with the following conditions; Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 43-83% B over 20 minutes, then a 4-minute hold at 100% B; Flow: 20 mL/min. Fractions containing the desired product were combined and dried via centrifugal evaporation to give the title compound (18.8 mg). ¹H NMR (500 MHz, DMSO-d) δ 10.90 (s, 1H), 10.31 (s, 1H), 8.65 (s, 1H), 8.45 (s, 1H), 8.17 (d, J=5.8 Hz, 1H), 7.98-7.89 (m, 2H), 7.77 (d, J=8.9 Hz, 2H), 7.45-7.40 (m, 2H), 7.38-7.32 (m, 3H), 7.18 (d, J=8.9 Hz, 2H), 6.55 (dd, J=5.6, 2.0 Hz, 1H), 4.77 (dt, J=13.4, 6.9 Hz, 1H), 2.60 (s, 6H), 1.42 (d, J=6.7 Hz, 6H); LCMS (M+H)+=660.2: HPLC RT=1.77 min (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B: Flow: 1 mL/min; Detection UV 220 nm)

Example 75

N-{4-[(2-{[5-(dimethylsulfamoyl)pyridin-2-yl]amino}pyridin-4-yl)oxy]phenyl}-2,4-dioxo-3-phenyl-1-(propan-2-yl)-1,2,3,4-tetrahydropyrimidine-5-carboxamide

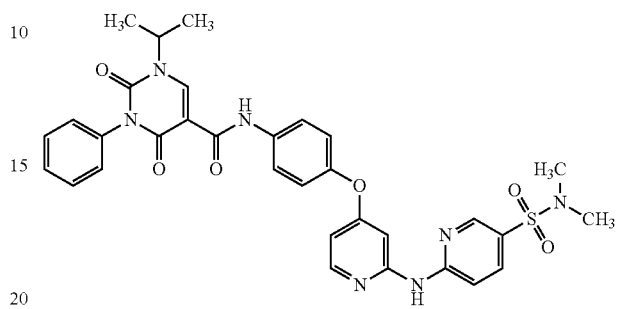

Step 1. Diethyl 2-((3-phenylureido)methylene)malonate

To a 40 mL vial containing diethyl 2-(aminomethylene)malonate (400 mg, 2.14 mmol), DIPEA (411 uL, 2.35 mmol) in dioxane (0.6 mL) was added isocyanatobenzene (244 uL, 2.24 mmol). The reaction was heated to 100° C. for 18 hours then cooled to room temperature. The precipitate that formed was collected by filtration with small dioxane and hexane rinses and dried under vacuum to give the title compound (294 mg, 44.5%) as a white solid. ¹H NMR (500 MHz, DMSO-d₆) δ 10.76-10.50 (m, 1H), 10.48-10.25 (m, 1H), 8.48 (br s, 1H), 7.59-7.45 (m, 2H), 7.39-7.25 (m, 2H), 7.16-7.02 (m, 1H), 4.25 (q, J=7.0 Hz, 2H), 4.16 (q, J=7.0 Hz, 2H), 1.31-1.22 (m, 6H); LCMS (M+H)=307; HPLC RT=2.298 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2. Ethyl 2,4-dioxo-3-phenyl-1,2,3,4-tetrahydropyrimidine-5-carboxylate

To a 8 mL vial containing diethyl 2-((3-phenylureido)methylene)malonate (290 mg, 0.94 mmol) in EtOH (1.2 mL) was added sodium ethoxide (21% w/w in EtOH, 566 uL). The reaction was stirred at room temperature for 3 hours then citric acid (1M aqueous, 0.947 mL) was added and the reaction mixture added to water (30 mL). The precipitate that formed was collected by filtration with water rinses and dried under vacuum to give the title compound (228.3 mg, 93%) as a pale orange solid. ¹H NMR (500 MHz, DMSO-d6) δ 11.99 (br s, 1H), 8.25 (s, 1H), 7.51-7.43 (m, 2H), 7.43-7.37 (m, 1H), 7.24 (br d, J=7.3 Hz, 2H), 4.18 (q, J=7.0 Hz, 2H), 1.23 (t, J=7.1 Hz, 3H); LCMS (M+H)=261; HPLC RT=0.742 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3. Ethyl 1-isopropyl-2,4-dioxo-3-phenyl-1,2,3,4-tetrahydropyrimidine-5-carboxylate To a 8 mL vial containing ethyl 1-isopropyl-2,4-dioxo-3-phenyl-1,2,3,4-tetrahydropyrimidine-5-carboxylate (208.7 mg, 0.802 mmol) and K$_2$CO$_3$ (222 mg, 1.604 mmol) in DMF (0.5 mL) was added 2-iodopropane (160 uL, 1.604 mmol). The reaction mixture was heated to 70° C. for 4 hours then cooled to room temperature and diluted with water. The precipitate that formed was collected by filtration with water and hexane rinses and dried under vacuum to give the title compound (177 mg, 73%) as an off-white solid. $^1$H NMR (400 MHz, DMSO-d6) δ 8.44 (s, 1H), 7.51-7.44 (m, 2H), 7.44-7.37 (m, 1H), 7.28-7.21 (m, 2H), 4.70 (spt, J=6.7 Hz, 1H), 4.21 (q, J=7.1 Hz, 2H), 1.37 (d, J=6.8 Hz, 6H), 1.25 (t, J=7.1 Hz, 3H); LCMS (M+H)=303; HPLC RT=1.373 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.: Gradient: 0-100% B over 4 min; Flow: 4 mL/min).

Step 4. 1-Isopropyl-2,4-dioxo-3-phenyl-1,2,3,4-tetrahydropyrimidine-5-carboxylic acid To a 4 mL vial containing ethyl 1-isopropyl-2,4-dioxo-3-phenyl-1,2,3,4-tetrahydropyrimidine-5-carboxylate (177 mg, 0.58 mmol) was added HCl (4M in dioxane, 680 uL) and water (150 uL). The reaction mixture was heated to 70° C. for 18 hours then cooled to room temperature. The reaction was concentrated and diluted with water. The precipitate that formed was collected by filtration with water rinses and dried under vacuum to give the title compound (118 mg, 73%) as an off-white solid. $^1$H NMR (400 MHz, DMSO-d6) δ 12.69 (br s, 1H), 8.58 (s, 1H), 7.57-7.39 (m, 3H), 7.34-7.24 (m, 2H), 4.73 (spt, J=6.8 Hz, 1H), 1.39 (d. J=6.8 Hz, 6H); LCMS (M+H)=275; HPLC RT=0.982 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C. Gradient: 0-100% B over 4 min; Flow: 4 mL/min).

Step 5: N-(4-((2-chloropyridin-4-yl)oxy)phenyl)-1-isopropyl-2,4-dioxo-3-phenyl-1,2,3,4-tetrahydropyrimidine-5-carboxamide To a 4 mL vial containing 1-isopropyl-2,4-dioxo-3-phenyl-1,2,3,4-tetrahydropyrimidine-5-carboxylic acid (50 mg, 0.182 mmol), 4-((2-chloropyridin-4-yl)oxy)aniline (40.2 mg, 0.182 mmol, Example 74—Step 2) and Et$_3$N (30 uL, 0.219 mmol) in NMP (0.5 mL) was added HATU (83 mg, 0.219 mmol). The reaction was stirred at room temperature 4 hours and diluted with water and saturated aqueous NaHCO$_3$ solution. The white precipitate that formed was collected by filtration, rinsed with water and dried under vacuum to give the title compound (82.4 mg, 95%) as a white solid. LCMS (M+H)=477: HPLC RT=2.758 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 6: N-{4-[(2-{[5-(dimethylsulfamoyl)pyridin-2-yl]amino}pyridin-4-yl)oxy]phenyl}-2,4-dioxo-3-phenyl-1-propan-2-yl)-1,2,3,4-tetrahydropyrimidine-5-carboxamide To a 4 mL vial containing N-(4-((2-chloropyridin-4-yl)oxy)phenyl)-1-isopropyl-2,4-dioxo-3-phenyl-1,2,3,4-tetrahydropyrimidine-5-carboxamide (23.7 mg, 0.050 mmol), 6-amino-N,N-dimethylpyridine-3-sulfonamide (15 mg, 0.075 mmol), Xantphos (3.45 mg, 5.96 umol), Pd$_2$dba$_3$ (4.55 mg, 4.97 umol) and Cs$_2$CO$_3$ (48.6 mg, 0.149 mmol) in dioxane (0.5 mL). The reaction was heated to 110° C. for 2 hours, diluted with THF and filtered through a 0.45 um membrane. The reaction mixture was concentrated and the crude material was purified via preparative LC/MS with the following conditions; Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 18-58% B over 20 minutes, then a 4-minute hold at 100% B; Flow: 20 mL/min. Fractions containing the desired product were combined and dried via centrifugal evaporation to give the title compound (16.8 mg, 51.8%). $^1$H NMR (500 MHz, DMSO-d$_6$) δ 10.% (s, 1H), 8.65 (s, 1H), 8.53 (d, J=1.8 Hz, 1H), 8.24 (d, J=6.4 Hz, 1H), 8.05 (dd, J=8.9, 2.1 Hz, 1H), 7.80 (br d, J=8.9 Hz, 2H), 7.64 (br d, J=8.5 Hz, 1H), 7.56-7.49 (m, 2H), 7.48-7.43 (m, 1H), 7.35 (br d, J=7.3 Hz, 2H), 7.24 (br d, J=8.2 Hz, 2H), 7.06 (br s, 1H), 6.79 (br d, J=4.6 Hz, 1H), 4.77 (dt, J=13.4, 6.7 Hz, 1H), 2.63 (s, 6H), 1.42 (d, J=6.7 Hz, 6H); LCMS (M+H)+=642.2; HPLC RT=1.57 min (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection UV 220 nm)

Example 76

N-{3-Fluoro-4-[(2-{[5-(piperidine-1-sulfonyl)pyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide

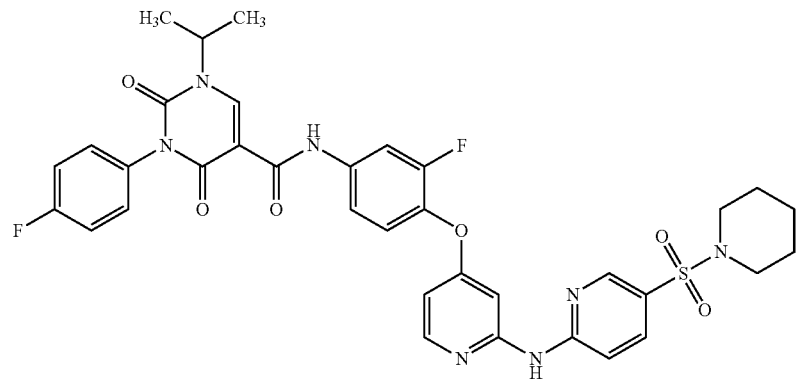 [SMILES: CC(C)n1cc(C(=O)Nc2ccc(Oc3ccnc(Nc4ccc(S(=O)(=O)N5CCCCC5)cn4)c3)c(F)c2)c(=O)n(-c2ccc(F)cc2)c1=O]

Step 1

N-(4-((2-chloropyridin-4-yl)oxy)-3-fluorophenyl)-3-(4-fluorophenyl)-1-isopropyl-2,4-dioxo-1,2,3,4-tetrahydropyrimidine-5-carboxamide (30 mg, 0.058 mmol, Example 1—Step 8), 5-(piperidin-1-ylsulfonyl)pyridin-2-amine (14.11 mg, 0.058 mmol), potassium carbonate (24.25 mg, 0.175 mmol) and BrettPhos Precatalyst G1 (4.67 mg, 5.85 μmol) were suspended in t-BuOH/DMA (6:1) (688 μl). The reaction mixture was degassed with a stream of $N_2$ for two minutes, sealed and heated to 120° C. in the microwave reactor for 45 min. After cooling to rt, the reaction mixture was diluted with EtOAc, filtered through a PTFE frit, and concentrated. The crude material was purified via preparative LC/MS with the following conditions; Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate. Gradient: 45-90% B over 25 minutes, then a 5-minute hold at 100% B; Flow: 20 mL/min. Fractions containing the desired product were combined and dried via centrifugal evaporation to afford the titled product (5.0 mg). 1H NMR (500 MHz, DMSO-$d_6$) δ 11.01 (s, 1H), 10.31 (s, 1H), 8.66 (s, 1H), 8.41 (d, J=1.8 Hz, 1H), 8.19 (d, J=5.8 Hz, 1H), 8.06-7.82 (m, 3H), 7.53-7.27 (m, 7H), 6.59 (dd, J=5.8, 2.1 Hz, 1H), 4.77 (dt, J=13.4, 6.6 Hz, 1H), 2.88 (br s, 4H), 1.53 (br s, 4H), 1.42 (br d, J=6.7 Hz, 6H), 1.36 (br s, 2H); LCMS (M+H)+=718.2: HPLC RT=2.34 min: (Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B: Flow: 1 mL/min; Detection: MS and UV (220 nm).

Where the 6-aminopyridine-3-sulfonamides are not commercially available, they can be prepared by using the following methodology:

A suspension of (E)-6-(((dimethylamino)methylene)amino)pyridine-3-sulfonyl chloride (150 mg, 0.606 mmol) in THF (5 mL) at rt was treated with azetidin-3-ol, HCl (80 mg, 0.727 mmol), followed by Hunig's Base (0.264 mL, 1.514 mmol). After 1 hr, 1 N aq NaOH solution (1 mL) was added and the reaction mixture was heated to 75° C. for 16 h. Column chromatography (24 g $SiO_2$, 0 to 8% MeOH—$CH_2Cl_2$) afforded 1-((6-aminopyridin-3-yl)sulfonyl)azetidin-3-ol (117.2 mg, 84% yield). 1H NMR (400 MHz, CHLOROFORM-d) δ 11.42-11.20 (m, 1H), 8.55 (d, J=2.3 Hz, 1H), 7.84 (dd, J=8.7, 2.4 Hz, 1H), 6.59 (d, J=8.8 Hz, 1H), 5.03 (br d, J=1.1 Hz, 2H), 3.64-3.57 (m, 2H), 3.12 (dd, J=7.5, 4.3 Hz, 3H)

Examples 77 to 85

The compounds in Table 5 were prepared according to the procedures described for Example 76.

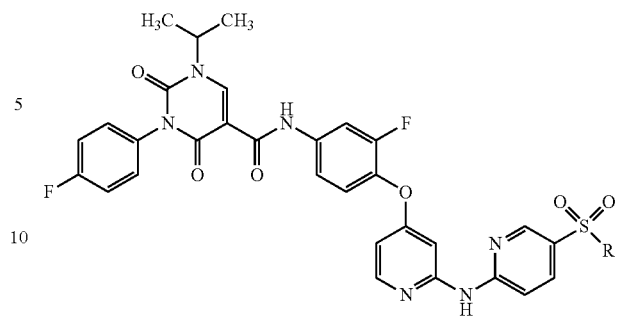

TABLE 5

| Ex. No. | R | HPLC RT (min) | LC/MS (M + H) | HPLC Method |
|---|---|---|---|---|
| 77 | —NHCH₃ | 1.67 | 664.3 | A |
| 78 | —NH—CH(CH₃)₂ | 2.12 | 692.16 | B |
| 79 | —NH-cyclopropyl | 2.12 | 690.15 | B |
| 80 | —NH—C(CH₃)₃ | 1.84 | 706.3 | A |
| 81 | —N(azetidine) | 2.11 | 690.09 | B |
| 82 | —N(azetidine)-OH | 1.92 | 706.27 | B |
| 83 | —N(azetidine)(CH₃)OH | 1.96 | 720.36 | B |
| 84 | —N(morpholine) | 2.09 | 719.86 | B |
| 85 | —N(piperazine)-CH₃ | 2.04 | 732.88 | B |

HPLC Conditions for Table 5:

Method A; Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.: Gradient: 0% B to 100% B over 3 min, then a 0.75 min hold at 100% B; Flow: 1 m/min; Detection: MS and UV (220 nm).

Method B; Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: UV (220 nm).

Example 86

N-{4-[(2-{[5-(dimethylsulfamoyl)-4-methylpyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide

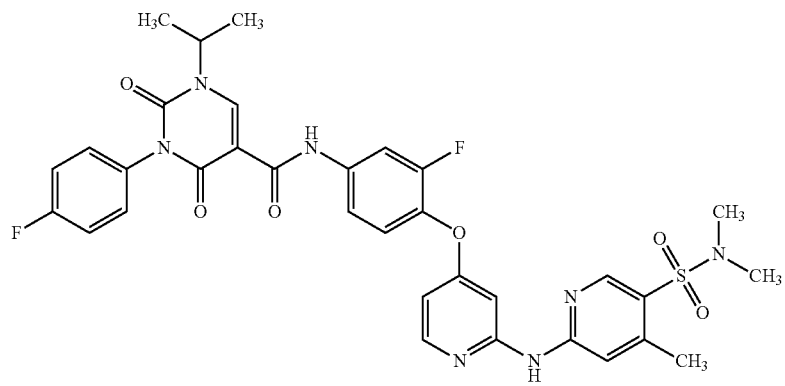 [SMILES: Cc1cc(Nc2cc(Oc3ccc(NC(=O)c4cn(C(C)C)c(=O)n(-c5ccc(F)cc5)c4=O)cc3F)ccn2)ncc1S(=O)(=O)N(C)C]

Step 1: 6-chloro-N,N,4-trimethylpyridine-3-sulfonamide

A mixture of 6-chloro-4-methylpyridine-3-sulfonyl chloride (0.25 g, 1.106 mmol) in THF (5 mL) was treated with Hunig's Base (0.290 mL, 1.659 mmol), followed by dimethylamine (2.0 M in THF, 0.829 mL, 1.659 mmol) at room temperature. After 1 hour, the reaction was concentrated and the crude was purified by column chromatography (24 g SiO2, 0 to 100% EtOAx-hexanes, gradient elution) to afford 6-chloro-N,N,4-trimethylpyridine-3-sulfonamide (213 mg, 0.908 mmol, 82% yield). LCMS (M+H)=234.9; LCMS RT=0.79 min; (Column: BEH C18 2.1×50 mm; Mobile Phase A: water with 0.05% TFA; Mobile Phase B: acetonitrile with 0.05% TFA; Temperature: 50° C.: Gradient: 2-98% B over 1.7 min; Flow: 0.8 mL/min).

Step 2: 6-Amino-N,N,4-trimethylpyridine-3-sulfonamide

A mixture of 6-chloro-N,N,4-trimethylpyridine-3-sulfonamide (213 mg, 0.908 mmol) in 2.0 N in NH3-iPrOH (4.538 mL, 9.08 mmol) was stirred at 80° C. for 16 h. No reaction occurred. The mixture was transferred to a steel bomb, and MeOH (10 mL) was added. The reaction mixture was cooled to −78° C., and ammonia gas was bubbled through the mixture for 3 mins. The reaction vessel was sealed and heated 150° C. for 16 h. After cooling to room temperature, the reaction mixture was concentrated and the crude product was purified by column chromatography (12 g SiO2, 0 to 100% EtOAc-hexane, gradient elution) to yield 6-amino-N,N,4-trimethylpyridine-3-sulfonamide (145.4 mg, 74.4% yield): 1H NMR (400 MHz, CHLOROFORM-d) δ 8.53 (s, 1H), 6.37 (s, 1H), 4.88 (br s, 2H), 2.81 (s, 6H), 2.51 (s, 3H); LCMS (M+H)+=216.1; LCMS RT=0.48 min; (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 3: N-{4-[(2-{[5-(dimethylsulfamoyl)-4-methylpyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide N-(4-((2-chloropyridin-4-yl)oxy)-3-fluorophenyl)-3-(4-fluorophenyl)-1-isopropyl-2,4-dioxo-1,2,3,4-tetrahydropyrimidine-5-carboxamide (30 mg, 0.058 mmol, Example 1—Step 7), 6-amino-N,N,4-trimethylpyridine-3-sulfonamide (13.85 mg, 0.064 mmol), potassium carbonate (175 mg, 0.175 mmol) and BrettPhos Precatalyst G1 (5.85 mg, 5.85 μmol) were suspended in t-BuOH/DMA (6:1) (688 μl). The reaction mixture was degassed with a stream of N2 over 2 min, sealed and heated to 120° C. in the microwave reactor for 45 min. After cooling to room temperature, the reaction mixture was diluted with EtOAc and filtered through a PTFE frit. The crude material was purified via preparative LC/MS with the following conditions; Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate: Gradient: 40-80% B over 20 minutes, then a 4-minute hold at 100% B; Flow: 20 mL/min. Fractions containing the desired product were combined and dried via centrifugal evaporation to afford the titled compound (6.1 mg, 14% yield). 1H NMR (500 MHz, DMSO-d6) δ 11.00 (s, 1H), 10.16 (s, 1H), 8.65 (s, 1H), 8.40 (s, 1H), 8.19 (d, J=5.8 Hz, 1H), 7.97 (br d, J=13.1 Hz, 1H), 7.68 (s, 1H), 7.52-7.28 (m, 7H), 6.57 (br d, J=4.0 Hz, 1H), 4.77 (dt, J=13.4, 6.7 Hz, 1H), 2.69 (s, 5H), 2.48 (s, 3H), 1.42 (br d, J=6.7 Hz, 6H); LCMS (M+H)+=692.1; HPLC RT=2.40 min; Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Example 87

N-[3-fluoro-4-({2-[(5-methanesulfonamidopyridin-2-yl)amino]pyridin-4-yl}oxy)phenyl]-3-(4-fluorophenyl)-2,4-dioxo-1-(propan-2-yl)-1,2,3,4-tetrahydropyrimidine-5-carboxamide

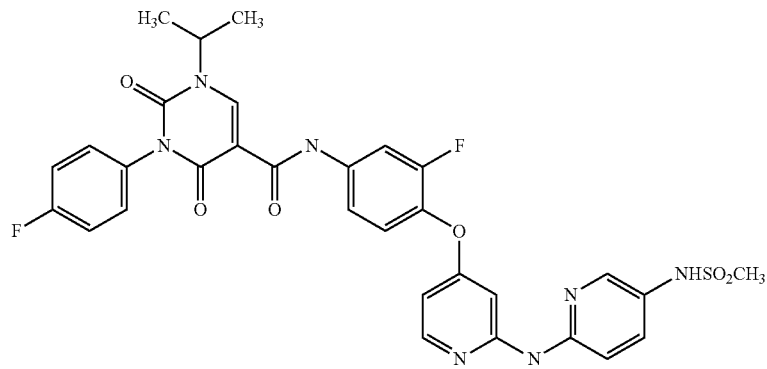

Step 1:
N-(4-methoxybenzyl)-5-nitropyridin-2-amine

A mixture of 2-chloro-5-nitropyridine (200 mg, 1.26 mmol), 4-methoxybenzylamine (173 mg, 1.26 mmol) and triethylamine (352 μl, 2.52 mmol) in DMF (3 mL) was stirred at 100° C. for 4 h. The solvent was evaporated and the residue was purified by column chromatography (24 g SiO₂, 0 to 70% EtOAc-hexanes, gradient elution) to afford the title compound (271 mg, 83%). ¹H NMR (499 MHz, DMSO-d₆) δ 9.14-8.81 (m, 1H), 8.46-8.46 (m, 1H), 8.49 (br s, 1H), 8.12 (dd, J=9.3, 2.4 Hz, 1H), 7.27 (d, J=8.7 Hz, 2H), 6.98-6.84 (m, 2H), 6.62 (br d, J=8.1 Hz, 1H), 4.56 (br s, 2H), 3.74 (s, 3H). LCMS (M+H)=260.4. HPLC RT=1.09 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 2: N²-(4-methoxybenzyl)pyridine-2,5-diamine

To a solution of N-(4-methoxybenzyl)-5-nitropyridin-2-amine (271 mg, 1.05 mmol) in a mixture of methanol and tetrahydrofuran (v/v, 1:1, 5.2 mL) at room temperature was added ammonium chloride (559 mg, 10.45 mmol) and zinc (683 mg, 10.45 mmol). The mixture was stirred at room temperature for 14 h. The reaction mixture was filtered though celite and rinsed with methanol. The combined filtrates were concentrated, and the residue was diluted with brine (20 mL) and extracted with ethyl acetate (15 mL×3). The organic layer was separated, dried over sodium sulfate, and concentrated to afford the crude product, which was purified by column chromatography (24 g SiO₂. 0 to 5% MeOH-DCM, gradient elution) to afford the title compound (81 mg, 34%). LCMS (M+H)=230.2; HPLC RT=0.52 min (Column: Waters Acquity SDS C8 2.1×50 mm; Mobile Phase A; Water with 0.05% TFA; Mobile Phase B; Acetonitrile with 0.05% TFA; Temperature: 40° C.; Gradient: 2-98% B over 1.5 min; Flow: 1 mL/min).

Step 3: N-(6-((4-methoxybenzyl)amino)pyridin-3-yl)methanesulfonamide

To a solution of N²-(4-methoxybenzyl)pyridine-2,5-diamine (81 mg, 0.35 mmol) and pyridine (143 μl, 1.77 mmol) in dichloromethane (2 mL) at 0° C., methanesulfonyl chloride (22.02 μl, 0.28 mmol) was added. The reaction was stirred at 0° C. for 1.5 h. The solvent was evaporated and the residue was purified by column chromatography (24 g SiO2, 0 to 5% MeOH-DCM, gradient elution) to afford the title compound (85 mg, 78%). LCMS (M+H)=308.2; HPLC RT=0.55 min (Column: Waters Acquity BEH C18 2.1×50 mm; Mobile Phase A; Water with 0.05% TFA; Mobile Phase B; Acetonitrile with 0.05% TFA; Temperature: 40° C.: Gradient: 2-98% B over 1.5 min; Flow: 1 mL/min).

Step 4:
N-(6-aminopyridin-3-yl)methanesulfonamide

A mixture of N-(6-((4-methoxybenzyl)amino)pyridin-3-yl)methanesulfonamide (85 mg, 0.28 mmol) and TFA (2.1 mL, 27.7 mmol) in dichloromethane (1 mL) was stirred at rt for 12 h. The reaction was diluted with saturated sodium bicarbonate (5 mL) and extracted with DCM (3×) to afford the title compound (46 mg, 89%) which was carried on to the subsequent step without further purification. LCMS (M+H) =188.1. HPLC RT=0.25 min (Column: Waters Acquity BEH C18 2.1×50 mm; Mobile Phase A; Water with 0.05% TFA; Mobile Phase B; Acetonitrile with 0.05% TFA; Temperature: 40° C.; Gradient: 2-98% B over 1.5 min; Flow: 1 mL/min).

Step 5: N-[3-fluoro-4-({2-[(5-methanesulfonamidopyridin-2-yl)amino]pyridin-4-yl}oxy)phenyl]-3-(4-fluorophenyl)-2,4-dioxo-1-(propan-2-yl)-1,2,3,4-tetrahydropyrimidine-5-carboxamide A mixture of N-(4-((2-chloropyridin-4-yl)oxy)-3-fluorophenyl)-3-(4-fluorophenyl)-1-isopropyl-2,4-dioxo-1,2,3,4-tetrahydropyrimidine-5-carboxamide (25 mg, 0.05 mmol, Example 1—Step 7), N-(6-aminopyridin-3-yl)methanesulfonamide (9.13 mg, 0.05 mmol), K₂CO₃ (20.21 mg, 0.15 mmol) and chloro[2-(dicyclohexylphosphino)-3,6-dimethoxy-2',4',6'-triisopropyl-1,1'-biphenyl][2-(2-aminoethyl) phenyl]palladium(II) (3.89 mg, 4.87 µmol) in t-Butanol/DMA 6/1 (975 µl) was degassed with N₂ gas and heated to 120° C. for 3 h. The reaction was diluted with DMF, filtered and purified by preparative LC/MS (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 31-71% B over 19 minutes, then a 5-minute hold at 100% B: Flow: 20 mL/min.) to afford the title compound (7 mg, 21.6%). ¹H NMR (500 MHz, DMSO-d₆) δ 11.01 (s, 1H), 9.68 (s, 1H), 8.66 (s, 1H), 8.10 (d, J=5.8 Hz, 1H), 7.99 (br s, 1H), 7.96 (s, 1H), 7.70 (d, J=8.9 Hz, 1H), 7.52 (dd, J=8.9, 2.1 Hz, 1H), 7.47 (br d, J=8.5 Hz, 1H), 7.45-7.39 (m, 2H), 7.39-7.32 (m, 3H), 7.30-7.18 (m, 1H), 6.50-6.40 (m, 1H), 4.77 (dt, J=13.6, 6.9 Hz, 1H), 2.92 (s, 3H), 1.42 (d, J=6.7 Hz, 6H), 1.00 (d, J=6.1 Hz, 1H); LCMS (M+H) =664.1; HPLC RT=1.78 min (Column: Waters XBridge C18 2.1×50 mm; Mobile Phase A: 5:95 ACN:water with 0.1% TFA; Mobile Phase B: 95:5 ACN:water with 0.1% TFA; Temperature: 40° C.; Gradient: 0-100% B over 3 min; Flow: 1 mL/min).

Example 88

N-{3-fluoro-4-[(2-{[5-(2-oxopyrrolidin-1-yl)pyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide

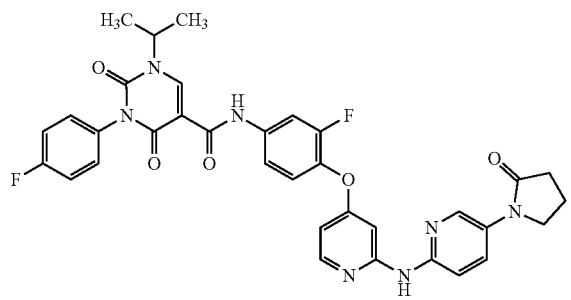 [SMILES: CC(C)n1cc(C(=O)Nc2ccc(Oc3ccnc(Nc4ccc(N5CCCC5=O)cn4)c3)c(F)c2)c(=O)n(-c2ccc(F)cc2)c1=O]

Step 1: 1-(6-aminopyridin-3-yl)pyrrolidin-2-one

To a 20 mL vial containing 5-bromopyridin-2-amine (Aldrich, 488 mg, 2.82 mmol), copper(I) iodide (Aldrich, 90 mg, 0.47 mmol) and K₂CO₃ (EMD, 650 mg, 4.70 mmol) in dioxane (4.7 mL) was added pyrrolidin-2-one (Aldrich, 200 mg, 2.35 mmol), and N¹,N²-dimethylethane-1,2-diamine (Aldrich, 100 µL, 0.940 mmol). N₂ was bubbled through the reaction mixture for 4 min. The vial was capped and heated at 105° C. for 14 hours. The reaction mixture was diluted with MeOH (10 mL), the resulting precipitate was collected and washed with warm MeOH (3×10 mL). The mother liquor was concentrated and purified using column chromatography (40 g SiO₂, 0% to 10% MeOH-EtOAc) to give the title compound (305 mg, 73%) as a brown solid. LCMS (M+H)=178.0: HPLC RT=0.857 min (Column: YMC CombiScreen ODS-A 4.6×50 mm; Mobile Phase A: 10:90 MeOH:water with 0.2% H₃PO₄; Mobile Phase B: 90:10 MeOH:water with 0.2% H₃PO₄; Gradient: 0-100% B over 4 min; Flow: 4 mL/min).

Step 2: N-{3-fluoro-4-[(2-{[5-(2-oxopyrrolidin-1-yl) pyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide To a 4 mL vial containing N-(4-((2-chloropyridin-4-yl)oxy)-3-fluorophenyl)-3-(4-fluorophenyl)-1-isopropyl-2,4-dioxo-1,2,3,4-tetrahydropyrimidine-5-carboxamide (27 mg, 0.052 mmol), 1-(6-aminopyridin-3-yl)pyrrolidin-2-one (14 mg, 0.079 mmol), Xantphos (3.6 mg, 6.3 µmol), Cs₂CO₃ (51 mg, 0.16 mmol) and Pd₂(dba)₃ (4.8 mg, 5.2 µmol) was added degassed Dioxane (524 µL). The resulting reaction mixture was stirred under a N₂ atmosphere at 100° C. for 2 hours and then concentrated. The residue was purified using preparative LC/MS (Column: Xbridge C18, 19×200 mm, 5 µM; Mobile Phase A: 5:95 acetonitrile:water with 10 mM ammonium acetate; Mobile Phase B: 95:5 acetonitrile:water with 10 mM ammonium acetate; Gradient: 32-72% B over 20 minutes, then a 4-minute hold at 100% B: Flow: 20 mL/min) to give the titled compound (9.5 mg, 27%) upon centrifugal evaporation. 1H NMR (500 MHz, DMSO-d₆) δ 11.03-10.95 (m, 1H), 9.65 (s, 1H), 8.65 (s, 1H), 8.37 (d, J=2.1 Hz, 1H), 8.09 (d, J=5.8 Hz, 1H), 7.99-7.90 (m, 2H), 7.74 (d, J=9.2 Hz, 1H), 7.46 (br d, J=8.2 Hz, 1H), 7.44-7.38 (m, 2H), 7.38-7.30 (m, 3H), 7.25 (s, 1H), 6.47-6.41 (m, 1H), 4.77 (dt, J=13.4, 6.7 Hz, 1H), 3.79 (t, J=7.0 Hz, 2H), 2.45 (t, J=8.1 Hz, 2H), 2.06 (quin, J=7.6 Hz, 2H), 1.42 (s, 3H), 1.41 (s, 3H); LCMS (M+H)=654.3: HPLC RT=1.73 min (Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.: Gradient: 0% B to 100% B over 3 min, then a 0.75 min hold at 100% B; Flow: 1 mL/min, Detection: MS and UV (220 nm).

Examples 89 to 91

The compounds in Table 6 were prepared according to the procedures described for Example 88.

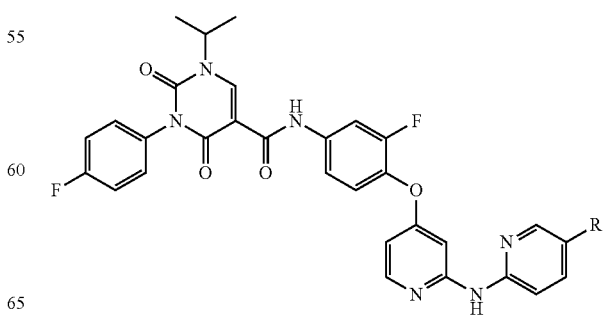

TABLE 6

| Ex. No. | R | HPLC RT (min) | LC/MS (M + H) | HPLC Method |
|---|---|---|---|---|
| 89 | ![structure] | 7.75 | 769.5 | A |
| 90 | ![structure] | 5.74 | 669.4 | A |
| 91 | ![structure] | 1.92 | 711.2 | B |

HPLC Conditions for Table 6:

Method A; Column: Sunfire C18, 3.0 mm×150 mm, 3.5 μm particles; Mobile Phase A: 5:95 acetonitrile:water with 0.05% trifluoroacetic acid; Mobile Phase B: 95:5 acetonitrile:water with 0.05% trifluoroacetic acid; Gradient: 10% B to 100% B over 12 min, then a 3 min hold at 100% B: Flow: 0.5 mL/min; Detection; UV (220 nm) Method B; Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm)

Example 92

N-(3-Fluoro-4-{[2-({5-[(2-hydroxy-2-methylpropyl)carbamoyl]pyridin-2-yl}amino)pyridin-4-yl]oxy}phenyl)-3-(4-fluorophenyl)-2,4-dioxo-1-(propan-2-yl)-1,2,3,4-tetrahydropyrimidine-5-carboxamide

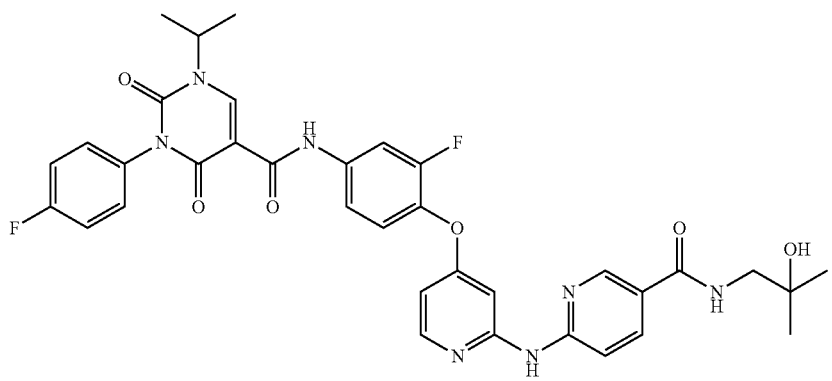 [SMILES: CC(C)n1cc(C(=O)Nc2ccc(Oc3ccnc(Nc4ccc(C(=O)NCC(C)(C)O)cn4)c3)c(F)c2)c(=O)n(-c2ccc(F)cc2)c1=O]

Step 1. 6-((4-(2-Fluoro-4-(3-(4-fluorophenyl)-1-isopropyl-2,4-dioxo-1,2,3,4-tetrahydropyrimidine-5-carboxamido)phenoxy)pyridin-2-yl)amino)nicotinic acid Methyl 6-((4-(2-fluoro-4-(3-(4-fluorophenyl)-1-isopropyl-2,4-dioxo-1,2,3,4-tetrahydropyrimidine-5-carboxamido)phenoxy)pyridin-2-yl)amino)nicotinate (115 mg, 0.183 mmol, Example 14) was dissolved in 4N HCl-dioxane (1000 μl, 4.00 mmol). $H_2O$ (200 μl) was added and the reaction mixture was heated to 70° C. for 16 h. Fresh of 4N HCl-Dioxane (500 μL) was added and the reaction was stirred at 70° C. for an additional 4 h before cooling to rt. The expected product was precipitated from the reaction mixture by the addition of $H_2O$ to provide the titled product (59.5 mg, 53% yield). LC/MS (M+H) 615.5; LC RT=0.92 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 2. N-(3-Fluoro-4-{[2-({5-[(2-hydroxy-2-methylpropyl)carbamoyl]pyridin-2-yl}amino)pyridin-4-yl]oxy}phenyl)₃-(4-fluorophenyl)-2,4-dioxo-1-(propan-2-yl)-1,2,3,4-tetrahydropyrimidine-5-carboxamide 6-((4-(2-Fluoro-4-(3-(4-fluorophenyl)-1-isopropyl-2,4-dioxo-1,2,3,4-tetahydropyrimidine-5-carboxamido)phenoxy)pyridin-2-yl)amino)nicotinic acid (10 mg, 0.016 mmol) in NMP (163 µl) was treated with 1-amino-2-methylpropan-2-ol (1.450 mg, 0.016 mmol) and TEA (3.40 µl, 0.024 mmol). HATU (7.42 mg, 0.020 mmol) was added and the reaction mixture was stirred at rt for 90 min. After diluting with DMF, the reaction mixture was directly purified via preparative LC/MS with the following conditions; Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 30% B, 30-700% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to afford the titled product (4.5 mg, 39% yield). 1H NMR (500 MHz, DMSO-d₆) δ 11.03 (s, 1H), 10.02 (s, 1H), 8.67 (s, 1H), 8.63 (s, 1H), 8.25-8.14 (m, 2H), 8.11-8.04 (m, 1H), 8.03-7.94 (m, 1H), 7.75 (d, J=8.5 Hz, 1H), 7.57-7.31 (m, 7H), 6.59-6.49 (m, 1H), 4.78 (quin, J=6.7 Hz, 1H), 3.24 (br d, J=6.1 Hz, 1H), 1.43 (br d, J=6.7 Hz, 6H), 1.10 (s, 6H). LC/MS (M+H) 686.42; HPLC RT=1.92 min; Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Examples 93 to 96

The compounds in Table 7 were prepared according to the procedures described for Example 92.

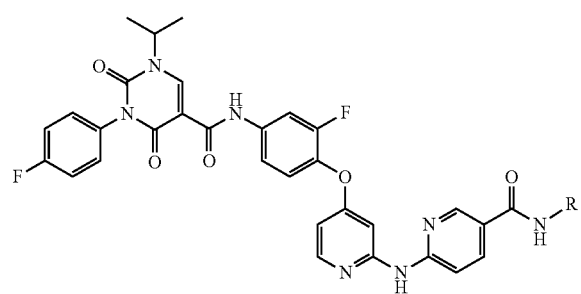

TABLE 7

| Ex. No. | R¹ | HPLC RT (min) | LC/MS (M + H) | HPLC Method |
|---|---|---|---|---|
| 93 | (morpholinopropyl) | 1.919 | 727.36 | A |
| 94 | (isobutyl) | 2.207 | 656.33 | A |
| 95 | (2,2-difluoroethyl-methyl) | 2.065 | 678.37 | A |
| 96 | (isopropylsulfonyl) | 1.749 | 720.24 | A |

HPLC Conditions for Table 7:
Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Example 97

N-{4-[(2-{[5-(Dimethylcarbamoyl)-6-(4-methanesulfonylpiperazin-1-yl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide

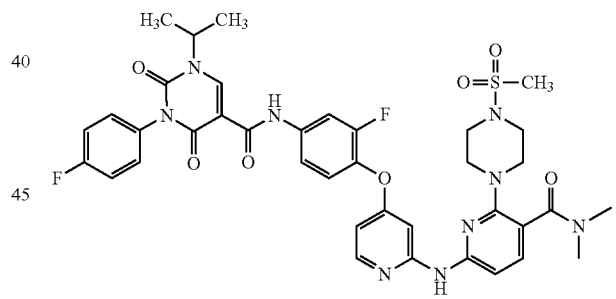

Step 1. 2,6-Dichloro-N,N-dimethylnicotinamide 2,6-Dichloronicotinoyl chloride (500 mg, 2.376 mmol) was dissolved in THF and cooled to 0° C. TEA (0.662 mL, 4.75 mmol) was added followed by the dropwise addition of dimethylamine (2M in THF) (1.188 mL, 2.376 mmol). The reaction was stirred at 0° C. for 1 hour, then poured into a separatory funnel containing CH₂Cl₂ and H₂O. The reaction product was extracted into CH₂Cl₂ (3×). The combined organic phases were washed with brine, dried over MgSO4 and concentrated to afford 2,6-dichloro-N,N-dimethylnicotinamide (404.2 mg 78% yield)

Step 2. 6-Chloro-N,N-dimethyl-2-(4-(methylsulfonyl)piperazin-1-yl)nicotinamide 2,6-Dichloro-N,N-dimethylnicotinamide (100 mg, 0.456 mmol), 1-(methylsulfonyl)piperazine (75.0 mg, 0.456 mmol) and potassium carbonate (63.1 mg, 0.456 mmol) were suspended in DMA (2.3 mL) at rt. The reaction mixture was heated to 105° C. and stirred overnight. After cooling to rt, the reaction mixture was partitioned between EtOAc and H2O, extracting with EtOAc (3×). The combined organic phases were washed with 10% aqeuous LiCl solution, dried over $Na_2SO_4$ and concentrated. Column chromatography (12 g SiO2, 0 to 100% EtOAc-hexane gradient elution) afforded the expected product (62.8 mg, 40% yield). 1H NMR (500 MHz, DMSO-$d_6$) δ 7.55 (d, J=7.8 Hz, 1H), 6.94 (d, J=7.7 Hz, 1H), 3.46-3.37 (m, 4H), 3.24-3.14 (m, 4H), 3.00 (s, 3H), 2.93 (s, 3H), 2.85 (s, 3H).

Step 3. N-(4-((2-aminopyridin-4-yl)oxy)-3-fluorophenyl)-3-(4-fluorophenyl)-1-isopropyl-2,4-dioxo-1, 2,3,4-tetrahydropyrimidine-5-carboxamide To a solution of N-(4-((2-chloropyridin-4-yl)oxy)-3-fluorophenyl)-3-(4-fluorophenyl)-1-isopropyl-2,4-dioxo-1,2,3, 4-tetrahydropyrimidine-5-carboxamide (375 mg, 0.731 mmol, Example 1, Step 7) in DMA (1 mL) was added a suspension of tert-butyl carbamate (171 mg, 1.462 mmol) and potassium carbonate (303 mg, 2.193 mmol) in tBuOH (6 mL). The reaction mixture was purged with a stream of $N_2$ for several minutes before the addition of BrettPhos Precatalyst—G1 (73.1 mg, 0.073 mmol). The reaction vial was then sealed and heated to 120° C. After 90 minutes, the reaction was cooled to room temperature and diluted with H2O. Collected the resulting solid was collected by filtration and air dried. The crude intermediate was dissolved in 50% TFA-$CH_2CL_2$ (6 mL) and stirred at rt for 90 minutes. Concentration and purification by column chromatography (40 g SiO2, 0 to 15% $CH_3OH$—$CH_2Cl_2$ gradient elution) afforded an amber oil which was triturated with $Et_2O$ to afford the titled product as a tan solid (193.2 mg 54% yield). 1H NMR (4(0) MHz, DMSO-$d_6$) δ 11.07 (s, 1H), 8.68 (s, 1H), 8.05 (dd, J=12.9, 2.3 Hz, 1H), 7.97 (d, J=7.2 Hz, 1H), 7.82-7.71 (m, 1H), 7.64-7.55 (m, 1H), 7.51-7.31 (m, 5H), 6.72 (dd, J=7.2, 2.5 Hz, 1H), 6.16 (d, J=2.4 Hz, 1H), 4.91-4.68 (m, 1H), 1.43 (d, J=6.8 Hz, 6H).

Step 4. N-{4-[(2-{[5-(Dimethylcarbamoyl)-6-(4-methanesulfonylpiperazin-1-yl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide N-(4-((2-Aminopyridin-4-yl)oxy)-3-fluorophenyl)-3-(4-fluorophenyl)-1-isopropyl-2,4-dioxo-1,2,3,4-tetrahydropyrimidine-5-carboxamide (30 mg, 0.061 mmol), 6-chloro-N,N-dimethyl-2-(4-(methylsulfonyl)piperazin-1-yl) nicotinamide (21.09 mg, 0.061 mmol), and potassium carbonate (25.2 mg, 0.182 mmol) were suspended in tBuOH/DMA (6:1) (608 μl) at rt. The reaction mixture was purged with a stream of $N_2$ for 2 minutes before the addition of Brettphos precatalyst (4.86 mg, 6.08 μmol). The reaction mixture was purged for another 60 s then sealed and heated to 110° C. using microwave irradiation for 45 minutes. After cooling to rt, the reaction mixture was diluted with EtOAc and filtered through at 0.45 μm PTFE cartridge. The crude material was purified via preparative LC/MS with the following conditions; Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 34% B, 34-74% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to afford the expected product (2.8 mg, 6% yield). 1H NMR (500 MHz, DMSO-d6) δ 10.95 (s, 1H), 9.67 (s, 1H), 8.68-8.54 (m, 1H), 8.14 (d, J=5.8 Hz, 1H), 7.93 (br d, J=13.4 Hz, 1H), 7.46-7.27 (m, 8H), 7.05 (br d, J=8.2 Hz, 1H), 6.61-6.51 (m, 1H), 4.90-4.67 (m, 1H), 3.16-3.04 (m, 7H), 3.00-2.92 (m, 3H), 2.87 (s, 3H), 2.82 (s, 3H), 1.42 (br d, J=6.4 Hz, 6H). LC/MS (M+H) 804.53: HPLC RT 1.97 min. Column: Waters XBridge C18, 2.1 mm×50 mm, 1.7 pun particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Example 98

N-{4-[(2-{[6-(dimethylamino)-N,N-(dimethylsulfamoyl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide

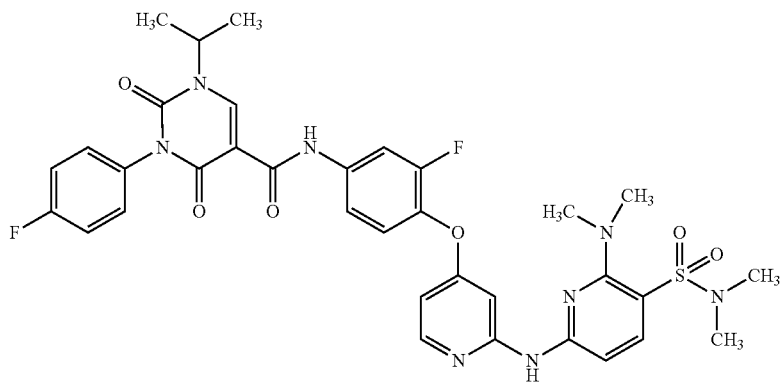 [SMILES: CC(C)n1cc(C(=O)Nc2ccc(Oc3ccnc(Nc4ccc(S(=O)(=O)N(C)C)c(N(C)C)n4)c3)c(F)c2)c(=O)n(-c2ccc(F)cc2)c1=O]

Step 1: 6-Chloro-2-(dimethylamino)-N,N-dimethylpyridine-3-sulfonamide

A 25 mL flask containing 2,6-dichloropyridine-3-sulfonyl chloride (Enamine, 213 mg, 0.865 mmol), Et₃N (ChemImpex, 145 μl, 1.04 mmol)) and THF (8.7 mL) was cooled to −20° C. and a 2 M solution of dimethylamine in THF (Aldrich, 454 μl, 0.908 mmol) was added. The reaction mixture was stirred at −20° C. for 2 hours and then at room temperature for 3 hours. The reaction mixture was concentrated and purified by column chromatography (12 g SiO₂, 0 to 20% EtOAc-hexanes, gradient elution) to isolate the minor product—6-Chloro-2-(dimethylamino)-N,N-dimethylpyridine-3-sulfonamide (34 mg, 15%) as a white solid. ¹H NMR (400 MHz, CHLOROFORM-d) δ 7.93-7.82 (m, 1H), 6.79 (d, J=8.1 Hz, 1H), 3.11 (s, 6H), 2.83 (s, 6H); LCMS (M+H)=264.2; LC RT 0.90 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 2: N-(4-((2-((6-(dimethylamino)-5-(N,N-dimethylsulfamoyl)pyridin-2-yl)amino)pyridin-4-yl)oxy)₃-fluorophenyl)-3-(4-fluorophenyl)-1-isopropyl-2,4-dioxo-1,2,3,4-tetrahydropyrimidine-5-carboxamide To a 4 mL vial containing N-(4-((2-aminopyridin-4-yl)oxy)-3-fluorophenyl)-3-(4-fluorophenyl)-1-isopropyl-2,4-dioxo-1,2,3,4-tetrahydropyrimidine-5-carboxamide (22 mg, 0.045 mmol, Example 97—Step 3), 6-chloro-2-(dimethylamino)-N,N-dimethylpyridine-3-sulfonamide (18 mg, 0.067 mmol), Xantphos (3.1 mg, 5.4 μmol), Cs₂CO₃ (44 mg, 0.14 mmol) and Pd₂(dba)₃ (4.1 mg, 4.5 μmol) was added degassed Dioxane (446 μl). The resulting reaction mixture was stirred under a N₂ atmosphere at 110° C. for 2 hours and then concentrated. The residue was purified using preparative LC/MS (Column: Xbridge C18, 19×200 mm, 5 μM; Mobile Phase A: 5:95 acetonitrile; water with 0.1% TFA; Mobile Phase B: 95:5 acetonitrile:water with 0.1% TFA; Gradient: 29-69% B over 20 minutes, then a 4-minute hold at 100% B; Flow: 20 mL/min) to give the product (1.9 mg, 6%) upon centrifugal evaporation. ¹H NMR (500 MHz, DMSO-d₆) δ 11.03-10.96 (m, 1H), 8.64 (s, 1H), 8.19 (d, J=5.8 Hz, 1H), 7.94 (br d, J=13.1 Hz, 1H), 7.76 (d, J=8.5 Hz, 1H), 7.57 (s, 1H), 7.47-7.43 (m, 1H), 7.40 (br d, J=4.9 Hz, 2H), 7.37-7.31 (m, 3H), 7.27 (s, 1H), 6.82 (d, J=8.9 Hz, 1H), 6.74 (dd, J=5.6, 2.0 Hz, 1H), 4.80-4.66 (m, 1H), 2.63 (s, 6H), 2.60 (s, 6H), 1.41 (s, 3H), 1.40 (s, 3H). LCMS (M+H) =721.1; HPLC RT=1.87 min (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Example 99

N-{4-[(2-{[5-(dimethylsulfamoyl)-6-(4-methanesulfonylpiperazin-1-yl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide

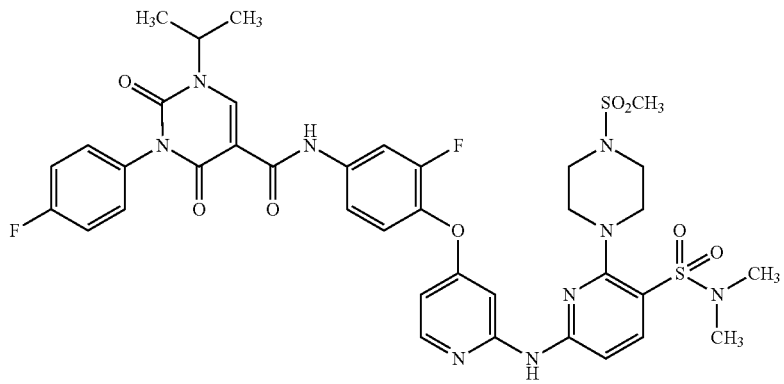 [SMILES: CC(C)n1cc(C(=O)Nc2ccc(Oc3ccnc(Nc4ccc(S(=O)(=O)N(C)C)c(N5CCN(S(C)(=O)=O)CC5)n4)c3)c(F)c2)c(=O)n(-c2ccc(F)cc2)c1=O]

Step 1: 2,6-dichloro-N,N-dimethylpyridine-3-sulfonamide

A 25 mL flask containing 2,6-dichloropyridine-3-sulfonyl chloride (Enamine, 213 mg, 0.865 mmol), Et₃N (ChemImpex, 145 μl, 1.04 mmol)) and THF (8.7 mL) was cooled to −20° C. and a 2 M solution of dimethylamine in THF (Aldrich, 454 μl, 0.908 mmol) was added. The reaction mixture was stirred at −20° C. for 2 hours and then at room temperature for 3 hours. The reaction mixture was concentrated and purified by column chromatography (12 g SiO₂, 0 to 20% EtOAc-hexanes, gradient elution) to isolate the major product—2,6-dichloro-N,N-dimethylpyridine-3-sulfonamide (124 mg, 56%). 1H NMR (400 MHz, CHLOROFORM-d) δ 8.42-8.27 (m, 1H), 7.42 (d, J=8.1 Hz, 1H), 2.95 (s, 6H). LCMS (M+H)=255.1.

Step 2: 6-Chloro-N,N-dimethyl-2-(4-(methylsulfonyl)piperazin-1-yl)pyridine-3-sulfonamide To a 7 mL vial containing a mixture of 2,6-dichloro-N,N-dimethylpyridine-3-sulfonamide (31 mg, 0.12 mmol), 1-(methylsulfonyl)piperazine (20 mg, 0.12 mmol) and THF (1227 μl) was added Et₃N (20.52 μl, 0.147 mmol). The reaction mixture was stirred overnight at 60° C. After cooling to 22° C., the reaction mixture was concentrated and the residue purified using ISCO silica gel chromatography (12 g column, gradient from 0% to 70% EtOAc/Hexanes) to give the title compound (34 mg, 73%) as a white solid. ¹H NMR (400 MHz, CHLOROFORM-d) δ 8.08-7.97 (m, 1H), 7.08 (d, J=8.2 Hz, 1H), 3.58-3.49 (m, 4H), 3.43-3.38 (m, 4H), 2.84 (s, 3H), 2.79 (s, 6H), 2.83 (s, 6H). LCMS (M+H)=383.3.

Step 3: N-(4-((2-((5-(N,N-dimethylsulfamoyl)-6-(4-(methylsulfonyl)piperazin-1-yl)pyridin-2-yl)amino)pyridin-4-yl)oxy)-3-fluorophenyl)-3-(4-fluorophenyl)-1-isopropyl-2,4-dioxo-1,2,3,4-tetrahydropyrimidine-5-carboxamide To a 1 dram vial was added N-(4-((2-aminopyridin-4-yl)oxy)-3-fluorophenyl)-3-(4-fluorophenyl)-1-isopropyl-2,4-dioxo-1,2,3,4-tetrahydropyrimidine-5-carboxamide (32 mg, 0.065 mmol), 6-chloro-N,N-dimethyl-2-(4-(methylsulfonyl)piperazin-1-yl)pyridine-3-sulfonamide (29.8 mg, 0.078 mmol), Xantphos (4.50 mg, 7.78 μmol), Cs$_2$CO$_3$ (63.4 mg, 0.195 mmol), Pd$_2$(dba)$_3$ (5.94 mg, 6.48 μmol)) and Dioxane (648 μl). The reaction mixture was degassed with a stream of N$_2$, then heated to 100° C. for 2 hours. The reaction mixture was cooled to rt and concentrated. The residue taken up in DMF, filtered purified by preparative LC/MS (Column: Xbridge C18, 19×200 mm, 5 μM; Mobile Phase A: 5:95 acetonitrile:water with 0.1% TFA; Mobile Phase B: 95:5 acetonitrile:water with 0.1% TFA; Gradient: 27-67% B over 20 minutes, then a 4-minute hold at 100% B: Flow: 20 mL/min) to give N-(4-((2-((5-(N,N-dimethylsulfamoyl)-6-(4-(methylsulfonyl)piperazin-1-yl)pyridin-2-yl)amino)pyridin-4-yl)oxy)-3-fluorophenyl)-3-(4-fluorophenyl)-1-isopropyl-2,4-dioxo-1,2,3,4-tetrahydropyrimidine-5-carboxamide (15.5 mg, 29%) upon centrifugal evaporation. $^1$H NMR (500 MHz, DMSO-d$_6$) δ 10.93 (s, 1H), 8.60 (s, 1H), 8.22 (d, J=5.8 Hz, 1H), 7.98-7.85 (m, 2H), 7.44-7.31 (M, 7H), 7.27-7.23 (m, 1H), 6.74-6.66 (m, 1H), 4.75 (dt, J=13.6, 6.6 Hz, 1H), 3.62 (br s, 1H), 3.16 (br s, 4H), 3.10 (br s, 4H), 2.86 (s, 3H), 2.59 (s, 6H), 1.40 (s, 3H), 1.39 (s, 3H). LCMS (M+H)=840.5. HPLC RT=1.83 min (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Examples 100 to 101

The compounds in Table 8 were prepared according to the procedures described for Example 99.

TABLE 8

| Ex. No. | R$^3$ | HPLC RT (min) | LC/MS (M + H) | HPLC Method |
|---|---|---|---|---|
| 100 | 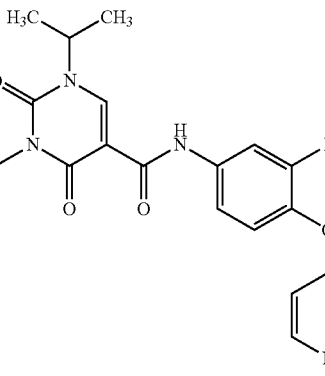 CO$_2$Me | 2.26 | 820.04 | A |
| 101 | SO$_2$Me | 2.13 | 839.48 | A |

HPLC Conditions for Table 8:

Method A Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min. then a 0.75 min hold at 100% B: Flow: 1 L/min; Detection: MS and UV (220 nm).

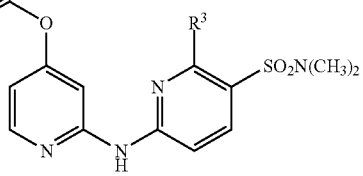

Example 102

N-{3-fluoro-4-[(2-{[2-(4-methanesulfonylpiperazin-1-yl)pyrimidin-4-yl]amino}pyridin-4-yl)oxy]phenyl}-3-(4-fluorophenyl)-2,4-dioxo-1-(propan-2-yl)-1,2,3,4-tetrahydropyrimidine-5-carboxamide

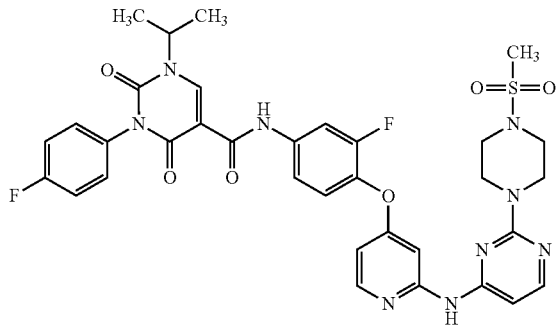 [SMILES: CC(C)n1cc(C(=O)Nc2ccc(Oc3ccnc(Nc4ccnc(N5CCN(S(C)(=O)=O)CC5)n4)c3)c(F)c2)c(=O)n(-c2ccc(F)cc2)c1=O]

Step 1. N-(4-(2-fluoro-4-nitrophenoxy)pyridin-2-yl)-2-(4-(methylsulfonyl)piperazin-1-yl)pyrimidin-4-amine 2-Chloro-4-(2-fluoro-4-nitrophenoxy)pyridine (156 mg, 0.581 mmol), 2-(4-(methylsulfonyl)piperazin-1-yl)pyrimidin-4-amine (197 mg, 0.766 mmol), $Cs_2CO_3$ (782 mg, 2.400 mmol), and BrettPhos (74.1 mg, 0.138 mmol) were suspended in dioxane (3.0 mL) at rt. The reaction mixture was purged with $N_2$ for 1 min before the addition of $Pd_2(dba)_3$ (152 mg, 0.166 mmol). The reaction mixture was heated to 105° C. for 90 min. After cooling to rt, the reaction was partitioned between EtOAc and brine, and extracted with two additional portions of EtOAc. The combined organic phases were dried over $Na_2SO_4$ and concentrated. Column chromatography (24 g SiO2, 0 to 10% MeOH—$CH_2Cl_2$ gradient elution) afforded the expected product (91 mg, 32% yield). 1H NMR (400 MHz, CHLOROFORM-d) δ 8.22 (d. J=5.6 Hz, 1H), 8.09 (d, J=5.6 Hz, 1H), 7.76 (br d, J=2.3 Hz, 1H), 7.62 (dd, J=6.7, 2.9 Hz, 1H), 7.58 (d, J=2.1 Hz, 1H), 7.41 (d, J=2.6 Hz, 1H), 7.38-7.31 (m, 1H), 6.55 (dd, J=5.7, 2.2 Hz, 1H), 6.42 (d, J=5.6 Hz, 1H), 3.86-3.79 (m, 4H), 3.25-3.16 (m, 4H), 2.78 (s, 3H); LCMS (M+H) 459.8; LC RT 0.60 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 2. N-(4-(4-amino-2-fluorophenoxy)pyridin-2-yl)-2-(4-(methylsulfonyl)piperazin-1-yl)pyrimidin-4-amine N-(4-(2-fluoro-4-nitrophenoxy)pyridin-2-yl)-2-(4-(methylsulfonyl)piperazin-1-yl)pyrimidin-4-amine (650 mg, 1.328 mmol) was suspended in MeOH (25 mL) at rt. DCM (15 mL) was added until it became homogeneous. Ammonium chloride (2273 mg, 42.5 mmol) was added followed by the addition of zinc (1823 mg, 27.9 mmol). The reaction was stirred at rt for 2 h then diluted with MeOH (120 mL), filtered through celite and concentrated. The crude material was partitioned between EtOAc and a 50/50 mixture of sat. aq. NaCl/sat. aq. $NaHCO_3$. The product was extracted into EtOAc (3×60 mL). The combined organic phases were dried over $Na_2SO_4$ and concentrated to afford N-(4-(4-amino-2-fluorophenoxy)pyridin-2-yl)-2-(4-(methylsulfonyl)piperazin-1-yl)pyrimidin-4-amine as a light yellow solid (583 mg, 96%). LCMS (M+H)=459.8; LC RT 0.60 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 3. N-(3-fluoro-4-((2-((2-(4-(methylsulfonyl)piperazin-1-yl)pyrimidin-4-yl)amino)pyridin-4-yl)oxy)phenyl)-3-(4-fluorophenyl)-1-isopropyl-2,4-dioxo-1,2,3,4-tetrahydropyrimidine-5-carboxamide N-(4-(4-amino-2-fluorophenoxy)pyridin-2-yl)-2-(4-(methylsulfonyl)piperazin-1-yl)pyrimidin-4-amine (20 mg, 0.044 mmol) and 3-(4-fluorophenyl)-1-isopropyl-2,4-dioxo-1,2,3,4-tetrahydropyrimidine-5-carboxylic acid (12.72 mg, 0.044 mmol) were dissolved in DMF (435 µl) at rt. HATU (24.82 mg, 0.065 mmol) was added, followed by DIPEA (22.81 µl, 0.131 mmol). The reaction mixture was stirred at room temperature for 90 minutes, then diluted with DMF (500 µL). The crude material was purified via preparative LC/MS with the following conditions; Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 5-minute hold at 100% B: Flow: 20 mL/min. Fractions containing the desired product were combined and dried via centrifugal evaporation to afford the titled compound (11.1 mg, 34% yield). 1H NMR (500 MHz, DMSO-$d_6$) δ 10.98 (s, 1H), 9.85 (s, 1H), 8.60 (s, 1H), 8.18 (d, J=5.8 Hz, 1H), 8.01 (d, J=5.5 Hz, 1H), 7.98-7.87 (m, 2H), 7.51-7.28 (m, 7H), 6.81-6.69 (m, 1H), 6.64 (br d, J=4.6 Hz, 1H), 4.76 (dt, J=13.3, 6.8 Hz, 1H), 3.02 (br s, 3H), 2.80 (s, 3H), 1.40 (br d, J=6.7 Hz, 6H); LC/MS (M+H)=734.16; HPLC RT=2.17 min; Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Example 103

N-{3-fluoro-4-[(2-{[2-(pyrrolidin-1-yl)pyrimidin-4-yl]amino}pyridin-4-yl)oxy]phenyl}-3-(4-fluorophenyl)-2,4-dioxo-1-(propan-2-yl)-1,2,3,4-tetrahydropyrimidine-5-carboxamide

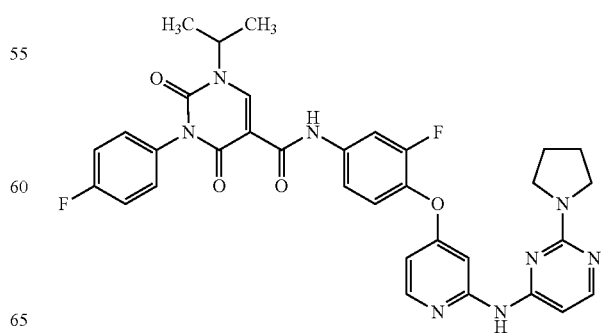

Step 1. 2-(Pyrrolidin-1-yl)pyrimidin-4-amine

In a 20 ml vial was added a suspension of 4-amino-2-chloropyrimidine (1.5 g, 11.58 mmol) and pyrrolidine (4.79 ml, 57.9 mmol). The mixture was heated in a heating block at 120° C. for 1.5 h. After cooling to room temperature, the reaction mixture was diluted with DCM and concentrated. The residue was diluted with DCM and washed with aq NH$_4$OH solution and reconcentrated to obtain 2-(pyrrolidin-1-yl)pyrimidin-4-amine (1.9 g, 11.57 mmol, 100% yield) as a tan-yellow solid. 1H NMR (400 MHz, DMSO-d$_6$) δ 7.70 (d, J=5.6 Hz, 1H), 6.28 (br. s., 2H), 5.68 (d, J=5.7 Hz, 1H), 3.41-3.35 (m, 4H), 1.88-1.83 (m, 4H). LC/MS [M+H] =164.9; LC RT=0.48 min. (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 2. N-(4-(2-fluoro-4-nitrophenoxy)pyridin-2-yl)-2-(pyrrolidin-1-yl)pyrimidin-4-amine In a 40 mL reaction vial, 2-chloro-4-(2-fluoro-4-nitrophenoxy)pyridine (1.1 g, 4.09 mmol), 2-(pyrrolidin-1-yl)pyrimidin-4-amine (0.787 g, 4.79 mmol), BrettPhos Precatalyst chloro[2-(dicyclohexylphosphino)-3,6-dimethoxy-2',4',6'-tri-1-propyl-1,1'-biphenyl][2-(2-aminoethyl)phenyl]palladium(1) (0.327 g, 0.409 mmol), tris(dibenzylideneacetone)dipalladium(0) (0.375 g, 0.409 mmol), and Cs$_2$CO$_3$ (2.67 g, 8.19 mmol) were suspended in Dioxane (25 mL) and degassed by sparging with a stream of nitrogen for 3 minutes. The reaction vial was sealed and heated to 105° C. After 3 hours, no starting materials remained by LC/MS. The reaction mixture was cooled to room temperature, diluted with H$_2$O and extracted into EtOAc (3×20 mL). The combined organics were washed with H$_2$O and concentrated. Column chromatography (40 g SiO2, 100% EtOAc) afforded N-(4-(2-fluoro-4-nitrophenoxy)pyridin-2-yl)-2-(pyrrolidin-1-yl)pyrimidin-4-amine (0.565 g, 1.425 mmol, 34.8% yield) as a light-yellow solid. 1H NMR (400 MHz, DMSO-d$_6$) δ 9.97 (s, 1H), 8.48 (dd, J=10.5, 2.7 Hz, 1H), 8.27 (d, J=5.6 Hz, 1H), 8.26-8.22 (m, 1H), 8.01 (d, J=2.1 Hz, 1H), 7.95 (d, J=5.6 Hz, 1H), 7.71 (t, J=8.6 Hz, 1H), 6.87 (dd, J=5.6, 2.4 Hz, 1H), 6.35 (d, J=5.6 Hz, 1H), 3.45-3.21 (br. s, 2H), 2.78 (br. s., 2H), 1.71 (br. s., 4H). LC/MS [M+H]=396.8; LC RT=0.73 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 3. N-(4-(4-amino-2-fluorophenoxy)pyridin-2-yl)-2-(pyrrolidin-1-yl)pyrimidin-4-amine N-(4-(2-fluoro-4-nitrophenoxy)pyridin-2-yl)-2-(pyrrolidin-1-yl)pyrimidin-4-amine (0.57 g, 1.438 mmol) was dissolved in Methanol (15 mL)/Dichloromethane (5 mL) at room temperature. Ammonium chloride (2.308 g, 43.1 mmol) and zinc dust (1.880 g, 28.8 mmol) were added and the reaction was stirred at rt for 3 h. The reaction mixture was diluted with EtOAc and filtered through a pad of celite. The organic phase was washed sequentially with sat. aq. NaHCO$_3$ solution, water and brine. Concentration afforded N-(4-(4-amino-2-fluorophenoxy)pyridin-2-yl)-2-(pyrrolidin-1-yl)pyrimidin-4-amine (0.432 g, 1.179 mmol, 82% yield) as a light-yellow solid. LC/MS [M+H]+=366.8; LC RT=0.63 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 4. N-{3-fluoro-4-[(2-{[2-(pyrrolidin-1-yl)pyrimidin-4-yl]amino}pyridin-4-yl)oxy]phenyl}-3-(4-fluorophenyl)-2,4-dioxo-1-(propan-2-yl)-1,2,3,4-tetrahydropyrimidine-5-carboxamide N-(4-(4-amino-2-fluorophenoxy)pyridin-2-yl)-2-(pyrrolidin-1-yl)pyrimidin-4-amine (20 mg, 0.055 mmol), 3-(4-fluorophenyl)-1-isopropyl-2,4-dioxo-1,2,3,4-tetrahydropyrimidine-5-carboxylic acid (15.95 mg, 0.055 mmol) and HATU (31.1 mg, 0.082 mmol) were dissolved in DMF (546 µl) at rt. DIPEA (28.6 µl, 0.164 mmol) was added and the reaction was stirred at rt for 16 hr. The reaction mixture was diluted with DMF and directly purified by preparative LC/MS with the following conditions; Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 4-minute hold at 100% B; Flow: 20 mL/min. Fractions containing the desired product were combined and dried via centrifugal evaporation to afford the titled compound (23.5 mg, 67% yield). 1H NMR (500 MHz, DMSO-d$_6$) δ 11.01 (s, 1H), 9.77 (s, 1H), 8.64 (s, 1H), 8.16 (d, J=5.5 Hz, 1H), 8.06-7.81 (m, 4H), 7.48-7.21 (m, 6H), 6.74 (dd, J=5.5, 2.1 Hz, 1H), 6.27 (br d, J=5.5 Hz, 1H), 4.76 (dt, J=13.5, 6.8 Hz, 1H), 1.72 (br s, 4H), 1.41 (br d, J=6.7 Hz, 6H); LC/MS [M+H] 641.33; HPLC RT 2.07 min; Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Example 104

3-(Bicyclo[1.1.1]pentan-1-yl)-N-(3-fluoro-4-((2-((2-(pyrrolidin-1-yl)pyrimidin-4-yl)amino)pyridin-4-yl)oxy)phenyl)-1-isopropyl-2,4-dioxo-1,2,3,4-tetrahydropyrimidine-5-carboxamide

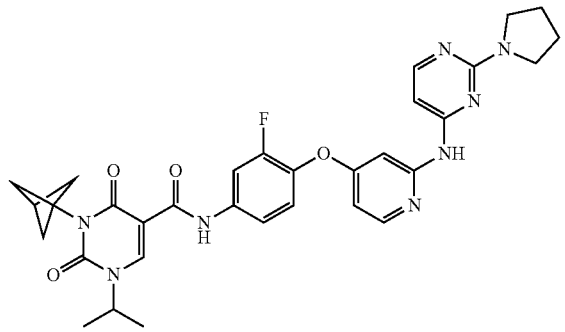 [SMILES: CC(C)n1cc(C(=O)Nc2ccc(Oc3ccnc(Nc4ccnc(N5CCCC5)n4)c3)c(F)c2)c(=O)n(C23CC(C2)C3)c1=O]

Step 1: Ethyl 3-(bicyclo[1.1.1]pentan-1-yl)-2,4-dioxo-1,2,3,4-tetrahydropyrimidine-5-carboxylate Bicyclo[1.1.1]pentan-1-amine, HCl (504 mg, 4.21 mmol) was suspended in methylene chloride (8 mL) under nitrogen. Triethylamine (1175 µl, 8.43 mmol) was added and the reaction was cooled in an ice bath. 4-Nitrophenyl chloroformate (1019 mg, 5.06 mmol) was then added. LCMS shows a prominent peak with the desired mass for product. After 4 hours, the reaction was quenched with water and extracted with methylene chloride. The organic phase was washed with brine. Drying over magnesium sulfate, filtration and evaporation provided the crude 4-nitrophenyl bicyclo[1.1.1]pentan-1-ylcarbamate (1.02 g) as a colorless solid. This material was used in the subsequent step without purification. Diethyl 2-(aminomethylene)malonate (326 mg, 1.741 mmol) and 4-nitrophenyl bicyclo[1.1.1]pentan-1-ylcarbamate (865 mg, 3.48 mmol) were dissolved in dioxane (1.5 mL). Diisopropylethylamine (608 µl, 3.48 mmol) was added and the reaction vial was sealed and heated to 70° C. overnight. The cooled reaction was diluted with ethyl acetate and washed sequentially with water, 1 N hydrochloric acid, water and brine. Drying over magnesium sulfate, filtration and evaporation provided the crude product. This material was applied to an 80 g Isco silica gel column and eluted with 0-50% ethyl acetate in hexanes. Evaporation provided diethyl 2-((3-(bicyclo[1.1.1]pentan-1-yl)ureido)methylene)malonate. This material was dissolved in ethanol (2 mL) under nitrogen. A solution of sodium ethoxide in ethanol (486 µl, 1.312 mmol) was added and the reaction stirred for ca. 1 hour. The reaction was then quenched with 5% citric acid to generate a precipitate. The solid was filtered, rinsed with water and hexanes. Air drying gave ethyl 3-(bicyclo[1.1.1]pentan-1-yl)-2,4-dioxo-1,2,3,4-tetrahydropyrimidine-5-carboxylate (125 mg, 0.499 mmol). $^1$H NMR (400 MHz, DMSO-d) δ 11.97-11.37 (m, 1H), 8.05 (s, 1H), 4.15 (q, J=7.1 Hz, 2H), 2.35 (s, 6H), 1.23 (t, J=7.1 Hz, 3H) (a peak appears to be obscured by the DMSO); LCMS (M+H)=251.2. HPLC RT 0.67 min (Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 mL/min; Mobile phase A: 100% Water, 0.05% TFA; Mobile phase B: 100% Acetonitrile, 0.05% TFA).

Step 2: Ethyl 3-(bicyclo[1.1.1]pentan-1-yl)-1-isopropyl-2,4-dioxo-1,2,3,4-tetrahydropyrimidine-5-carboxylate A reaction vial was charged with ethyl 3-(bicyclo[1.1.1]pentan-1-yl)-2,4-dioxo-1,2,3,4-tetrahydropyrimidine-5-carboxylate (125 mg, 0.499 mmol) in DMF (1 mL). Potassium carbonate (207 mg, 1.498 mmol) and 2-iodopropane (150 µl, 1.498 mmol) were added and the reaction warmed to 70° C. After 2 hours, the reaction was cooled and treated with water. The product separated as an oil. The water was decanted and the oil treated with more water. The water was decanted again and the residue was dissolved in ether. Hexane was added and the solution was slowly concentrated under a stream of nitrogen. The resultant solid was isolated by filtration to give ethyl 3-(bicyclo[1.1.1]pentan-1-yl)-1-isopropyl-2,4-dioxo-1,2,3,4-tetrahydropyrimidine-5-carboxylate (52 mg, 0.178 mmol, 35.6% yield) as an off white solid. $^1$H NMR (400 MHz, DMSO-d$_6$) δ 8.27 (s, 1H), 4.67 (quin, J=6.8 Hz, 1H), 4.20 (q, J=7.1 Hz, 2H), 2.78-2.59 (m, 1H), 2.37 (s, 6H), 1.31 (d. J=6.8 Hz, 6H), 1.26 (t, J=7.1 Hz, 3H); LCMS (M+H)=293.4. HPLC RT=0.88 min (Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA).

Step 3: 3-(Bicyclo[1.1.1]pentan-1-yl)-1-isopropyl-2,4-dioxo-1,2,3,4-tetrahydropyrimidine-5-carboxylic acid Ethyl 3-(bicyclo[1.1.1]pentan-1-yl)-1-isopropyl-2,4-dioxo-1,2,3,4-tetrahydropyrimidine-5-carboxylate (48 mg, 0.164 mmol) was dissolved in a solution of HCl in dioxane (4M, 500 µl, 2 mmol) and water (0.1 mL). The reaction was warmed to 70° C. After 3 hours, the cooled reaction was diluted with water. The resultant solid was filtered and rinsed sequentially with water and hexanes. Air drying provided 3-(bicyclo[1.1.1]pentan-1-yl)-1-isopropyl-2,4-dioxo-1,2,3,4-tetrahydropyrimidine-5-carboxylic acid (33.4 mg, 0.126 mmol, 77% yield) as a colorless solid. $^1$H NMR (400 MHz, DMSO-d$_6$) δ 12.81 (s, 1H), 8.43 (s, 1H), 4.70 (dt, J=13.6, 6.8 Hz, 1H), 2.56 (s, 1H), 2.40 (s, 6H), 1.33 (d, J=6.8 Hz, 6H); LCMS (M+H)=265.2. HPLC RT=0.87 min (Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 m/min; Mobile phase A: 100% Water, 0.05% TFA; Mobile phase B: 100% Acetonitrile, 0.05% TFA).

Step 4: 3-(Bicyclo[1.1.1]pentan-1-yl)-N-(3-fluoro-4-((2-((2-(pyrrolidin-1-yl)pyrimidin-4-yl)amino)pyridin-4-yl)oxy)phenyl)-1-isopropyl-2,4-dioxo-1,2,3,4-tetrahydropyrimidine-5-carboxamide A reaction vial was charged with N-(4-(4-amino-2-fluorophenoxy)pyridin-2-yl)-2-(pyrrolidin-1-yl)pyrimidin-4-amine (10 mg, 0.027 mmol, Example 103—Step 3) and 3-(bicyclo[1.1.1]pentan-1-yl)-1-isopropyl-2,4-dioxo-1,2,3,4-tetrahydropyrimidine-5-carboxylic acid (7.21 mg, 0.027 mmol) in DMF (0.25 mL). The reaction was initiated with the addition of triethylamine (7.61 µl, 0.055 mmol) and BOP (14.49 mg, 0.033 mmol). After stirring overnight, the reaction was diluted with DMF and purified by RP-HPLC using the following conditions; Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 50% B, 50-1000% B over 20 minutes, then a 4-minute hold at 100% B; Flow Rate: 20 mL/min; Column Temperature: 25 C. Fractions containing the desired product were combined and dried via centrifugal evaporation to give 3-(bicyclo[1.1.1]pentan-1-yl)-N-(3-fluoro-4-((2-((2-(pyrrolidin-1-yl)pyrimidin-4-yl)amino)pyridin-4-yl)oxy)phenyl)-1-isopropyl-2,4-dioxo-1,2,3,4-tetrahydropyrimidine-5-carboxamide (8.3 mg). $^1$H NMR (500 MHz, DMSO-d) δ 11.09 (s, 1H), 9.83 (s, 1H), 8.51 (s, 1H), 8.19 (br d, J=5.8 Hz, 1H), 7.98 (br d, J=12.8 Hz, 1H), 7.94-7.82 (m, 2H), 7.50 (br d, J=9.5 Hz, 1H), 7.39 (br t, J=8.9 Hz, 1H), 6.76 (br d, J=3.7 Hz, 1H), 6.33 (br d, J=5.2 Hz, 1H), 4.75 (dt, J=13.1, 6.6 Hz, 1H), 2.59 (s, 1H), 2.46 (s, 6H), 1.77 (br s, 4H), 1.37 (br d, J=6.7 Hz, 6H) (water suppression appears to have obscured some of the pyrrolidine resonances); LCMS (M+H)=613.4. HPLC RT=2.021 min Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Examples 105 to 111

The compounds in Table 9 were prepared according to the procedures described for Examples 103 and 104.

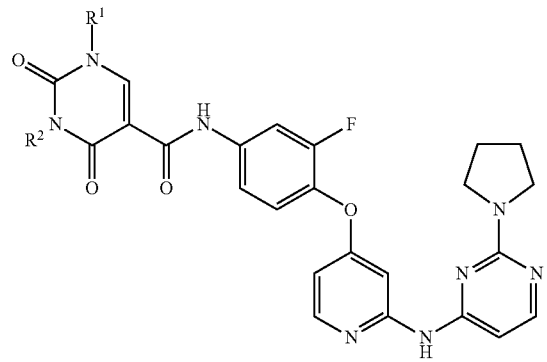

HPLC Conditions for Table 9:

Method A: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Method B; Column: Waters BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.: Gradient: 0% B, 0-100% B over 3 minutes, then a 0.75-minute hold at 100% B; Flow: 1.0 mL/min; Detection; UV at 220 nm.

TABLE 9

| Ex. No. | R¹ | R² | HPLC RT (min) | LC/MS (M + H) | HPLC Method |
|---|---|---|---|---|---|
| 105 | cyclopropyl | 4-fluorophenyl | 2.23 | 638.9 | A |
| 106 | isopropyl | phenyl | 1.882 | 637.2 | B |
| 107 | isopropyl | isobutyl | 1.969 | 603.3 | B |
| 108 | isopropyl | isopropyl | 1.942 | 589.4 | B |
| 109 | isopropyl | cyclohexyl | 2.089 | 629.2 | B |
| 110 | isopropyl | cyclopropylmethyl | 1.898 | 601.4 | B |
| 111 | isopropyl | cyclohexylmethyl | 2.279 | 643.3 | B |

Example 112

1-cyclopropyl-N-{3-fluoro-4-[(2-{[2-(4-methanesulfonylpiperidin-1-yl)pyrimidin-4-yl]amino}pyridin-4-yl)oxy]phenyl}-3-(4-fluorophenyl)-2,4-dioxo-1,2,3,4-tetrahydropyrimidine-5-carboxamide

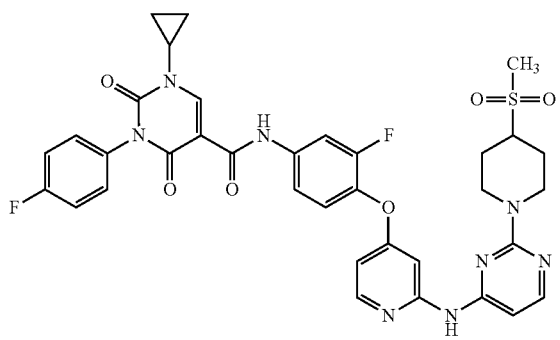 [SMILES: CS(=O)(=O)C1CCN(c2nccc(Nc3cc(Oc4ccc(NC(=O)c5cn(C6CC6)c(=O)n(-c6ccc(F)cc6)c5=O)cc4F)ccn3)n2)CC1]

Step 1: 1-cyclopropyl-N-(3-fluoro-4-((2-((2-(4-(methylsulfonyl)piperidin-1-yl)pyrimidin-4-yl)amino)pyridin-4-yl)oxy)phenyl)-3-(4-fluorophenyl)-2,4-dioxo-1,2,3,4-tetrahydropyrimidine-5-carboxamide To a 4 mL vial containing 1-cyclopropyl-3-(4-fluorophenyl)-2,4-dioxo-1,2,3,4-tetrahydropyrimidine-5-carboxylic acid (15 mg, 0.052 mmol), N-(4-(4-amino-2-fluorophenoxy)pyridin-2-yl)-2-(4-(methylsulfonyl)piperidin-1-yl)pyrimidin-4-amine (23.7 mg, 0.052 mmol, prepared according to the procedures used in Example 102) and Et₃N (8.6 uL, 0.062 mmol) in NMP (0.5 mL) was added HATU (23.6 mg, 0.062 mmol). The reaction was stirred at room temperature 18 hours then purified via preparative LC/MS with the following conditions; Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate: Gradient: 34-74% B over 20 minutes, then a 4-minute hold at 100% B; Flow: 20 mL/min. Fractions containing the desired product were combined and dried via centrifugal evaporation to give the title compound (17.2 mg, 45.5%). $^1$H NMR (500 MHz, DMSO-$d_6$) δ 10.89 (s, 1H), 8.49 (s, 1H), 8.17 (d, J=5.7 Hz, 1H), 8.01 (d, J=5.6 Hz, 1H), 7.92 (dd, J=12.9, 2.3 Hz, 1H), 7.46 (br d, J=8.2 Hz, 1H), 7.41-7.32 (m, 6H), 6.67 (dt, J=5.5, 2.7 Hz, 2H), 4.50 (br d, J=12.6 Hz, 2H), 2.87 (s, 3H), 2.74 (br t, J=11.7 Hz, 2H), 2.54 (s, 3H), 1.97 (br d, J=11.1 Hz, 2H), 1.44 (qd, J=12.3, 4.0 Hz, 2H), 1.08-1.00 (m, 4H); LCMS (M+H)+=731.2: HPLC RT=1.87 min. (Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.: Gradient: 0% B to 100% B over 3 min, then a 0.75 min hold at 100% B; Flow: 1 mL/min; Detection UV 220 nm)

Examples 113 to 114

The compounds in Table 10 were prepared according to the procedures described for Example 112.

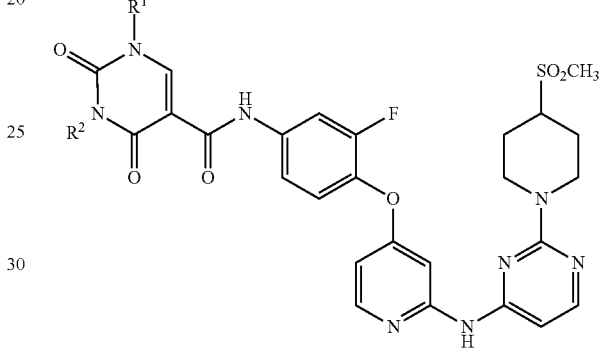

TABLE 10

| Ex. No. | R¹ | R² | HPLC RT (min) | LC/MS (M + H) | HPLC Method |
|---|---|---|---|---|---|
| 113 | H₃C⟋⟍CH₃ (isopropyl) | bicyclopentyl | 2.253 | 705.4 | A |
| 114 | H₃C⟋⟍CH₃ (isopropyl) | 4-fluorophenyl | 2.05 | 733.17 | B |

HPLC Conditions for Table 10:

Method A; Column: Waters BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.: Gradient: 0% B, 0-100% B over 3 minutes, then a 0.75-minute hold at 100% B; Flow: 1.0 mL/min; Detection; UV at 220 nm.

Method B; Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate;

Temperature: 50° C.; Gradient: 0% B to 100% B over 3 min, then a 0.75 min hold at 100% B; Flow: 1 mL/min; Detection: MS and UV (220 nm).

Example 115

N-{4-[(2-{[2-(4-methanesulfonylpiperidin-1-yl)pyrimidin-4-yl]amino}-5-methylpyridin-4-yl)oxy]phenyl}-2,4-dioxo-3-phenyl-1-(propan-2-yl)-1,2,3,4-tetrahydropyrimidine-5-carboxamide

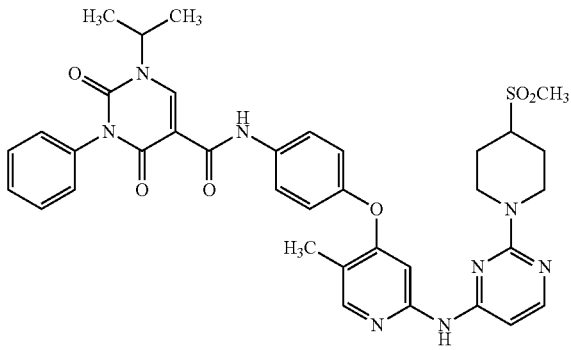 [SMILES: Cc1cnc(Nc2ccnc(N3CCC(S(C)(=O)=O)CC3)n2)cc1Oc1ccc(NC(=O)c2cn(C(C)C)c(=O)n(-c3ccccc3)c2=O)cc1]

Step 1.
2-chloro-5-methyl-4-(4-nitrophenoxy)pyridine

To a 40 mL vial containing 2-chloro-5-methylpyridin-4-ol (250 mg, 1.74 mmol) and 1-fluoro-4-nitrobenzene (246 mg, 1.74 mmol) in NMP (3 mL) was added $Cs_2CO_3$ (624 mg, 1.94 mmol). The reaction was heated on a heating block at 110° C. for 30 minutes then cooled to room temperature. The reaction was diluted with water and the resulting precipitate collected by filtration, rinsed with water then hexane and dried under vacuum to give the title compound (321.5 mg, 69.8%) as an off-white solid. $^1$H NMR (500 MHz, DMSO-$d_6$) δ 8.37 (d, J=0.6 Hz, 1H), 8.35-8.29 (m, 2H), 7.41-7.33 (m, 2H), 7.06 (s, 1H), 2.20 (s, 3H). LCMS (M+H)=265. HPLC RT=2.053 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2.
4-((2-chloro-5-methylpyridin-4-yl)oxy)aniline

To a 40 mL vial containing 2-chloro-5-methyl-4-(4-nitrophenoxy)pyridine (321 mg, 1.21 mmol), zinc powder (634 mg, 9.7 mmol) in EtOH (4 mL) was added ammonium chloride (519 mg, 9.7 mmol). The reaction was heated on a heating block at 80° C. for 1 hour then cooled to room temperature. The reaction was filtered through a 0.45 um membrane with EtOH rinses and then concentrated. The residue was diluted with water and basified with sat $NaHCO_3$ aq stirring at room temperature. The resulting precipitate was collected by filtration, rinsed with water and dried under vacuum to give the title compound (261.3 mg, 92%) as an off-white solid. LCMS (M+H)=235. HPLC RT=0.818 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: N-(4-((2-chloro-5-methylpyridin-4-yl)oxy)phenyl)-1-isopropyl-2,4-dioxo-3-phenyl-1,2,3,4-tetrahydropyrimidine-5-carboxamide To a 4 mL vial containing 1-isopropyl-2,4-dioxo-3-phenyl-1,2,3,4-tetrahydropyrimidine-5-carboxylic acid (24.6 mg, 0.09 mmol), 4-((2-chloro-5-methylpyridin-4-yl)oxy)aniline (21.05 mg, 0.09 mmol) and Et3N (15 uL, 0.108 mmol) in NMP (0.3 mL) was added HATU (40.9 mg, 0.108 mmol). The reaction was stirred at room temperature 4 hours and diluted with water and saturated $NaHCO_3$ aq. The white precipitate that formed was collected by filtration, rinsed with water and dried under vacuum to give the title compound (41.4 mg, 94%) as a white solid. LCMS (M+H)=491. HPLC RT=2.858 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: 1-isopropyl-N-(4-((5-methyl-2-((2-(4-(methylsulfonyl)piperidin-1-yl)pyrimidin-4-yl)amino)pyridin-4-yl)oxy)phenyl)-2,4-dioxo-3-phenyl-1,2,3,4-tetrahydropyrimidine-5-carboxamide To a 4 mL vial containing N-(4-((2-chloro-5-methylpyridin-4-yl)oxy)phenyl)-1-isopropyl-2,4-dioxo-3-phenyl-1,2,3,4-tetrahydropyrimidine-5-carboxamide (20 mg, 0.041 mmol), 2-(4-(methylsulfonyl)piperidin-1-yl)pyrimidin-4-amine (15.7 mg, 0.061 mmol), XANTPHOS (2.8 mg, 4.8 umol), tris(dibenzylideneacetone)dipalladium(0) (3.7 mg, 4.0 umol) and $Cs_2CO_3$ (39.8 mg, 0.122 mmol) in dioxane (0.5 mL). The reaction was heated on a 110° C. heating block for 2 hours and diluted with THF and filtered through a 0.45 um membrane. The reaction mixture was concentrated and the crude material was purified via preparative LC/MS with the following conditions; Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 18-58% B over 20 minutes, then a 4-minute hold at 100% B; Flow: 20 mL/min. Fractions containing the desired product were combined and dried via centrifugal evaporation to give the title compound (11.3 mg, 38.4%). $^1$H NMR (500 MHz, DMSO-$d_6$) δ 10.91 (s, 1H), 8.61 (s, 1H), 8.21 (s, 1H), 7.92 (s, 1H), 7.75 (d, J=8.9 Hz, 2H), 7.55-7.49 (m, 2H), 7.48-7.43 (m, 1H), 7.33 (br d, J=7.3 Hz, 2H), 7.23 (br s, 1H), 7.19 (br d, J=8.9 Hz, 2H), 4.77 (dt, J=13.6, 6.9 Hz, 1H), 4.11 (br d, J=11.9 Hz, 1H), 3.30-3.20 (m, 1H), 3.19-3.11 (m, 1H), 2.83 (br s, 3H), 2.72 (s, 3H), 2.24 (s, 3H), 1.97 (br d, J=10.7 Hz, 2H), 1.54-1.43 (m, 2H), 1.41 (d, J=6.7 Hz, 6H); LCMS (M+H)+=711.1; HPLC RT=1.99 min (Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection UV 220 nm)

Example 116

N-{4-[(2-{[5-cyano-6-(4-methanesulfonylpiperazin-1-yl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide

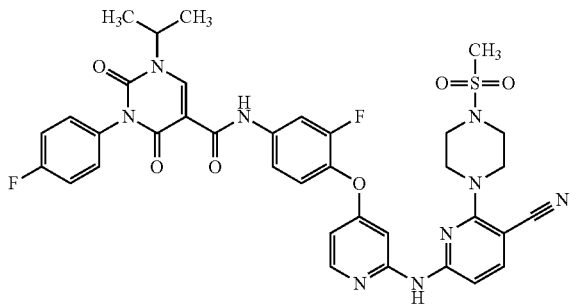 [SMILES: CC(C)n1cc(C(=O)Nc2ccc(Oc3ccnc(Nc4ccc(C#N)c(N5CCN(S(C)(=O)=O)CC5)n4)c3)c(F)c2)c(=O)n(-c2ccc(F)cc2)c1=O]

Step 1. 6-amino-2-chloronicotinonitrile 2,6-Dichloronicotinonitrile (10.00 g, 57.8 mmol) was dissolved into 2M NH$_3$-IPA (100 ml, 200 mmol) in a steel bomb behind a blast shield. The reaction vessel was sealed and heated to 90° C. for 20 hours. Cooled to room temperature and stirred for 48 h. The heterogeneous reaction mixture was partitioned between EtOAc and a small amount of half-saturated NaHCO$_3$. The aqueous phase was extracted with EtOAc (2×). The combined organics were washed with brine and dried over MgSO4 before concentrating onto 16 g of celite. Column chromatography (330 g SiO$_2$, 0 to 50% EtOAc-hexane) afforded 6-amino-2-chloronicotinonitrile as the major product (5.14 g, 58%) with the minor product, 2-amino-6-chloronicotinonitrile also isolated (1.60 g, 18%). 1H NMR (400 MHz, DMSO-d$_6$) δ 7.78 (d, J=8.6 Hz, 1H), 7.50 (s, 2H), 6.46 (d, J=8.6 Hz, 1H); LC/MS [M+H] 195.0; LC RT=1.082 min; (Column: Waters Xbridge; Mobile Phase A: 5:95 acetonitrile:water with 10 mM ammonium acetate; Mobile Phase B: 95:5 acetonitrile:water with 10 mM ammonium acetate; Temperature: 35° C.; Gradient: 5-95% B over in 4 min; Flow: 4.0 mL/min).

Step 2. 6-amino-2-(4-(methylsulfonyl)piperazin-1-yl)nicotinonitrile

6-Amino-2-chloronicotinonitrile (250 mg, 1.628 mmol), 1-(methylsulfonyl)piperazine, HCl (1307 mg, 6.51 mmol) and potassium carbonate (675 mg, 4.88 mmol) were suspended in DMA (5426 µl). The reaction mixture was heated to 105° C. overnight, cooled to rt and stirred for 72 h. The reaction was decanted into a separatory funnel containing EtOAc and H$_2$O, rinsing the residual K$_2$CO$_3$ with EtOAc. The aqueous layer was extracted with EtOAc (2×) and the combined organics were washed with 10% LiCl solution before drying (MgSO4) and concentrating to a cream solid to afford the titled product (461 mg, 85% purity, 86% yield). This material was used as is in the subsequent reactions. 1H NMR (400 MHz, DMSO-d$_6$) δ 7.52 (d, J=8.4 Hz, 1H), 6.83 (br s, 2H), 6.46 (d, J=8.7 Hz, 1H), 5.99 (d, J=8.4 Hz, 1H), 3.68-3.54 (m, 4H), 3.27-3.12 (m, 4H), 2.92 (s, 3H); LC/MS [M+H]=282.2; LC RT 0.63 min; (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 3. N-{4-[(2-{[5-cyano-6-(4-methanesulfonylpiperazin-1-yl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide N-(4-((2-chloropyridin-4-yl)oxy)-3-fluorophenyl)-3-(4-fluorophenyl)-1-isopropyl-2,4-dioxo-1,2,3,4-tetrahydropyrimidine-5-carboxamide (30 mg, 0.058 mmol), 6-amino-2-(4-(methylsulfonyl)piperazin-1-yl)nicotinonitrile (16.46 mg, 0.058 mmol), potassium carbonate (24.25 mg, 0.175 mmol) and BrettPhos Precatalyst G1 (4.67 mg, 5.85 µmol) were suspended in t-BuOH/DMA (6:1) (688 µl). The reaction mixture was degassed with a stream of N2 for 1 min, sealed and heated to 120° C. in the microwave reactor for 45 min. After cooling to room temperature, the reaction mixture was diluted with EtOAc, filtered through a PTFE cartridge and concentrated. The crude material was dissolved in DMF and purified by preparative LC/MS with the following conditions; Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate: Gradient: 40-80% B over 20 minutes, then a 4-minute hold at 100% B; Flow: 20 mL/min. Fractions containing the desired product were combined and dried via centrifugal evaporation to afford the titled product (13.5 mg, 31%). 1H NMR (500 MHz, DMSO-d$_6$) δ 10.97 (br s, 1H), 10.14 (br s, 1H), 8.62 (br s, 1H), 8.20 (d, J=5.7 Hz, 1H), 7.94 (br d, J=12.7 Hz, 1H), 7.82 (br d, J=8.4 Hz, 1H), 7.47-7.29 (m, 7H), 7.05 (br d, J=4.2 Hz, 1H), 6.70 (dd, J=5.6, 1.9 Hz, 1H), 4.86-4.66 (m, 1H), 3.14 (br s, 4H), 2.86 (s, 3H), 1.41 (br d, J=6.6 Hz, 6H); LC/MS [M+H]=757.99; HPLC RT=2.23 min; Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Examples 117 to 134

The compounds in Table 11 were prepared according to the procedures described for Example 116.

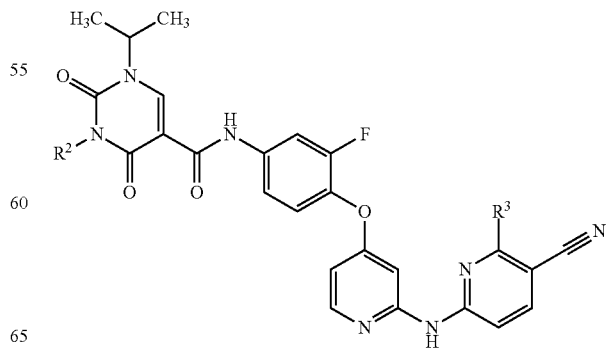

TABLE 11
| Ex. No. | R² | R³ | HPLC RT (min) | LC/MS (M + H) | HPLC Method |
|---|---|---|---|---|---|
| 117 | 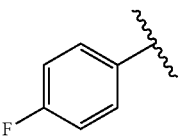 [SMILES: *c1ccc(F)cc1] | 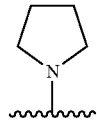 | 2.29 | 665.4 | A |
| 118 | 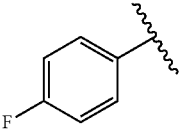 | 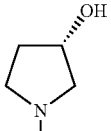 | 1.67 | 681.34 | B |
| 119 | 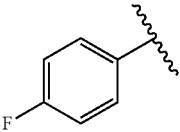 | 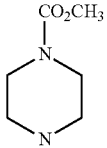 | 2.28 | 738.37 | A |
| 120 | 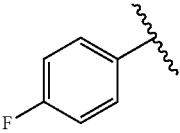 | 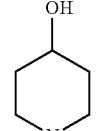 | 1.65 | 695.44 | B |
| 121 | 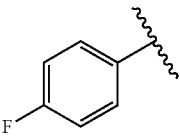 | 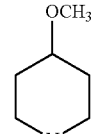 | 2.30 | 709.16 | A |
| 122 | 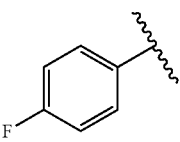 | 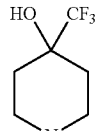 | 1.92 | 763.36 | B |
| 123 | 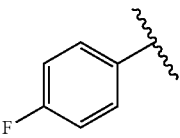 | 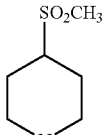 | 2.12 | 757.41 | A |
| 124 | 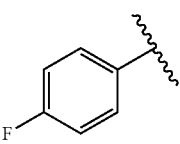 | 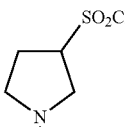 | 2.12 | 743.32 | A |

TABLE 11-continued

| Ex. No. | R² | R³ | HPLC RT (min) | LC/MS (M + H) | HPLC Method |
|---|---|---|---|---|---|
| 125 | 4-fluorophenyl-CH₂- | 1-SO₂CH₃, 3-CH₃ piperazine | 2.18 | 772.08 | A |
| 126 | 4-fluorophenyl-CH₂- | 3-OH pyrrolidine | 2.34 | 695.14 | A |
| 127 | 4-fluorophenyl-CH₂- | 4-SO₂CH₃ piperazine | 2.41 | 772.13 | A |
| 128 | 4-fluorophenyl-CH₂- | 4-CO₂CH₃ piperazine | 2.46 | 752.52 | A |
| 129 | phenyl-CH₂- | 4-SO₂CH₃ piperidine | 2.29 | 753.24 | A |
| 130 | phenyl-CH₂- | 4-CO₂CH₃ piperazine | 2.34 | 734.18 | A |
| 131 | phenyl-CH₂- | 4-SO₂CH₃ piperazine | 2.32 | 754.16 | A |
| 132 | phenyl-CH₂- | 4-OH, 4-CF₃ piperidine | 2.41 | 759.16 | A |

TABLE 11-continued

| Ex. No. | R² | R³ | HPLC RT (min) | LC/MS (M + H) | HPLC Method |
|---|---|---|---|---|---|
| 133 | 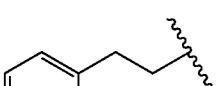 | 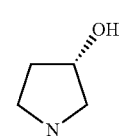 | 2.40 | 691.12 | A |
| 134 | 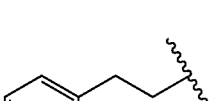 | 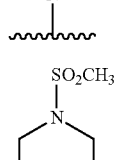 | 2.44 | 768.47 | A |

HPLC Conditions for Table 11:

Method A; Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate. Temperature; 50° C.: Gradient: 0% B to 100% B over 3 min, then a 0.75 min hold at 100% B; Flow: 1 mL/min; Detection: UV (220 nm).

Method B; Column: Waters XBridge C18, 2.1 mm×50 mm, 1.7 μm particles; Mobile Phase A: 5:95 acetonitrile:water with 0.1% trifluoroacetic acid, Mobile Phase B: 95:5 acetonitrile:water with 0.1% trifluoroacetic acid; Temperature: 50° C.: Gradient: 0% B to 100% B over 3 min, then a 0.75 min hold at 100% B; Flow: 1 mL/min; Detection: MS and UV (220 nm).

Example 135

N-{3-fluoro-4-[(2-{[3-fluoro-6-(4-methanesulfonylpiperazin-1-yl)pyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide

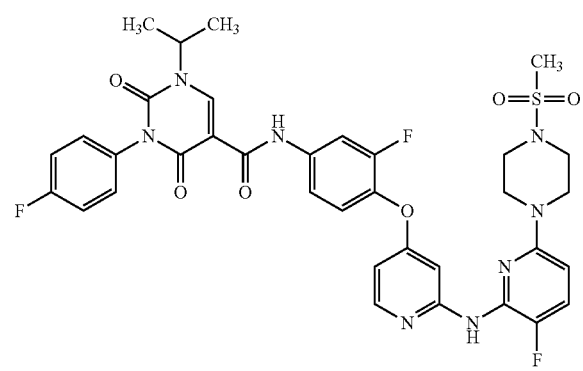 [SMILES: CC(C)n1cc(C(=O)Nc2ccc(Oc3ccnc(Nc4nc(N5CCN(S(C)(=O)=O)CC5)ccc4F)c3)c(F)c2)c(=O)n(-c2ccc(F)cc2)c1=O]

Step 1. 3-fluoro-6-(4-(methylsulfonyl)piperazin-1-yl)pyridin-2-amine 3,6-difluoropyridin-2-amine (100 mg, 0.769 mmol), 1-(methylsulfonyl)piperazine, HCl (463 mg, 2.306 mmol) were suspended in DMA (2562 μl) at rt. DIPEA (403 μl, 2.306 mmol) was added and the reaction vessel was sealed and heated to 200° C. for 4 h before cooling and standing at rt overnight. The reaction mixture was transferred to a microwave vial, sealed and heated to 200° C. for 3 h. After cooling to room temperature, the mixture was partitioned between EtOAc and H₂O. The aqueous phase was extracted into EtOAc (2×), and the combined organics were washed with 10% LiCl solution, dried over MgSO4 and concentrated. Column chromatography (12 g SiO₂, 30 to 100% EtOAc-hexane gradient elution) afforded the expected product as a cream solid (29 mg, 14%). 1H NMR (400 MHz, CHLOROFORM-d) δ 7.13 (dd, J=9.9, 8.7 Hz, 1H), 5.93 (dd, J=8.6, 1.8 Hz, 1H), 4.41 (br s, 2H), 3.62-3.49 (m, 4H), 3.37-3.27 (m, 4H), 2.82 (s, 3H); LC/MS [M+H]=275.1; LC RT 0.54 min (Column: Waters Acquity BEH C18 2.1×50 mm Mobile Phase A: Water with 0.05% TFA; Mobile Phase B: Acetonitrile with 0.05% TFA; Temperature: 40° C.; Gradient: 2-98% B over 1.5 min; Flow: 1 mL/min).

Step 2. N-{3-fluoro-4-[(2-{[3-fluoro-6-(4-methanesulfonylpiperazin-1-yl)pyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide N-(4-((2-chloropyridin-4-yl)oxy)-3-fluorophenyl)-3-(4-fluorophenyl)-1-isopropyl-2,4-dioxo-1,2,3,4-tetrahydropyrimidine-5-carboxamide (18.70 mg, 0.036 mmol), 3-fluoro-6-(4-(methylsulfonyl)piperazin-1-yl)pyridin-2-amine (10 mg, 0.036 mmol), potassium carbonate (15.11 mg, 0.109 mmol) and BrettPhos Precatalyst G1 (2.91 mg, 3.65 μmol) were suspended in t-BuOH/DMA (6:1) (429 μl). The reaction mixture was degassed with a stream of N₂, sealed and heated to 120° C. in the microwave reactor for 45 min. After cooling to rt, the reaction mixture was diluted with EtOAc, filtered through a PTFE frit and concentrated. The crude product was dissolved in DMF and purified via preparative LC/MS with the following conditions; Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 minutes, then a 4-minute hold at 100% B; Flow: 20 mL/min. Fractions containing the desired product were combined and dried via centrifugal evaporation to afford the titled compound (1.8 mg). 1H NMR (500 MHz, DMSO-d6) δ 10.97 (s, 1H), 8.80 (s, 1H), 8.63 (s, 1H), 8.13 (d, J=5.5 Hz, 1H), 7.94 (dd, J=12.8, 1.8 Hz, 1H), 7.55-7.26 (m, 8H), 6.63 (dd, J=5.6, 2.0 Hz, 1H), 6.35 (br d, J=7.6 Hz, 1H), 4.78 (dt, J=13.4, 6.7 Hz, 1H), 3.29 (br s, 2H), 3.08 (br s, 3H), 2.85 (s, 3H), 1.42 (br d, J=6.7 Hz, 6H); LC/MS [M+H]=751.22; LC RT=2.22 min; Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Example 136

N-{3-fluoro-4-[(2-{[6-(4-methanesulfonylpiperazin-1-yl)-4-methylpyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide

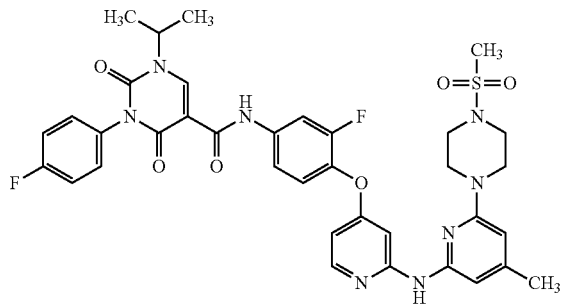 [SMILES: Cc1cc(Nc2cc(Oc3ccc(NC(=O)c4cn(C(C)C)c(=O)n(-c5ccc(F)cc5)c4=O)cc3F)ccn2)nc(N2CCN(S(C)(=O)=O)CC2)c1]

Step 1: tert-butyl (6-bromo-4-methylpyridin-2-yl)carbamate

A mixture of 6-bromo-4-methylpyridin-2-amine (500 mg, 2.67 mmol), BOC-anhydride (0.621 mL, 2.67 mmol) and Et₃N (0.410 mL, 2.94 mmol) in t-butanol (13 mL) was stirred at rt for 24 h. BOC-anhydride (0.621 mL, 2.67 mmol) was added and the mixture was stirred at rt for 24 h. The reaction was quenched with water (20 mL). The aqueous layer was extracted with EtOAc (3×). The organic layer was evaporated and the residue was purified by ISCO silica gel chromatography (24 g column, gradient from 0% to 40% EtOAc/Hexanes) to afford the title compound (582 mg, 76%). LCMS (M+H)=289.0. HPLC RT=0.99 min (Column: Waters Acquity BEH C18 2.1×50 mm; Mobile Phase A: Water with 0.05% TFA; Mobile Phase B: Acetonitrile with 0.05% TFA; Temperature: 40° C.; Gradient: 2-98% B over 1.5 min; Flow: 1 mL/min).

Step 2: tert-butyl (4-methyl-6-(4-(methylsulfonyl)piperazin-1-yl)pyridin-2-yl)carbamate A mixture of tert-butyl (6-bromo-4-methylpyridin-2-yl)carbamate (265 mg, 0.92 mmol), 1-(methylsulfonyl)piperazine (182 mg, 1.11 mmol), cesium carbonate (601 mg, 1.85 mmol) and XPhos Pd G2 (72.6 mg, 0.09 mmol) in Dioxane (5 mL) was heated to 80° C. for 2 h. The reaction mixture was cooled and then transferred to a separatory funnel using EtOAc. The organic layer was washed with water (3×) and brine (3×). The organic layer was separated, dried over sodium sulfate, concentrated and the residue was purified using ISCO silica gel chromatography (24 g column, gradient from 0% to 50% EtOAc/Hexanes) to afford the title compound (138 mg, 0.37 mmol, 40% yield). LCMS (M+H) =371.1. HPLC RT=0.75 min (Column: Waters Acquity BEH C18 2.1×50 mm; Mobile Phase A: Water with 0.05% TFA; Mobile Phase B: Acetonitrile with 0.05% TFA; Temperature: 40° C.; Gradient: 2-98% B over 1.5 min; Flow: 1 mL/min).

Step 3: 4-methyl-6-(4-(methylsulfonyl)piperazin-1-yl)pyridin-2-amine

A solution of tert-butyl (4-methyl-6-(4-(methylsulfonyl)piperazin-1-yl)pyridin-2-yl)carbamate (170 mg, 0.46 mmol) in hydrochloric acid (4M in Dioxane) (2.9 mL, 11.47 mmol) was stirred at rt for 14 h. The solvent was evaporated and the residue was suspended in 10 mL of hexanes. The precipitate formed was collected and dried to afford the title compound (582 mg, 76%) as a hydrochloride salt. LCMS (M+H) =271.2. HPLC RT=0.51 min (Column: Waters Acquity BEH C18 2.1×50 mm; Mobile Phase A: Water with 0.05% TFA; Mobile Phase B: Acetonitrile with 0.05% TFA; Temperature: 40° C.; Gradient: 2-98% B over 1.5 min; Flow: 1 mL/min).

Step 4: N-(3-fluoro-4-((2-((4-methyl-6-(4-(methylsulfonyl)piperazin-1-yl)pyridin-2-yl)amino)pyridin-4-yl)oxy)phenyl)-3-(4-fluorophenyl)-1-isopropyl-2,4-dioxo-1,2,3,4-tetrahydropyrimidine-5-carboxamide A mixture of N-(4-((2-chloropyridin-4-yl)oxy)-3-fluorophenyl)-3-(4-fluorophenyl)-1-isopropyl-2,4-dioxo-1,2,3,4-tetrahydropyrimidine-5-carboxamide (25 mg, 0.05 mmol), 4-methyl-6-(4-(methylsulfonyl)piperazin-1-yl)pyridin-2-amine (13.18 mg, 0.05 mmol), K₂CO₃ (26.9 mg, 0.2 mmol) and chloro[2-(dicyclohexylphosphino)-3,6-dimethoxy-2',4',6'-triisopropyl-1,1'-biphenyl][2-(2-aminoethyl)phenyl]palladium(II) (3.89 mg, 4.87 µmol) in t-Butanol/DMA 6/1 (975 µl) was degassed with N₂ gas and heated to 120° C. for 6 h. The reaction was mixture was diluted with DMF (2 mL), filtered and purified by preparative LC/MS (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 4-minute hold at 100% B; Flow: 20 mL/min.) to afford the title compound (7.9 mg, 10.58 µmol, 21.70% yield). LCMS (M+H)=747.2. ¹H NMR (500 MHz, DMSO-d₆) δ 10.92 (s, 1H), 9.15 (br s, 1H), 8.63 (s, 1H), 8.04-7.86 (m, 2H), 7.45-7.39 (m, 3H), 7.38-7.25 (m, 4H), 6.70-6.70 (m, 1H), 6.71 (s, 1H), 6.53 (br s, 1H), 6.17 (br s, 1H), 4.79 (dt, J=13.5, 6.8 Hz, 1H), 3.41 (br s, 2H), 3.11 (br s, 3H), 2.87-2.82 (m, 3H), 2.17 (s, 3H), 1.44 (d, J=6.8 Hz, 6H), 1.28-1.21 (m, 3H), 1.02 (d, J=6.3 Hz, 1H). HPLC RT=1.98 min (Column: Waters XBridge C18 2.1×50 mm; Mobile Phase A: 5:95 ACN:water with 0.1% TFA; Mobile Phase B: 95:5 ACN:water with 0.1% TFA; Temperature: 40° C.; Gradient: 0-100% B over 3 min; Flow: 1 mL/min).

Example 137

N-(3-fluoro-4-[(2-{[4-(4-methanesulfonylpiperazin-1-yl)-5-methylpyrimidin-2-yl]amino}pyridin-4-yl)oxy]phenyl)-3-(4-fluorophenyl)-2,4-dioxo-1-(propan-2-yl)-1,2,3,4-tetrahydropyrimidine-5-carboxamide

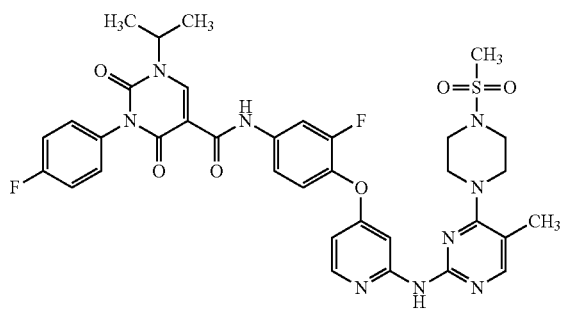 [SMILES: Cc1cnc(Nc2cc(Oc3ccc(NC(=O)c4cn(C(C)C)c(=O)n(-c5ccc(F)cc5)c4=O)cc3F)ccn2)nc1N1CCN(S(C)(=O)=O)CC1]

Step 1. 5-methyl-4-(4-(methylsulfonyl)piperazin-1-yl)pyrimidin-2-amine 4-chloro-5-methylpyrimidin-2-amine (100 mg, 0.697 mmol), 1-(methylsulfonyl)piperazine (458 mg, 2.79 mmol) and potassium carbonate (289 mg, 2.090 mmol) were suspended in DMA (2322 µl) and heated to 105° C. for 16 h. After cooling to rt, the reaction mixture was decanted into EtOAc and H$_2$O. The aqueous phase was extracted with EtOAc (2×). The combined organic layers were washed with 10% LiCl solution, dried over MgSO4 and concentrated to a amber oil which was dried under vacuum to afford the titled compound (134 mg, 71%). 1H NMR (400 MHz, DMSO-d6) δ 7.74 (s, 1H), 6.02 (s, 2H), 3.44-3.35 (m, 4H), 3.25-3.17 (m, 4H), 2.91 (s, 3H), 2.03 (s, 3H); LCMS [M+H] 272.1; LC RT 0.48 min (Column: BEH C18 2.1×50 mm; Mobile Phase A: water with 0.05% TFA; Mobile Phase B: acetonitrile with 0.05% TFA; Temperature: 50° C.; Gradient: 2-98% B over 1.7 min; Flow: 0.8 mL/min).

Step 2. N-{3-fluoro-4-[(2-([4-(4-methanesulfonylpiperazin-1-yl)-5-methylpyrimidin-2-yl]amino}pyridin-4-yl)oxy]phenyl)-3-(4-fluorophenyl)-2,4-dioxo-1-(propan-2-yl)-1,2,3,4-tetrahydropyrimidine-5-carboxamide N-(4-((2-chloropyridin-4-yl)oxy)-3-fluorophenyl)-3-(4-fluorophenyl)-1-isopropyl-2,4-dioxo-1,2,3,4-tetrahydropyrimidine-5-carboxamide (30 mg, 0.058 mmol), 5-methyl-4-(4-(methylsulfonyl)piperidin-1-yl)pyrimidin-2-amine (15.81 mg, 0.058 mmol), Xantphos (3.38 mg, 5.85 µmol) and Cs$_2$CO$_3$ (57.2 mg, 0.175 mmol) were suspended in Dioxane (585 µl) at rt. The reaction mixture was degassed with a stream of N$_2$ for 1 min before the addition of Pd$_2$(dba)$_3$ (5.36 mg, 5.85 µmol). The reaction was degassed for an additional 1 min, sealed the reaction vial and heated to 110° C. for 2 h before cooling to rt. The reaction mixture was diluted with EtOAc, filtered through a PTFE frit and concentrated. The crude material was redissolved in DMF and purified via preparative LC/MS with the following conditions; Column: XBridge C18, 200 mm×19 mm, 5-µm particles; Mobile Phase A: 5:95 acetonitrile:water with 0.10% trifluoroacetic acid; Mobile Phase B: 95:5 acetonitrile:water with 0.1% trifluoroacetic acid; Gradient: a 0-minute hold at 26% B, 26-66% B over 20 minutes, then a 10-minute hold at 100% B; Flow Rate: 20 mL/min; Column Temperature: 25 C. Fraction collection was triggered by MS and UV signals. Fractions containing the desired product were combined and dried via centrifugal evaporation to afford the titled product as its TFA salt (5.5 mg, 11%). 1H NMR (500 MHz, DMSO-d6) δ 11.07 (s, 1H), 8.68 (s, 1H), 8.31 (d, J=6.1 Hz, 1H), 8.04 (br d, J=12.8 Hz, 1H), 7.98 (s, 1H), 7.55 (br d. J=8.2 Hz, 1H), 7.48-7.32 (m, 4H), 6.93 (br d, J=6.1 Hz, 1H), 6.81 (br s, 1H), 4.86-4.73 (m, 1H), 3.85 (br s, 3H), 3.28 (br s, 2H), 2.93 (s, 3H), 2.28 (s, 3H), 1.44 (br d, J=6.7 Hz, 5H); LC/MS [M+H]=748.33; LC RT=2.04 min; Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Example 138

N-{3-fluoro-4-[(2-{[6-(4-methanesulfonylpiperazin-1-yl)-5-(trifluoromethyl)pyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide

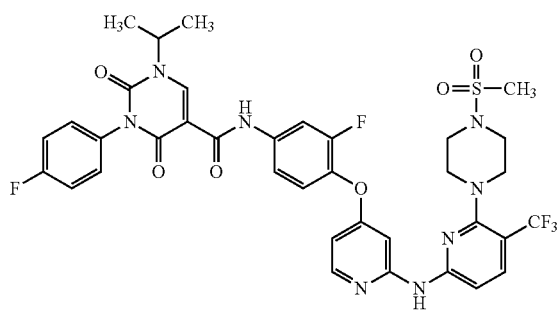 [SMILES: CC(C)n1cc(C(=O)Nc2ccc(Oc3ccnc(Nc4ccc(C(F)(F)F)c(N5CCN(S(C)(=O)=O)CC5)n4)c3)c(F)c2)c(=O)n(-c2ccc(F)cc2)c1=O]

Step 1: tert-Butyl (6-chloro-5-(trifluoromethyl)pyridin-2-yl)carbamate

To a 25 mL flask containing 6-chloro-5-(trifluoromethyl)pyridin-2-amine (ArkPharm, 273 mg, 1.39 mmol) and THF (2 mL) was added BOC$_2$O (Alfa-Aesar, 375 mg, 1.67 mmol). The reaction mixture was stirred for 48 hours. The reaction mixture was concentrated and the residue purified using ISCO silica gel chromatography (24 g column, gradient from 0% to 30% EtOAc/Hexanes) to give the title compound (204 mg, 49%) as a white solid. $^1$H NMR (400 MHz, CHLOROFORM-d) d 8.00-7.92 (m, 2H), 7.37 (br s, 1H), 1.54 (s, 9H). LCMS ([M-56]+H)=241.1.

Step 2: tert-Butyl (6-(4-(methylsulfonyl)piperazin-1-yl)-5-(trifluoromethyl)pyridin-2-yl)carbamate To a 4 mL vial containing tert-butyl (6-chloro-5-(trifluoromethyl)pyridin-2-yl)carbamate (29 mg, 0.099 mmol), 1-(methylsulfonyl)piperazine (Combi-Blocks, 19 mg, 0.12 mmol), Cs$_2$CO$_3$ (97 mg, 0.30 mmol) and 2$^{nd}$ Generation RuPhos precatalyst (3.9 mg, 5.0 µmol) was added degassed dioxane (991 μl). The reaction mixture was heated at 80° C. for 3 hours. Reaction mixture was concentrated in vacuo, the residue was dissolved in EtOAc and washed with H₂O. The EtOAc layer was concentrated to dryness. The resulting residue was purified using ISCO silica gel chromatography (12 g column, gradient from 0% to 30% EtOAc/Hexanes) to give the title compound (39 mg, 92%) as an off white solid ¹H NMR (400 MHz, CHLOROFORM-d) δ 7.85 (d, J=8.6 Hz, 1H), 7.66 (d, J=8.6 Hz, 1H), 7.16 (s, 1H), 3.37-3.33 (m, 4H), 3.32-3.28 (m, 4H), 2.83 (s, 3H), 1.54 (s, 9H). LCMS (M+H)=425.3.

Step 3. 6-(4-(Methylsulfonyl)piperazin-1-yl)-5-(trifluoromethyl)pyridin-2-amine

To 10 mL flask containing tert-butyl (6-(4-(methylsulfonyl)piperazin-1-yl)-5-(trifluoromethyl)pyridin-2-yl)carbamate (42 mg, 0.099 mmol) and DCM (827 μl) was added 37% aq HCl (500 μL, 6 mmol) and stirred for 30 minutes. The reaction mixture was neutralized by addition to a saturated solution of NaHCO₃, the resulting mixture was washed with EtOAc (3×). The combined organic layers were dried over Na₂SO₄ and concentrated giving the title compound (27 mg, 88%) as an off white solid. ¹H NMR (400 MHz, CHLOROFORM-d) δ 7.63-7.56 (m, 1H), 6.14 (d, J=8.4 Hz, 1H), 4.58 (br s, 2H), 3.73 (s, 3H), 3.58 (br s, 4H), 3.24-3.13 (m, 4H). LCMS (M+H)=325.3.

Step 4. N-(3-fluoro-4-((2-(((6-(4-(methylsulfonyl) piperazin-1-yl)-5-(trifluoromethyl)pyridin-2-yl) amino)pyridin-4-yl)oxy)phenyl)-3-(4-fluorophenyl)-1-isopropyl-2,4-dioxo-1,2,3,4-tetrahydropyrimidine-5-carboxamide To a 1 dram vial was added N-(4-((2-chloropyridin-4-yl) oxy)-3-fluorophenyl)-3-(4-fluorophenyl)-1-isopropyl-2,4-dioxo-1,2,3,4-tetrahydropyrimidine-5-carboxamide (26.3 mg, 0.051 mmol), 6-(4-(methylsulfonyl)piperazin-1-yl)-5-(trifluoromethyl)pyridin-2-amine (24.95 mg, 0.077 mmol), Xantphos (3.56 mg, 6.15 μmol), Cs₂CO₃ (50.1 mg, 0.154 mmol), Pd₂(dba)₃ (4.70 mg, 5.13 μmol) and Dioxane (513 μl). The reaction mixture was heated for 3 hours at 100° C. After cooling to rt, reaction mixture concentrated in vacuo giving a brown residue was dissolved in DMF, filtered and purified by preparative LC/MS (Column: Xbridge C18, 19×200 mm, 5 μM; Mobile Phase A: 5:95 acetonitrile:water with 0.1% TFA; Mobile Phase B: 95:5 acetonitrile:water with 0.1% TFA; Gradient: 30-70% B over 20 minutes, then a 4-minute hold at 100% B; Flow: 20 mL/min) to give the product (19 mg, 45%) upon centrifugal evaporation. ¹H NMR (500 MHz, DMSO-d₆) δ 10.95 (s, 1H), 8.61 (s, 1H), 8.22 (d, J=5.8 Hz, 1H), 7.93 (dd, J=12.8, 1.8 Hz, 1H), 7.87 (d, J=8.5 Hz, 1H), 7.50-7.31 (m, 6H), 7.29 (br s, 1H), 7.21 (br d, J=8.5 Hz, 1H), 6.70 (dd, J=5.8, 2.1 Hz, 1H), 4.75 (quin, J=6.7 Hz, 1H), 3.60-3.51 (m, 1H), 3.18-3.11 (m, 4H), 3.09 (br d, J=4.3 Hz, 4H), 2.86 (s, 3H), 1.41 (s, 3H), 1.39 (s, 3H). LCMS (M+H)=801.5. HPLC RT=1.88 min (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.: Gradient: 0% B to 100% B over 3 min, then a 0.75 min hold at 100% B; Flow: 1 mL/min; Detection: MS and UV (220 nm).

Examples 139- to 141

The compounds in Table 12 were prepared according to the procedures described for Example 138.

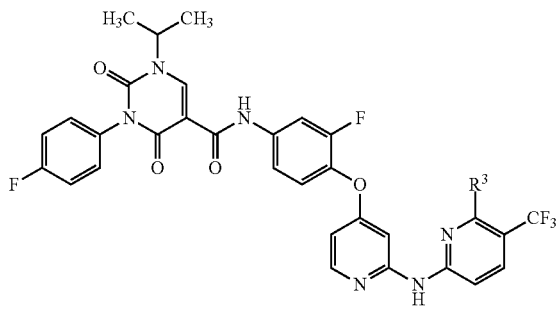

TABLE 12

| Ex. No. | R³ | HPLC RT (min) | LC/MS (M + H) | HPLC Method |
|---|---|---|---|---|
| 139 | CO₂Me (piperazine) | 1.94 | 781.5 | A |
| 140 | SO₂Me (piperidine) | 1.95 | 800.1 | A |
| 141 | SO₂N(CH₃)₂ (piperazine) | 2.05 | 830.5 | A |

HPLC Conditions for Table 12:
Method A; Column: Waters XBridge C18, 2.1 mm×50 mm, 1.7 μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B: Flow: 1 mL/min; Detection: MS and UV (220 nm).

Biological Assays

MERTK, AXL, TYRO3 Kinase Homogeneous Time Resolved Fluorescence (HTRF) Assay

Binding assays contained 1 nM kinase (GST-MERTK 578-872, HIS-AXL 473-End, or GST-TYRO 451-890), 0.2 nM terbium labelled antibody (anti-GST or anti-HIS), fluorescein-labeled kinase tracer at its respective kinase Kd, and test compounds in assay buffer consisting of 20 mM Hepes pH 7.5, 10 mM MgCl₂, 0.015% Brij-35, 2 mM DTT, and 50 μg/ml BSA. Assays were performed in black, flat-bottom, 1536-well plates. The reactions were incubated at room temperature for 60 minutes, following which the HTRF signals, ratio of fluorescence intensities at emission wavelengths for fluorescein acceptor (520 nm) and terbium donor (495 nm), the 520/495 ratio, were measured on the Envision Plate reader. Inhibition data were calculated from the 520/495 ratio generated by the no protein control reactions for 100% inhibition and vehicle-only reactions for 0% inhibition, and dose response curves generated to determine the concentration required for inhibiting 50% of the HTRF signal ($IC_{50}$). Compounds were dissolved at 10 mM in dimethylsulfoxide (DMSO) and evaluated at eleven concentrations.

MERTK/AXL/TYRO Caliper Activity Assays

The inhibitory activity of compounds was tested in the MERTK, AXL, and TYRO3 activity assays carried out in 20 mM Hepes pH 7.5, 10 mM $MgCl_2$, 0.05 mg/ml BSA, 0.015% Brij-15 and 2 mM DTT. Incubation mixtures containing 1 nM full length kinase (MERTK Life Technologies Part #PV4112, or AXL Life Technologies Part #A31521, or TYRO3 Life Technologies Part #A31521), ATP at the kinase ATP Km (30.100 and 15 mM for MerTK, Axl and Tyro3 respectively), 1.5 mM peptide substrate ([FITC]-AHA-KKKKEEIYFFFG-[OH]), and test compounds were incubated for 60 min, after which they were quenched with a 1 mM EDTA solution. The reaction mixtures were analyzed on a Caliper LabChip 3000 (Caliper LifeSciences, Hopinkton, MA, USA) by electrophoretic separation of the fluorescent substrate and phosphorylated product using the following run conditions: pressure of −1.2 psi, downstream voltage of −500 V, and upstream voltage of −1800 V. Inhibition data were calculated from the product conversion generated by the no enzyme control reactions for 100% inhibition and vehicle-only reactions for 0% inhibition. Dose response curves were generated to determine the concentration required for inhibiting 50% of the enzyme activity. Compounds were dissolved at 10 mM in dimethylsulfoxide (DMSO) and evaluated at eleven concentrations.

Inhibition of Efferocytosis Activity Assay

Human monocyes were commercially available (Biospecialty) and differentiated into MO Macrophages in differentiation media (RPMI, 10% FBS, 100 ng/ml M-CSF, Pen/Strep) in a flask for 6 days at 37° C. The cells were washed thoroughly with PBS (without Ca/Mg), Harvested with TrypLE and frozen down in aliquots.

One day before assay, thaw MO macrophage cells and plate at 10,000 cells per well in a black, clear-bottom 384-well plate in 40 ul of M2 polarization media (RPMI, 10% FBS, 100 ng/ml M-CSF, 100 nM Dexamethasone, Pen/Strep). Separately, treat Jurkat cells with 2 uM camptothecin in growth media (RPMI, 10% FBS. Pen/Strep) to induce apoptosis. Leave some Jurkat cells untreated. Incubate the macrophages and the Jurkats overnight at 37° C.

On the assay day, spin the Jurkat cells (apoptotic and untreated "live" jurkats, separately) at 1500 rpm for 5 min, wash once with PBS, and resuspend at $1\times10^6$ cells/ml in PBS containing 0.1 ug/ml pHrodo-SE (Life Technologies #P36600). Incubate the Jurkats for 30 min at RT in the dark. Then spin and wash the Jurkats twice with PBS, then resuspend them at $4\times10^6$ cells/ml in RPMI. Replace the macrophage cell media with 20 ul RPMI. Echo compounds 20 nl to macrophage plate and incubate for 30 min. Add 20 ul of labeled Jurkats to each well containing the M2 macrophages. Echo compounds additional 20 nl to macrophage plate. Spin briefly (~1 min) at 1000 rpm to settle Jurkats onto the bottom of the wells. Incubate at 37° C. for 1 hr. Wash the wells with 100 μl FACS buffer (PBS with Ca/Mg, 2% serum) twice, Stain with 20 μl of anti-CD11b-FITC (Biolegend #101206) at 1:500 dilution in FACS buffer. Incubate for 20 min at RT. Discard supernatant, wash the cells with FACS buffer once, then fill each well with 50 μl FACS Buffer.

Assess efferocytosis by High-Content Imaging using Celigo by gating CD11b labeled cells on the green channel and measuring the integrated intensity of pHrodo-SE on the red channel. In analysis, the base line is the signal from pHrodo-SE labeled live jurkats with M2 macrophages treated with DMSO and the total signal is from pHrodo-SE labeled apoptotic jurkats with M2 macrophages treated with DMSO.

MerTK/Axl pERK Target Engagement Assay

CHO-MerTK KD and CHO-Axl KD cells were plated at 3,000 cells/well in black 384-well plates (PDL treated, BD cat #356662) in 20 μl of Ham's F-12K (Kaighn's) Medium (Gibco, cat #21127022), in the presence of 10% FBS and Pen-Strep and cultured at 37° C. in 5% $CO_2$. In 18 hours, cells were washed once with serum-free F12K medium, and starved in the same medium for four hours.

Compounds were added at 25 nl to each well, and incubated with cells at 37° C. in 5% $CO_2$ for one hour. Human EGF was added to the wells at 100 ng/ml final concentration in 5 μL F12K medium. Plates were incubated at 37° C. with 5% $CO_2$ for 5 additional minutes.

Reaction was stopped by adding 25 μL/well of 8% formaldehyde and cells were fixed following the incubation for 30 min at RT using final concentration of 4% formaldehyde in DPBS containing $Ca^{2+}$ and $Mg^{2+}$ ($DPBS^{+/+}$). Fixed cells were washed twice with $DPBS^{+/+}$, followed by a 20 min permeabilization step using Permeabilization Buffer (ThermoFisher, cat #8408400)

Permeabilized cells were washed twice with $DPBS^{+/+}$ and blocked for 1 hour with 1× Blocking Buffer (ThermoFisher, cat #8408500). Anti-Phospho-p44/42 MAPK (Erk1/2) (Thr202/Tyr204) (D13.14.4E) XP® Rabbit primary antibody (CST, cat #4370) at 1:500 dilution in 1× Blocking Buffer were added to the cells and plates were incubated overnight at 4° C.

Plates were washed twice with $DPBS^{+/+}$. Alexa488 conjugated anti-rabbit secondary antibody (Invitrogen, cat #A11034) was added to the cells at 1:1000 dilution in 1× Blocking Buffer and incubated for 1 hour at RT. Hoechst33342 (Life Technology, cat #62249) was used for nuclear counter staining at 4 μg/mL final concentration in the same solution with the secondary antibody. Cells were washed twice with $DPBS^{+/+}$ after each antibody incubation step. Fluorescent images were acquired on CellInsight™ high-content platform (Thermofisher) using a 10× objective.

High-content images were analyzed using HCS Studio Cell Analysis Software (ThermoFisher). The average intensity of pERK staining was measured and used for compound's $IC_{50}$ calculation.

Compound $IC_{50}$ calculation: Average intensity of pERK reading per well in 100 ng/ml EGF/DMSO was set as 0%, and average intensity of pERK in no EGF/DMSO was set as 100%.

| Example# | Mer HTRF $IC_{50}$ (nM) | Axl HTRF $IC_{50}$ (nM) |
| --- | --- | --- |
| 1 | 14 | 2.9 |
| 3 | 59 | 1730 |
| 4 | 32 | 4.4 |
| 5 | 56 | 24 |
| 6 | 37 | 7.9 |
| 7 | 82 | 21 |
| 8 | 105 | 66 |
| 9 | 16 | 29 |
| 10 | 43 | 15 |
| 11 | 128 | 53 |
| 12 | 228 | 55 |
| 13 | 10 | 4.1 |

| Example# | Mer HTRF IC$_{50}$ (nM) | Axl HTRF IC$_{50}$ (nM) |
| --- | --- | --- |
| 14 | 11 | 3.6 |
| 15 | 8.0 | 1.7 |
| 16 | 5.8 | 1.1 |
| 17 | 1.9 | 2.7 |
| 18 | 18 | 11 |
| 19 | 4.4 | 1.6 |
| 20 | 12 | 4.7 |
| 21 | 164 | 39 |
| 22 | 49 | 8.9 |
| 23 | 55 | 31 |
| 24 | 12 | 5.6 |
| 25 | 13 | 3.6 |
| 26 | 60 | 18 |
| 27 | 19 | 6.8 |
| 28 | 20 | 7.4 |
| 29 | 182 | 7.2 |
| 30 | 165 | 48 |
| 31 | 158 | 7.5 |
| 32 | 342 | 0.9 |
| 33 | 67 | 19 |
| 35 | 4.3 | 0.8 |
| 36 | 38 | 11 |
| 37 | 14 | 2.6 |
| 38 | 16 | 3.5 |
| 39 | 11 | |
| 40 | 11 | 3.8 |
| 42 | 21 | 7.4 |
| 43 | 21 | 222 |
| 44 | 71 | 19 |
| 45 | 40 | 21 |
| 46 | 12 | 5.4 |
| 47 | 7.9 | 6.0 |
| 48 | 15 | 4.4 |
| 49 | 3,310 | 110 |
| 51 | 175 | 140 |
| 52 | 216 | 62 |
| 53 | 487 | 256 |
| 54 | 89 | |
| 55 | 6.7 | |
| 56 | 17 | |
| 58 | 201 | 287 |
| 59 | 137 | 12 |
| 60 | 114 | 995 |
| 61 | 794 | 4,174 |
| 62 | 23 | 4.6 |
| 63 | 119 | 62 |
| 64 | 814 | 181 |
| 65 | 127 | 100 |
| 66 | 29 | 31 |
| 67 | 71 | 87 |
| 68 | 20 | 7.1 |
| 69 | 23 | 18 |
| 70 | 14 | 14 |
| 71 | 40 | 12 |
| 72 | 119 | 90 |
| 73 | 24 | 59 |
| 74 | 1,444 | 2.9 |
| 75 | 42 | 3.5 |
| 76 | 38 | 18 |
| 77 | 8.3 | 5.0 |
| 78 | 9.8 | 986 |
| 79 | 13 | 70 |
| 80 | 19 | 12 |
| 81 | 17 | 4.4 |
| 82 | 8.8 | 256 |
| 83 | 13 | 3.4 |
| 84 | 31 | 2,329 |
| 85 | 19 | 3.9 |
| 86 | 31 | 10 |
| 87 | 6.7 | 16 |
| 88 | 5.6 | 3.3 |
| 89 | 6.6 | 4.4 |
| 90 | 3.1 | 2.2 |
| 91 | 72 | 38 |
| 92 | 1.9 | 0.4 |
| 93 | 1.6 | 0.4 |
| 94 | 3.5 | |
| 95 | 4.3 | 0.8 |
| 96 | 2.9 | 0.7 |
| 97 | 1.0 | 0.3 |
| 98 | 22 | 36 |
| 99 | 6.4 | 7.4 |
| 100 | 2.1 | 3.1 |
| 101 | 1.6 | 1.9 |
| 102 | 0.5 | 0.9 |
| 103 | 0.6 | 0.7 |
| 104 | 3.9 | 3.1 |
| 105 | 1.4 | 2.3 |
| 106 | 8.2 | 8.2 |
| 107 | 5.4 | 11 |
| 108 | 9.1 | 3.8 |
| 109 | 70 | 62 |
| 110 | 1.6 | |
| 111 | 14 | |
| 112 | 4.1 | 0.8 |
| 113 | 2.8 | 4.8 |
| 114 | 1.4 | 0.6 |
| 115 | 810 | 41 |
| 116 | 1.0 | 1.5 |
| 117 | 2.8 | 3.0 |
| 118 | 1.5 | 1.4 |
| 119 | 1.5 | 4.2 |
| 120 | 1.6 | 1.1 |
| 121 | 2.4 | 3.9 |
| 122 | 6.0 | 9.8 |
| 123 | 1.8 | 1.4 |
| 124 | 2.9 | 2.0 |
| 125 | 2.2 | 1.3 |
| 127 | 8.6 | 5.2 |
| 129 | 2.9 | |
| 130 | 7.1 | |
| 131 | 21 | 25 |
| 132 | 12 | |
| 133 | 22 | 52 |
| 135 | 1.0 | 1.1 |
| 136 | 3.9 | 1040 |
| 137 | 3.6 | 3.4 |
| 138 | 20 | 23 |
| 139 | 11 | 77 |
| 141 | 17 | 14,660 |

We claim:
1. A compound of the formula

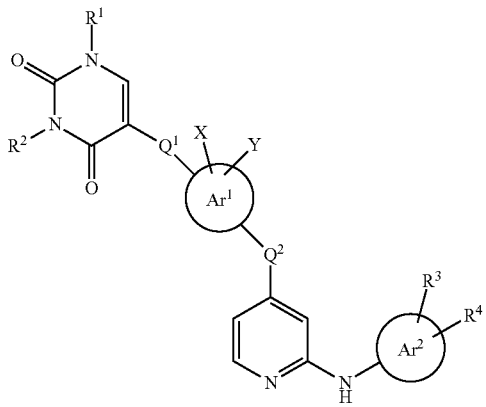

(I)

wherein:
Ar$^1$ is C$_3$-C$_8$ aryl or C$_3$-C$_8$ heteroaryl containing 1-4 heteroatoms selected from —N—, —O— or —S—;
Ar$^2$ is C$_3$-C$_8$ heteroaryl containing 1-4 heteroatoms selected from —N—, —O— or —S;
Q$^1$ is —NHCO—, —CONH—, —NHSO$_2$—, —SO$_2$NH—, —NHSO$_2$NH—, —NHCONH— or —OCONH—;
Q$^2$ is —O— or —NH—;
R$^1$ and R$^2$ are independently hydrogen, C$_1$-C$_6$ alkyl, —(CH$_2$)$_r$ C$_3$-C$_8$ cycloalkyl, —(CH$_2$)$_r$ C$_3$-C$_8$ aryl or —(CH$_2$)$_r$ C$_3$-C$_8$ heteroaryl containing 1-4 heteroatoms selected from —N—, —O— or —S—, said alkyl, cycloalkyl, aryl and heteroaryl groups substituted with 0-4 R$^{1a}$ groups;
R$^{1a}$ is hydrogen, halogen, CF$_3$, C$_1$-C$_3$ alkyl, C$_1$-C$_3$ alkoxy or —COC$_1$-C$_3$ alkyl;
R$^3$ and R$^4$ are independently hydrogen, halogen, CF$_3$, CN, C$_1$-C$_6$ alkyl, C$_1$-C$_6$ alkoxy, C$_3$-C$_8$ heterocyclyl containing 1-4 heteroatoms selected from —N—, —O— or —S—, —CONR$^5$R$^6$, —NR$^5$COR$^6$, —NR$^5$SO$_2$R$^6$, —SO$_2$R$^5$, —SO$_2$NR$^5$R$^6$, —NR$^5$R$^6$ or —NCOOR$^5$, said alkyl, heterocyclyl and alkoxy groups substituted with 0-4 R$^{3a}$ groups;
R$^{3a}$ is hydrogen, halogen, CHF$_2$, CF$_3$, C$_1$-C$_6$ alkyl, C$_1$-C$_3$ alkoxy, —(CH$_2$)$_r$COOR$^5$, OR$^5$, —SO$_2$R$^5$, —SO$_2$NR$^5$R$^6$, —NR$^5$R$^6$, NR$^5$COOR$^6$ or —COC$_1$-C$_3$ alkyl;

R$^5$ and R$^6$ are independently hydrogen, C$_1$-C$_6$ alkyl or C$_3$-C$_8$ aryl, said aryl and alkyl groups substituted with 0-4 R$^{5a}$; or R$^5$ and R$^6$ together with the nitrogen atoms to which they are attached form a heterocyclic ring containing 0-2 additional heteroatoms selected from —N—, —O— or —S— and are substituted with 0-2 R$^{5a}$ groups;
R$^{5a}$ is hydrogen, halogen, OH or C$_1$-C$_3$ alkyl;
X and Y are independently are independently hydrogen, halogen, C$_1$-C$_6$ alkyl, C$_1$-C$_6$ alkoxy, CN, —CONR$^5$R$^6$, —NR$^5$COR$^6$, —NR$^5$SO$_2$R$^6$, —SO$_2$R$^5$, —SO$_2$NR$^5$R$^6$, —NR$^5$R$^6$ or —NCOOR$^5$, said alkyl and alkoxy groups substituted with 0-4 R$^{3a}$ groups;
r is 0, 1 or 2;
or a pharmaceutically acceptable salt, tautomer or stereoisomer thereof.

2. The compound according to claim 1 of formula (I)

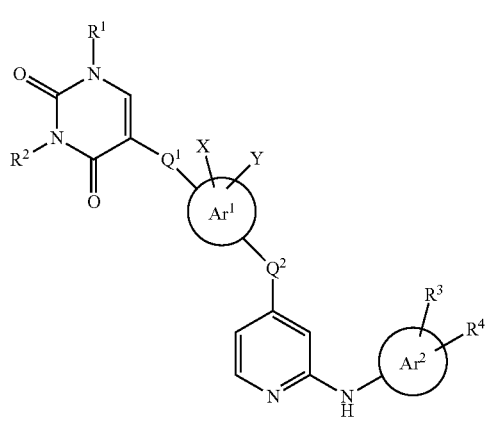

(I)

wherein:
Ar$^1$ is C$_3$-C$_8$ aryl
Ar$^2$ is C$_3$-C$_8$ heteroaryl containing 1-4 heteroatoms selected from —N—, —O— or —S;
Q$^1$ is —NHCO—, —CONH—, —NHSO$_2$—, —SO$_2$NH—, —NHSO$_2$NH—, —NHCONH— or —OCONH—;
Q$^2$ is —O— or —NH—;
R$^1$ and R$^2$ are independently hydrogen, C$_1$-C$_6$ alkyl, —(CH$_2$)$_r$ C$_3$-C$_8$ cycloalkyl, —(CH$_2$)$_r$ C$_3$-C$_8$ aryl or —(CH$_2$)$_r$ C$_3$-C$_8$ heteroaryl containing 1-4 heteroatoms selected from —N—, —O— or —S—, said alkyl, cycloalkyl, aryl and heteroaryl groups substituted with 0-4 $R^{1a}$ groups;

$R^{1a}$ is hydrogen, halogen, $CF_3$, $C_1$-$C_3$ alkyl, $C_1$-$C_3$ alkoxy or —$COC_1$-$C_3$ alkyl;

$R^3$ and $R^4$ are independently hydrogen, halogen, $CF_3$, CN, $C_1$-$C_6$ alkyl, $C_1$-$C_6$ alkoxy, $C_3$-$C_8$ heterocyclyl containing 1-4 heteroatoms selected from —N—, —O— or —S—, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl, heterocyclyl and alkoxy groups substituted with 0-4 $R^{3a}$ groups;

$R^{3a}$ is hydrogen, halogen, $CHF_2$, $CF_3$, $C_1$-$C_6$ alkyl, $C_1$-$C_3$ alkoxy, —$(CH_2)_rCOOR^5$, $OR^5$, —$SO_2R^5$, —$SO_2NR^5R^6$, —$NR^5R^6$, $NR^5COOR^6$ or —$COC_1$-$C_3$ alkyl;

$R^5$ and $R^6$ are independently hydrogen, $C_1$-$C_6$ alkyl or $C_3$-$C_8$ aryl, said aryl and alkyl groups substituted with 0-4 $R^{5a}$; or $R^5$ and $R^6$ together with the nitrogen atoms to which they are attached form a heterocyclic ring containing 0-2 additional heteroatoms selected from —N—, —O— or —S— and are substituted with 0-2 $R^{5a}$ groups;

$R^{5a}$ is hydrogen, halogen, OH or $C_1$-$C_3$ alkyl;

X and Y are independently are independently hydrogen, halogen, $C_1$-$C_6$ alkyl, $C_1$-$C_6$ alkoxy, CN, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl and alkoxy groups substituted with 0-4 $R^{3a}$ groups;

r is 0, 1 or 2;

or a pharmaceutically acceptable salt, tautomer or stereoisomer thereof.

3. The compound according to claim 2 of formula I

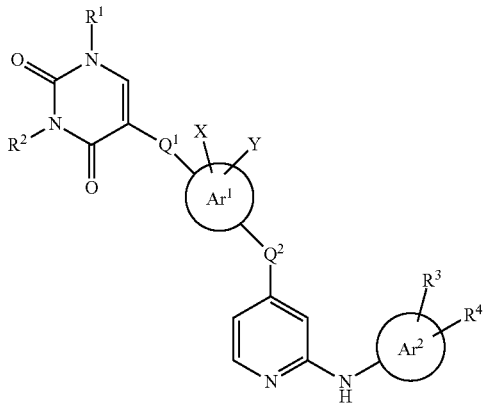

wherein:

$Ar^1$ is $C_3$-$C_8$ aryl $Ar^2$ is $C_3$-$C_8$ heteroaryl containing 1-4 heteroatoms selected from —N—, —O— or —S;

$Q^1$ is —NHCO— or —CONH;

$Q^2$ is —O— or —NH—;

$R^1$ and $R^2$ are independently hydrogen, $C_1$-$C_6$ alkyl, —$(CH_2)_r$ $C_3$-$C_8$ cycloalkyl, —$(CH_2)_r$ $C_3$-$C_8$ aryl or —$(CH_2)_r$ $C_3$-$C_8$ heteroaryl containing 1-4 heteroatoms selected from —N—, —O— or —S—, said alkyl, cycloalkyl, aryl and heteroaryl groups substituted with 0-4 $R^{1a}$ groups;

$R^{1a}$ is hydrogen, halogen, $CF_3$, $C_1$-$C_3$ alkyl, $C_1$-$C_3$ alkoxy or —$COC_1$-$C_3$ alkyl;

$R^3$ and $R^4$ are independently hydrogen, halogen, $CF_3$, CN, $C_1$-$C_6$ alkyl, $C_1$-$C_6$ alkoxy, $C_3$-$C_8$ heterocyclyl containing 1-4 heteroatoms selected from —N—, —O— or —S—, —$CONR^5R^6$, —$NR^5COR^6$, —$NR^5SO_2R^6$, —$SO_2R^5$, —$SO_2NR'R^6$, —$NR^5R^6$ or —$NCOOR^5$, said alkyl, heterocyclyl and alkoxy groups substituted with 0-4 $R^{3a}$ groups;

$R^{3a}$ is hydrogen, halogen, $CHF_2$, $CF_3$, $C_1$-$C_6$ alkyl, $C_1$-$C_3$ alkoxy, —$(CH_2)_rCOOR^5$, $OR^5$, —$SO_2R^5$, —$SO_2NR^5R^6$, —$NR^5R^6$, $NR^5COOR^6$ or —$COC_1$-$C_3$ alkyl;

$R^5$ and $R^6$ are independently hydrogen, $C_1$-$C_6$ alkyl or $C_3$-$C_8$ aryl, said aryl and alkyl groups substituted with 0-4 $R^{5a}$; or $R^5$ and $R^6$ together with the nitrogen atoms to which they are attached form a heterocyclic ring containing 0-2 additional heteroatoms selected from —N—, —O— or —S— and are substituted with 0-2 $R^{5a}$ groups;

$R^{5a}$ is hydrogen, halogen, OH or $C_1$-$C_3$ alkyl;

X and Y are independently are independently hydrogen, halogen, $C_1$-$C_6$ alkyl, $C_1$-$C_6$ alkoxy, CN, —$CONR^5R^6$, —$NR^5COR^6$, —$NR^5SO_2R^6$, —$SO_2R^5$, —$SO_2NR^5R^6$, —$NR^5R^6$ or —$NCOOR^5$, said alkyl and alkoxy groups substituted with 0-4 $R^{3a}$ groups;

r is 0, 1 or 2;

or a pharmaceutically acceptable salt, tautomer or stereoisomer thereof.

4. The compound according to claim 3 of formula I

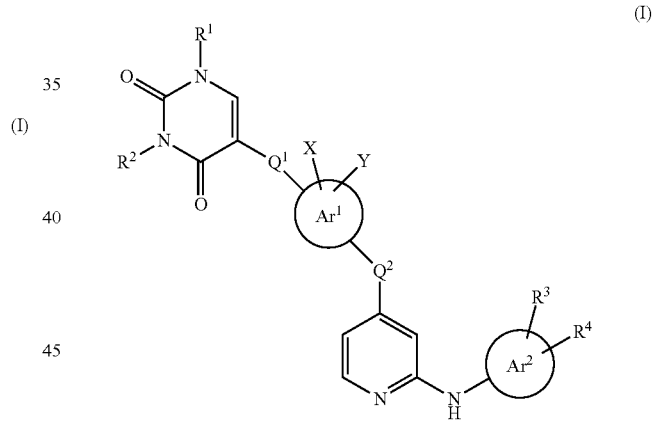

wherein:

$Ar^1$ is $C_3$-$C_8$ aryl $Ar^2$ is $C_3$-$C_8$ heteroaryl containing 1-4 heteroatoms selected from —N—, —O— or —S;

$Q^1$ is —NHCO— or —CONH;

$Q^2$ is —O—;

$R^1$ and $R^2$ are independently hydrogen, $C_1$-$C_6$ alkyl, —$(CH_2)_r$ $C_3$-$C_8$ cycloalkyl, —$(CH_2)_r$ $C_3$-$C_8$ aryl or —$(CH_2)_r$ $C_3$-$C_8$ heteroaryl containing 1-4 heteroatoms selected from —N—, —O— or —S—, said alkyl, cycloalkyl, aryl and heteroaryl groups substituted with 0-4 $R^{1a}$ groups;

$R^{1a}$ is hydrogen, halogen, $CF_3$, $C_1$-$C_3$ alkyl, $C_1$-$C_3$ alkoxy or —$COC_1$-$C_3$ alkyl;

$R^3$ and $R^4$ are independently hydrogen, halogen, $CF_3$, CN, $C_1$-$C_6$ alkyl, $C_1$-$C_6$ alkoxy, $C_3$-$C_8$ heterocyclyl containing 1-4 heteroatoms selected from —N—, —O— or —S—, —$CONR^5R^6$, —$NR^5COR^6$, —$NR^5SO_2R^6$, —SO₂R⁵, —SO₂NR⁵R⁶, —NR⁵R⁶ or —NCOOR⁵, said alkyl, heterocyclyl and alkoxy groups substituted with 0-4 R³ᵃ groups;

R³ᵃ is hydrogen, halogen, CHF₂, CF₃, C₁-C₆ alkyl, C₁-C₃ alkoxy, —(CH₂)ᵣCOOR⁵, OR⁵, —SO₂R⁵, —SO₂N⁵R⁶, —NR⁵R⁶, NR⁵COOR⁶ or —COC₁-C₃ alkyl;

R⁵ and R⁶ are independently hydrogen, C₁-C₆ alkyl or C₃-C₈ aryl, said aryl and alkyl groups substituted with 0-4 R⁵ᵃ; or R⁵ and R⁶ together with the nitrogen atoms to which they are attached form a heterocyclic ring containing 0-2 additional heteroatoms selected from —N—, —O— or —S— and are substituted with 0-2 R⁵ᵃ groups;

R⁵ᵃ is hydrogen, halogen, OH or C₁-C₃ alkyl;

X and Y are independently are independently hydrogen, halogen, C₁-C₆ alkyl, C₁-C₆ alkoxy, CN, —CONR⁵R⁶, —NR⁵COR⁶, —N⁵SO₂R⁶, —SO₂R⁵, —SO₂N⁵R⁶, —NR⁵R⁶ or —NCOOR⁵, said alkyl and alkoxy groups substituted with 0-4 R³ᵃ groups;

r is 0, 1 or 2;

or a pharmaceutically acceptable salt, tautomer or stereoisomer thereof.

5. The compound according to claim 4 of formula (I)

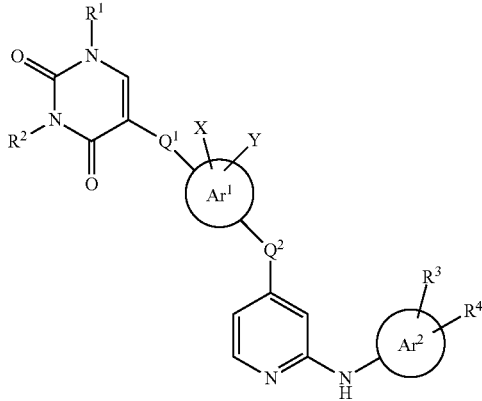

(I)

wherein:

Ar¹ is C₃-C₈ aryl

Ar² is C₃-C₈ heteroaryl containing 1-4 heteroatoms selected from —N—, —O— or —S;

Q¹ is —NHCO— or —CONH;

Q² is —O—;

R¹ and R² are independently hydrogen, C₁-C₆ alkyl, —(CH₂)ᵣ C₃-C₈ cycloalkyl, —(CH₂)ᵣ C₃-C₈ aryl or —(CH₂)ᵣ C₃-C₈ heteroaryl containing 1-4 heteroatoms selected from —N—, —O— or —S—, said alkyl, cycloalkyl, aryl and heteroaryl groups substituted with 0-4 R¹ᵃ groups;

R¹ᵃ is hydrogen, halogen, CF₃, C₁-C₃ alkyl, C₁-C₃ alkoxy or —COC₁-C₃ alkyl;

R³ and R⁴ are independently hydrogen, halogen, CF₃, CN, C₁-C₆ alkyl, C₁-C₆ alkoxy, C₃-C₈ heterocyclyl containing 1-4 heteroatoms selected from —N—, —O— or —S—, —CONR⁵R⁶, —NR⁵COR⁶, —NR⁵SO₂R⁶, —SO₂R⁵, —SO₂NR⁵R⁶, —NR⁵R⁶ or —NCOOR⁵, said alkyl, heterocyclyl and alkoxy groups substituted with 0-4 R³ᵃ groups;

R³ᵃ is hydrogen, halogen, CHF₂, CF₃, C₁-C₆ alkyl, C₁-C₃ alkoxy, —(CH₂)ᵣCOOR⁵, OR⁵, —SO₂R⁵, —SO₂NR⁵R⁶, —NR⁵R⁶, NR⁵COOR⁶ or —COC₁-C₃ alkyl;

R⁵ and R⁶ are independently hydrogen, C₁-C₆ alkyl or C₃-C₈ aryl, said aryl and alkyl groups substituted with 0-4 R⁵ᵃ; or R⁵ and R⁶ together with the nitrogen atoms to which they are attached form a heterocyclic ring containing 0-2 additional heteroatoms selected from —N—, —O— or —S— and are substituted with 0-2 R⁵ᵃ groups;

R⁵ᵃ is hydrogen, halogen, OH or C₁-C₃ alkyl;

X and Y are independently hydrogen, halogen or C₁-C₆ alkyl;

r is 0, 1 or 2;

or a pharmaceutically acceptable salt, tautomer or stereoisomer thereof.

6. The compound according to claim 5 of formula II

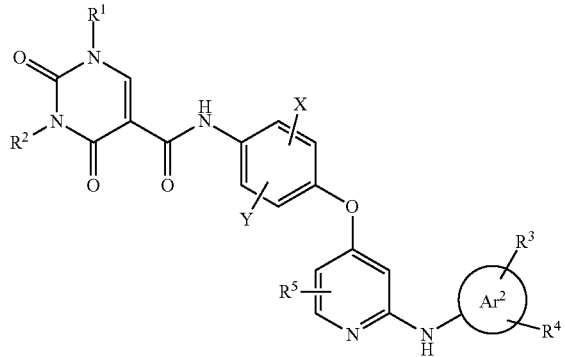

(II)

wherein:

Ar² is C₃-C₈ heteroaryl containing 1-4 heteroatoms selected from —N—, —O— or —S;

R¹ and R² are independently hydrogen, C₁-C₆ alkyl, —(CH₂)ᵣ C₃-C₈ cycloalkyl, —(CH₂)ᵣ C₃-C₈ aryl or —(CH₂)ᵣ C₃-C₈ heteroaryl containing 1-4 heteroatoms selected from —N—, —O— or —S—, said alkyl, cycloalkyl, aryl and heteroaryl groups substituted with 0-4 R¹ᵃ groups;

R¹ᵃ is hydrogen, halogen, CF₃, C₁-C₃ alkyl, C₁-C₃ alkoxy or —COC₁-C₃ alkyl;

R³ and R⁴ are independently hydrogen, halogen, CF₃, CN, C₁-C₆ alkyl, C₁-C₆ alkoxy, C₃-C₈ heterocyclyl containing 1-4 heteroatoms selected from —N—, —O— or —S—, —CONR⁵R⁶, —NR⁵COR⁶, —NR⁵SO₂R⁶, —SO₂R⁵, —SO₂NR⁵R⁶, —NR⁵R⁶ or —NCOOR⁵, said alkyl, heterocyclyl and alkoxy groups substituted with 0-4 R³ᵃ groups;

R³ᵃ is hydrogen, halogen, CHF₂, CF₃, C₁-C₆ alkyl, C₁-C₃ alkoxy, —(CH₂)ᵣCOOR⁵, OR⁵, —SO₂R⁵, —SO₂NR⁵R⁶, —NR⁵R⁶, NR⁵COOR⁶ or —COC₁-C₃ alkyl;

R⁵ and R⁶ are independently hydrogen, C₁-C₆ alkyl or C₃-C₈ aryl, said aryl and alkyl groups substituted with 0-4 R⁵ᵃ; or R⁵ and R⁶ together with the nitrogen atoms to which they are attached form a heterocyclic ring containing 0-2 additional heteroatoms selected from —N—, —O— or —S— and are substituted with 0-2 R⁵ᵃ groups;

R⁵ᵃ is hydrogen, halogen, OH or C₁-C₃ alkyl;

X and Y are independently hydrogen, halogen or C₁-C₆ alkyl;

r is 0, 1 or 2;

or a pharmaceutically acceptable salt, tautomer or stereoisomer thereof.

7. The compound according to claim 6 of formula (II)

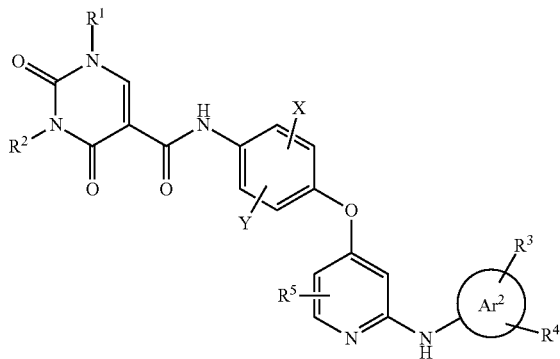

(II)

wherein:
- Ar² is C₃-C₈ heteroaryl containing 1-4 heteroatoms selected from —N—, —O— or —S;
- R¹ and R² are independently hydrogen, C₁-C₆ alkyl, —(CH₂)ᵣ C₃-C₈ cycloalkyl, —(CH₂)ᵣ C₃-C₈ aryl or —(CH₂)ᵣ C₃-C₈ heteroaryl containing 1-4 heteroatoms selected from —N—, —O— or —S—, said alkyl, cycloalkyl, aryl and heteroaryl groups substituted with 0-4 R¹ᵃ groups;
- R¹ᵃ is hydrogen, halogen, CF₃, C₁-C₃ alkyl, C₁-C₃ alkoxy or —COC₁-C₃ alkyl;
- R³ is hydrogen, halogen, CF₃, CN, C₁-C₆ alkyl, C₁-C₆ alkoxy, C₃-C₈ heterocyclyl containing 1-4 heteroatoms selected from —N—, —O— or —S—, —CONR⁵R⁶, —NR⁵COR⁶, —NR⁵SO₂R⁶, —SO₂R⁵, —SO₂NR⁵R⁶, —NR⁵R⁶ or —NCOOR⁵, said alkyl, heterocyclyl and alkoxy groups substituted with 0-4 R³ᵃ groups;
- R⁴ is hydrogen, halogen, CN, C₁-C₆ alkyl, C₃-C₈ heterocyclyl containing 1-4 heteroatoms selected from —N—, —O— or —S— or —NR⁵R⁶, said alkyl, heterocyclyl and alkoxy groups substituted with 0-4 R³ᵃ groups;
- R³ᵃ is hydrogen, halogen, CHF₂, CF₃, C₁-C₆ alkyl, C₁-C₃ alkoxy, —(CH₂)ᵣCOOR⁵, OR⁵, —SO₂R⁵, —SO₂NR⁵R⁶, —NR⁵R⁶, NR⁵COOR⁶ or —COC₁-C₃ alkyl;
- R⁵ and R⁶ are independently hydrogen, C₁-C₆ alkyl or C₃-C₈ aryl, said aryl and alkyl groups substituted with 0-4 R⁵ᵃ; or R⁵ and R⁶ together with the nitrogen atoms to which they are attached form a heterocyclic ring containing 0-2 additional heteroatoms selected from —N—, —O— or —S— and are substituted with 0-2 R⁵ᵃ groups;
- R⁵ᵃ is hydrogen, halogen, OH or C₁-C₃ alkyl;
- X and Y are independently hydrogen, halogen or C₁-C₆ alkyl;
- r is 0, 1 or 2;

or a pharmaceutically acceptable salt, tautomer or stereoisomer thereof.

8. A compound selected from
- N-[4-({2-[(5-cyanopyridin-2-yl)amino]pyridin-4-yl}oxy)-3-fluorophenyl]-3-(4-fluorophenyl)-2,4-dioxo-1-(propan-2-yl)-1,2,3,4-tetrahydropyrimidine-5-carboxamide,
- N-{4-[(2-{[5-(difluoromethyl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide,
- N-[3-fluoro-4-({2-[(5-methanesulfonylpyridin-2-yl)amino]pyridin-4-yl}oxy)phenyl]-3-(4-fluorophenyl)-2,4-dioxo-1-(propan-2-yl)-1,2,3,4-tetrahydropyrimidine-5-carboxamide,
- N-{4-[(2-{[5-(dimethylsulfamoyl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide,
- N-{4-[(2-{[5-(dimethylsulfamoyl)pyridin-2-yl]amino}pyridin-4-yl)oxy]-3-fluorophenyl}-3-(4-fluorophenyl)-2,4-dioxo-1-[(3S)-oxolan-3-yl]-1,2,3,4-tetrahydropyrimidine-5-carboxamide,
- N-{4-[(2-{[5-(dimethylsulfamoyl)pyridin-2-yl]amino}pyridin-4-yl)oxy]-3-fluorophenyl}-3-(5-fluoropyridin-2-yl)-2,4-dioxo-1-(propan-2-yl)-1,2,3,4-tetrahydropyrimidine-5-carboxamide,
- N-{4-[(2-{[5-(dimethylsulfamoyl)pyridin-2-yl]amino}pyridin-4-yl)oxy]-3-fluorophenyl}-3-(4-fluorophenyl)-1-[(2S)-1-hydroxypropan-2-yl]-2,4-dioxo-1,2,3,4-tetrahydropyrimidine-5-carboxamide,
- N-{4-[(2-{[5-(dimethylsulfamoyl)pyridin-2-yl]amino}pyridin-4-yl)oxy]-3-fluorophenyl}-3-(3-fluorophenyl)-2,4-dioxo-1-(propan-2-yl)-1,2,3,4-tetrahydropyrimidine-5-carboxamide,
- N-{4-[(2-{[5-(dimethylsulfamoyl)pyridin-2-yl]amino}pyridin-4-yl)oxy]phenyl}-2,4-dioxo-3-phenyl-1-(propan-2-yl)-1,2,3,4-tetrahydropyrimidine-5-carboxamide,
- N-{3-fluoro-4-[(2-{[5-(methylsulfamoyl)pyridin-2-yl]amino}pyridin-4-yl)oxy]phenyl}-3-(4-fluorophenyl)-2,4-dioxo-1-(propan-2-yl)-1,2,3,4-tetrahydropyrimidine-5-carboxamide,
- N-{4-[(2-{[5-(azetidine-1-sulfonyl)pyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide,
- N-{4-[(2-{[5-(dimethylsulfamoyl)-4-methylpyridin-2-yl]amino}pyridin-4-yl)oxy]-3-fluorophenyl}-3-(4-fluorophenyl)-2,4-dioxo-1-(propan-2-yl)-1,2,3,4-tetrahydropyrimidine-5-carboxamide, or a pharmaceutically acceptable salt thereof.

9. A pharmaceutical composition which comprises a compound according to claim 1 or a pharmaceutically acceptable salt thereof and one or more pharmaceutically acceptable carriers, diluents or excipients.

10. A compound according to claim 1 or a pharmaceutically acceptable salt thereof for use in the treatment of cancer wherein the cancer is small cell lung cancer, non-small cell lung cancer, triple-negative breast cancer, ovarian cancer, colorectal cancer, prostate cancer, melanoma, pancreatic cancer, multiple myeloma, T-acute lymphoblastic leukemia or AML.

* * * * *